US008329721B2

(12) United States Patent
Kshirsagar et al.

(10) Patent No.: US 8,329,721 B2
(45) **Date of Patent: *Dec. 11, 2012**

(54) **HYDROXY AND ALKOXY SUBSTITUTED 1*H*-IMIDAZONAPHTHYRIDINES AND METHODS**

(75) Inventors: Tushar A. Kshirsagar, Saint Paul, MN (US); Scott E. Langer, Saint Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 827 days.

This patent is subject to a terminal disclaimer.

(21) Appl. No.: 12/281,702

(22) PCT Filed: Mar. 14, 2007

(86) PCT No.: PCT/US2007/063976

§ 371 (c)(1), (2), (4) Date: Jul. 6, 2009

(87) PCT Pub. No.: WO2007/106854

PCT Pub. Date: Sep. 20, 2007

(65) Prior Publication Data

US 2009/0298821 A1 Dec. 3, 2009

Related U.S. Application Data

(60) Provisional application No. 60/743,490, filed on Mar. 15, 2006.

(51) Int. Cl.

| | |
|---|---|
| ***A61K 31/437*** | (2006.01) |
| ***A61K 31/4375*** | (2006.01) |
| ***C07D 471/04*** | (2006.01) |

(52) U.S. Cl. ......................................... 514/290; 546/82

(58) Field of Classification Search .................... 546/82; 514/290

See application file for complete search history.

(56) References Cited

U.S. PATENT DOCUMENTS

| | | | | |
|---|---|---|---|---|
| 3,314,941 | A | 4/1967 | Littell et al. | |
| 4,689,338 | A | 8/1987 | Gerster | |
| 4,698,348 | A | 10/1987 | Gerster | |
| 4,929,624 | A | 5/1990 | Gerster et al. | |
| 4,988,815 | A | 1/1991 | Andre et al. | |
| 5,037,986 | A | 8/1991 | Gerster | |
| 5,175,296 | A | 12/1992 | Gerster | |
| 5,238,944 | A | 8/1993 | Wick et al. | |
| 5,266,575 | A | 11/1993 | Gerster | |
| 5,268,376 | A | 12/1993 | Gerster | |
| 5,346,905 | A | 9/1994 | Gerster | |
| 5,352,784 | A | 10/1994 | Nikolaides et al. | 594/126 |
| 5,367,076 | A | 11/1994 | Gerster | |
| 5,389,640 | A | 2/1995 | Gerster et al. | |
| 5,395,937 | A | 3/1995 | Nikolaides et al. | |
| 5,444,065 | A | 8/1995 | Nikolaides et al. | |
| 5,446,153 | A | 8/1995 | Lindstrom et al. | |
| 5,482,936 | A | 1/1996 | Lindstrom | |
| 5,494,916 | A | 2/1996 | Lindstrom et al. | |
| 5,525,612 | A | 6/1996 | Gerster | |
| 5,627,281 | A | 5/1997 | Nikolaides et al. | |
| 5,644,063 | A | 7/1997 | Lindstrom et al. | |
| 5,648,516 | A | 7/1997 | Nikolaides et al. | |
| 5,693,811 | A | 12/1997 | Lindstrom | |
| 5,714,608 | A | 2/1998 | Gerster | |
| 5,741,908 | A | 4/1998 | Gerster et al. | |
| 5,756,747 | A | 5/1998 | Gerster et al. | |
| 5,886,006 | A | 3/1999 | Nikolaides et al. | |
| 5,939,090 | A | 8/1999 | Beaurline et al. | |
| 6,039,969 | A | 3/2000 | Tomai et al. | |
| 6,069,149 | A | 5/2000 | Nanba et al. | |
| 6,083,505 | A | 7/2000 | Miller et al. | |
| 6,110,929 | A | 8/2000 | Gerster et al. | |
| 6,194,425 | B1 | 2/2001 | Gerster et al. | 514/293 |
| 6,200,592 | B1 | 3/2001 | Tomai et al. | |
| 6,245,776 | B1 | 6/2001 | Skwierczynski et al. | 514/293 |
| 6,331,539 | B1 | 12/2001 | Crooks et al. | |
| 6,365,166 | B2 | 4/2002 | Beaurline et al. | |
| 6,376,669 | B1 | 4/2002 | Rice et al. | |
| 6,440,992 | B1 | 8/2002 | Gerster et al. | |
| 6,451,810 | B1 | 9/2002 | Coleman et al. | |
| 6,486,168 | B1 | 11/2002 | Skwierczynski et al. | |
| 6,514,985 | B1 | 2/2003 | Gerster et al. | |
| 6,518,265 | B1 | 2/2003 | Kato et al. | |
| 6,525,064 | B1 | 2/2003 | Dellaria et al. | |
| 6,541,485 | B1 | 4/2003 | Crooks et al. | |
| 6,545,016 | B1 | 4/2003 | Dellaria et al. | |
| 6,545,017 | B1 | 4/2003 | Dellaria et al. | |

(Continued)

FOREIGN PATENT DOCUMENTS

| | | |
|---|---|---|
| EP | 0 394 026 | 10/1990 |

(Continued)

OTHER PUBLICATIONS

Wozniak et al., "The Amination of 3-nitro-1, 5-naphthyridines by Liquid Ammonia/Potassium Permanganate[1,2]. A New and Covenient Amination Method", *Journal of the Royal Netherlands Chemical Society*, 102, pp. 511-513, Dec. 12, 1983. Brennan et al., "Automated Bioassay of Interferons in Micro-test Plates.", *Biotechniques*, Jun./Jul. 78, 1983.

Testerman et al., "Cytokine Induction by the Immunomodulators Imiquimod and S-27609.", *Journal of Leukocyte Biology*, vol. 58, pp. 365-372, Sep. 1995.

Bachman et al., "Synthesis of Substituted Quinolylamines. Derivatives of 4-Amino-7-Chloroquinoline.", *J. Org. Chem.* 15, pp. 1278-1284 (1950).

Jain et al., "Chemical and Pharmacological Investigations of Some ω-Substituted Alkylamino-3-aminopyridines.", *J. Med. Chem.*, 11, pp. 87-92 (1968).

Baranov et al., "Pyrazoles, Imidazoles, and Other 5-Membered Rings.", *Chem. Abs.* 85, 94362, (1976).

Berényi et al., "Ring Transformation of Condensed Dihydro-as-triazines.", *J. Heterocyclic Chem.*, 18, pp. 1537-1540 (1981).

Chollet et al., "Development of a Topically Active Imiquimod Formulation.", *Pharmaceutical Development and Technology*, 4(1), pp. 35-43 (1999).

Izumi et al., "1*H*-Imidazo[4,5-*c*]quinoline Derivatives as Novel Potent TNF-α Suppressors: Synthesis and Structure-Activity Relationship of 1-, 2- and 4-Substituted 1*H*-imidazo[4,5-*c*]pyridines.", *Bioorganic & Medicinal Chemistry*, 11, pp. 2541-2550 (2003).

(Continued)

*Primary Examiner* — Rita Desai

(57) ABSTRACT

1H-Imidazo[4,5-c]naphthyridin-4-amines with a hydroxy, alkoxy, hydroxyalkoxy, or alkoxyalkoxy substituent at the 2-position, pharmaceutical compositions containing these compounds, methods of making the compounds, intermediates, and methods of use of these compounds as immunomodulators, for inducing cytokine biosynthesis in animals and in the treatment of diseases including viral and neoplastic diseases, are disclosed.

14 Claims, No Drawings

U.S. PATENT DOCUMENTS

| | | | | |
|---|---|---|---|---|
| 6,558,951 | B1 | 5/2003 | Tomai et al. | |
| 6,573,273 | B1 | 6/2003 | Crooks et al. | |
| 6,610,319 | B2 | 8/2003 | Tomai et al. | |
| 6,627,638 | B2 | 9/2003 | Gerster et al. | |
| 6,627,640 | B2 | 9/2003 | Gerster et al. | |
| 6,630,588 | B2 | 10/2003 | Rice et al. | |
| 6,656,938 | B2 | 12/2003 | Crooks et al. | |
| 6,660,735 | B2 | 12/2003 | Crooks et al. | |
| 6,660,747 | B2 | 12/2003 | Crooks et al. | |
| 6,664,260 | B2 | 12/2003 | Charles et al. | |
| 6,664,264 | B2 | 12/2003 | Dellaria et al. | |
| 6,664,265 | B2 | 12/2003 | Crooks et al. | |
| 6,667,312 | B2 | 12/2003 | Bonk et al. | |
| 6,670,372 | B2 | 12/2003 | Charles et al. | |
| 6,677,347 | B2 | 1/2004 | Crooks et al. | |
| 6,677,348 | B2 | 1/2004 | Heppner et al. | |
| 6,677,349 | B1 | 1/2004 | Griesgraber | |
| 6,683,088 | B2 | 1/2004 | Crooks et al. | |
| 6,696,076 | B2 | 2/2004 | Tomai et al. | |
| 6,696,465 | B2 | 2/2004 | Dellaria et al. | |
| 6,703,402 | B2 | 3/2004 | Gerster et al. | |
| 6,706,728 | B2 | 3/2004 | Hedenstrom et al. | |
| 6,716,988 | B2 | 4/2004 | Dellaria et al. | |
| 6,720,333 | B2 | 4/2004 | Dellaria et al. | |
| 6,720,334 | B2 | 4/2004 | Dellaria et al. | |
| 6,720,422 | B2 | 4/2004 | Dellaria et al. | |
| 6,743,920 | B2 | 6/2004 | Lindstrom et al. | |
| 6,756,382 | B2 | 6/2004 | Rice et al. | |
| 6,797,718 | B2 | 9/2004 | Dellaria et al. | |
| 6,800,624 | B2 | 10/2004 | Crooks et al. | |
| 6,809,203 | B2 | 10/2004 | Gerster et al. | |
| 6,818,650 | B2 | 11/2004 | Griesgraber | |
| 6,825,350 | B2 | 11/2004 | Crooks et al. | |
| 6,841,678 | B2 | 1/2005 | Merli et al. | |
| 6,852,861 | B2 | 2/2005 | Merli et al. | |
| 6,878,719 | B2 | 4/2005 | Lindstrom et al. | |
| 6,888,000 | B2 | 5/2005 | Crooks et al. | |
| 6,894,060 | B2 | 5/2005 | Slade | |
| 6,897,221 | B2 | 5/2005 | Crooks et al. | |
| 6,903,113 | B2 | 6/2005 | Heppner et al. | |
| 6,916,925 | B1 | 7/2005 | Rice et al. | |
| 6,921,826 | B2 | 7/2005 | Dellaria et al. | |
| 6,924,293 | B2 | 8/2005 | Lindstrom | |
| 6,943,225 | B2 | 9/2005 | Lee et al. | |
| 6,949,649 | B2 | 9/2005 | Bonk et al. | |
| 6,953,804 | B2 | 10/2005 | Dellaria et al. | |
| 6,969,722 | B2 | 11/2005 | Heppner et al. | |
| 6,989,389 | B2 | 1/2006 | Heppner et al. | |
| 7,030,129 | B2 | 4/2006 | Miller et al. | |
| 7,030,131 | B2 | 4/2006 | Crooks et al. | |
| 7,038,053 | B2 | 5/2006 | Lindstrom et al. | |
| 7,049,439 | B2 | 5/2006 | Crooks et al. | |
| 7,078,523 | B2 | 7/2006 | Crooks et al. | |
| 7,091,214 | B2 | 8/2006 | Hays et al. | |
| 7,093,901 | B2 * | 8/2006 | Yamada | 297/367 R |
| 7,098,221 | B2 | 8/2006 | Heppner et al. | |
| 7,112,677 | B2 | 9/2006 | Griesgraber | |
| 7,115,622 | B2 | 10/2006 | Crooks et al. | |
| 7,125,890 | B2 | 10/2006 | Dellaria et al. | |
| 7,132,429 | B2 | 11/2006 | Griesgraber et al. | |
| 7,132,438 | B2 | 11/2006 | Frenkel et al. | |
| 7,148,232 | B2 | 12/2006 | Gerster et al. | |
| 7,157,453 | B2 | 1/2007 | Crooks et al. | |
| 7,163,947 | B2 | 1/2007 | Griesgraber et al. | |
| 7,179,253 | B2 | 2/2007 | Graham et al. | |
| 7,199,131 | B2 | 4/2007 | Lindstrom | |
| 7,214,675 | B2 | 5/2007 | Griesgraber | |
| 7,220,758 | B2 | 5/2007 | Dellaria et al. | |
| 7,226,928 | B2 | 6/2007 | Mitra et al. | |
| 7,276,515 | B2 | 10/2007 | Dellaria et al. | |
| 7,288,550 | B2 | 10/2007 | Dellaria et al. | |
| 7,301,027 | B2 | 11/2007 | Colombo et al. | |
| 7,375,180 | B2 | 5/2008 | Gorden et al. | |
| 7,387,271 | B2 | 6/2008 | Noelle et al. | |
| 7,393,859 | B2 | 7/2008 | Coleman et al. | |
| 7,427,629 | B2 | 9/2008 | Kedl et al. | |
| 7,485,432 | B2 | 2/2009 | Fink et al. | |
| 7,544,697 | B2 | 6/2009 | Hays et al. | |

| | | | | |
|---|---|---|---|---|
| 7,576,068 | B2 | 8/2009 | Averett | |
| 7,578,170 | B2 | 8/2009 | Mayer et al. | |
| 7,579,359 | B2 | 8/2009 | Krepski et al. | |
| 7,598,382 | B2 | 10/2009 | Hays et al. | |
| 7,612,083 | B2 | 11/2009 | Griesgraber | |
| 7,648,997 | B2 | 1/2010 | Kshirsagar et al. | |
| 7,655,672 | B2 | 2/2010 | Statham et al. | |
| 7,687,628 | B2 | 3/2010 | Gutman et al. | |
| 7,696,159 | B2 | 4/2010 | Owens et al. | |
| 7,699,057 | B2 | 4/2010 | Miller et al. | |
| 7,731,967 | B2 | 6/2010 | O'Hagan et al. | |
| 7,799,800 | B2 | 9/2010 | Wightman | |
| 7,879,849 | B2 | 2/2011 | Hays et al. | |
| 7,884,207 | B2 | 2/2011 | Stoermer et al. | |
| 7,888,349 | B2 | 2/2011 | Kshirsagar et al. | |
| 7,897,597 | B2 | 3/2011 | Lindstrom et al. | |
| 7,897,609 | B2 * | 3/2011 | Niwas et al. | 514/293 |
| 7,897,767 | B2 | 3/2011 | Kshirsagar et al. | |
| 7,902,209 | B2 | 3/2011 | Statham et al. | |
| 7,902,210 | B2 | 3/2011 | Statham et al. | |
| 7,902,211 | B2 | 3/2011 | Statham et al. | |
| 7,902,212 | B2 | 3/2011 | Statham et al. | |
| 7,902,213 | B2 | 3/2011 | Statham et al. | |
| 7,902,214 | B2 | 3/2011 | Statham et al. | |
| 7,902,215 | B2 | 3/2011 | Statham et al. | |
| 7,902,216 | B2 | 3/2011 | Statham et al. | |
| 7,902,242 | B2 | 3/2011 | Statham et al. | |
| 7,902,243 | B2 | 3/2011 | Statham et al. | |
| 7,902,244 | B2 | 3/2011 | Statham et al. | |
| 7,902,245 | B2 | 3/2011 | Statham et al. | |
| 7,902,246 | B2 | 3/2011 | Statham et al. | |
| 7,968,562 | B2 | 6/2011 | Skwierczynski et al. | |
| 7,968,563 | B2 | 6/2011 | Kshirsager et al. | |
| 7,993,659 | B2 | 8/2011 | Noelle et al. | |
| 8,017,779 | B2 | 9/2011 | Merrill et al. | |
| 8,026,366 | B2 | 9/2011 | Prince et al. | |
| 8,088,790 | B2 * | 1/2012 | Kshirsagar et al. | 514/293 |
| 2002/0055517 | A1 | 5/2002 | Smith | |
| 2002/0058674 | A1 | 5/2002 | Hedenstrom et al. | |
| 2002/0107262 | A1 | 8/2002 | Lindstrom | |
| 2003/0133913 | A1 | 7/2003 | Tomai et al. | |
| 2003/0139364 | A1 | 7/2003 | Krieg et al. | 514/44 |
| 2003/0185835 | A1 | 10/2003 | Braun | 424/184.1 |
| 2004/0014779 | A1 | 1/2004 | Gorden et al. | |
| 2004/0076633 | A1 | 4/2004 | Thomsen et al. | 424/184.1 |
| 2004/0132079 | A1 | 7/2004 | Gupta et al. | |
| 2004/0147543 | A1 | 7/2004 | Hays et al. | 514/292 |
| 2004/0175336 | A1 | 9/2004 | Egging et al. | |
| 2004/0180919 | A1 | 9/2004 | Lee et al. | |
| 2004/0191833 | A1 | 9/2004 | Fink et al. | |
| 2004/0197865 | A1 | 10/2004 | Gupta et al. | |
| 2004/0202720 | A1 | 10/2004 | Wightman et al. | |
| 2004/0214851 | A1 | 10/2004 | Birmachu et al. | |
| 2004/0258698 | A1 | 12/2004 | Wightman et al. | 424/178.1 |
| 2004/0265351 | A1 | 12/2004 | Miller et al. | 424/423 |
| 2005/0009858 | A1 | 1/2005 | Martinez-Colon et al. | 514/292 |
| 2005/0048072 | A1 | 3/2005 | Kedl et al. | |
| 2005/0059072 | A1 | 3/2005 | Birmachu et al. | |
| 2005/0070460 | A1 | 3/2005 | Hammerbeck et al. | |
| 2005/0096259 | A1 | 5/2005 | Tomai et al. | |
| 2005/0106300 | A1 | 5/2005 | Chen et al. | |
| 2005/0158325 | A1 | 7/2005 | Hammerbeck et al. | |
| 2005/0165043 | A1 | 7/2005 | Miller et al. | |
| 2005/0171072 | A1 | 8/2005 | Tomai et al. | |
| 2005/0239735 | A1 | 10/2005 | Miller et al. | |
| 2005/0245562 | A1 | 11/2005 | Garcia-Echeverria et al. | |
| 2006/0045885 | A1 | 3/2006 | Kedl et al. | |
| 2006/0045886 | A1 | 3/2006 | Kedl | |
| 2006/0051374 | A1 | 3/2006 | Miller et al. | |
| 2006/0088542 | A1 | 4/2006 | Braun | |
| 2006/0142202 | A1 | 6/2006 | Alkan et al. | |
| 2006/0142235 | A1 | 6/2006 | Miller et al. | |
| 2006/0195067 | A1 | 8/2006 | Wolter et al. | |
| 2006/0216333 | A1 | 9/2006 | Miller et al. | |
| 2007/0060754 | A1 | 3/2007 | Lindstrom et al. | 546/82 |
| 2007/0066639 | A1 | 3/2007 | Kshirsagar et al. | |
| 2007/0072893 | A1 | 3/2007 | Krepski et al. | |
| 2007/0099901 | A1 | 5/2007 | Krepski et al. | |
| 2007/0123559 | A1 | 5/2007 | Statham et al. | |

| | | | | |
|---|---|---|---|---|
| 2007/0155767 | A1 | 7/2007 | Radmer et al. | |
| 2007/0166384 | A1 | 7/2007 | Zarraga et al. | |
| 2007/0167479 | A1 | 7/2007 | Busch et al. | |
| 2007/0213355 | A1 | 9/2007 | Capraro et al. | |
| 2007/0219196 | A1 | 9/2007 | Krepski et al. | |
| 2007/0243215 | A1 | 10/2007 | Miller et al. | |
| 2007/0259881 | A1 | 11/2007 | Dellaria et al. | |
| 2007/0259907 | A1 | 11/2007 | Prince | |
| 2007/0287725 | A1 | 12/2007 | Moser et al. | |
| 2007/0292456 | A1 | 12/2007 | Hammerbeck et al. | |
| 2008/0015184 | A1 | 1/2008 | Kshirsagar et al. | |
| 2008/0039533 | A1 | 2/2008 | Sahouani et al. | |
| 2008/0063714 | A1 | 3/2008 | Sahouani et al. | |
| 2008/0070907 | A1 | 3/2008 | Griesgraber et al. | |
| 2008/0085895 | A1 | 4/2008 | Griesgraber et al. | |
| 2008/0119508 | A1 | 5/2008 | Slade et al. | |
| 2008/0188469 | A1 | 8/2008 | Thomsen et al. | 514/229.8 |
| 2008/0188513 | A1 | 8/2008 | Skwierczynski et al. | |
| 2008/0193468 | A1 | 8/2008 | Levy et al. | |
| 2008/0193474 | A1 | 8/2008 | Griesgraber et al. | |
| 2008/0207674 | A1 | 8/2008 | Stoesz et al. | |
| 2008/0213308 | A1 | 9/2008 | Valiante et al. | |
| 2008/0262021 | A1 | 10/2008 | Capraro et al. | |
| 2008/0262022 | A1 | 10/2008 | Lee et al. | |
| 2008/0269192 | A1 | 10/2008 | Griesgraber et al. | |
| 2008/0306252 | A1 | 12/2008 | Crooks et al. | |
| 2008/0306266 | A1 | 12/2008 | Martin et al. | |
| 2008/0312434 | A1 | 12/2008 | Lindstrom et al. | |
| 2008/0318998 | A1 | 12/2008 | Prince et al. | |
| 2009/0005371 | A1 | 1/2009 | Rice et al. | |
| 2009/0017076 | A1 | 1/2009 | Miller et al. | |
| 2009/0018122 | A1 | 1/2009 | Lindstrom et al. | 514/227.8 |
| 2009/0023720 | A1 | 1/2009 | Kshirsagar et al. | |
| 2009/0023722 | A1 | 1/2009 | Coleman et al. | |
| 2009/0029988 | A1 | 1/2009 | Kshirsagar et al. | |
| 2009/0030030 | A1 | 1/2009 | Bonk et al. | |
| 2009/0030031 | A1 | 1/2009 | Kshirsagar et al. | |
| 2009/0035323 | A1 | 2/2009 | Stoermer et al. | |
| 2009/0062272 | A1 | 3/2009 | Bonk et al. | |
| 2009/0069299 | A1 | 3/2009 | Merrill et al. | |
| 2009/0069314 | A1 | 3/2009 | Kshirsagar et al. | |
| 2009/0075980 | A1 | 3/2009 | Hays et al. | |
| 2009/0099161 | A1 | 4/2009 | Rice et al. | |
| 2009/0105295 | A1 | 4/2009 | Kshirsagar et al. | |
| 2009/0124611 | A1 | 5/2009 | Hays et al. | |
| 2009/0124652 | A1 | 5/2009 | Ach et al. | |
| 2009/0163532 | A1 | 6/2009 | Perman et al. | |
| 2009/0163533 | A1 | 6/2009 | Hays et al. | |
| 2009/0176821 | A1 | 7/2009 | Kshirsagar et al. | |
| 2009/0202443 | A1 | 8/2009 | Miller et al. | |
| 2009/0221551 | A1 | 9/2009 | Kshirsagar et al. | |
| 2009/0221556 | A1 | 9/2009 | Kshirsagar et al. | |
| 2009/0240055 | A1 | 9/2009 | Krepski et al. | |
| 2009/0246174 | A1 | 10/2009 | Rook et al. | |
| 2009/0253695 | A1 | 10/2009 | Kshirsagar et al. | |
| 2009/0270443 | A1 | 10/2009 | Stoermer et al. | |
| 2009/0298821 | A1 | 12/2009 | Kshirsagar et al. | |
| 2009/0306388 | A1 | 12/2009 | Zimmerman et al. | |
| 2010/0028381 | A1 | 2/2010 | Gorski et al. | |
| 2010/0056557 | A1 | 3/2010 | Benninghoff et al. | |
| 2010/0096287 | A1 | 4/2010 | Stoesz et al. | |
| 2010/0113565 | A1 | 5/2010 | Gorden et al. | |
| 2010/0152230 | A1 | 6/2010 | Dellaria et al. | |
| 2010/0158928 | A1 | 6/2010 | Stoermer et al. | |
| 2010/0173906 | A1 | 7/2010 | Griesgraber | |
| 2010/0180902 | A1 | 7/2010 | Miller et al. | |
| 2010/0240693 | A1 | 9/2010 | Lundquist et al. | |
| 2011/0021554 | A1 | 1/2011 | Stoesz et al. | |

FOREIGN PATENT DOCUMENTS

| | | |
|---|---|---|
| EP | 1 104 764 | 6/2001 |
| JP | 9-208584 | 8/1997 |
| JP | 11-080156 A | 3/1999 |
| JP | 11-222432 | 8/1999 |
| JP | 2000-247884 | 9/2000 |
| WO | WO 02/36592 | 5/2002 |
| WO | WO 0236592 | 5/2002 |
| WO | WO 03077944 | 9/2003 |
| WO | WO 2005/003064 | 1/2005 |
| WO | WO 2005020999 | 3/2005 |
| WO | WO 2005032484 | 4/2005 |
| WO | WO 2006/028451 | 3/2006 |
| WO | WO 2006038923 | 4/2006 |
| WO | WO 2006/063072 | 6/2006 |
| WO | WO 2006/121528 | 11/2006 |
| WO | WO 2006122806 | 11/2006 |
| WO | WO 2007/030775 | 3/2007 |
| WO | WO 2007056112 | 5/2007 |

OTHER PUBLICATIONS

Hirota, K., et al., "Novel and Efficient Synthesis of 8-Oxoadenine Derivatives", Heterocycles, 2001, pp. 2279-2282, No. 12, vol. 55.

Testerman, et al., "Cytokine Induction by Immunomodulators Imiquimod and S-27609", Journal of Leukocyte Biology, Sep. 1995, pp. 365-372, vol. 58.

* cited by examiner

HYDROXY AND ALKOXY SUBSTITUTED 1*H*-IMIDAZONAPHTHYRIDINES AND METHODS

CROSS REFERENCE TO RELATED APPLICATIONS

The present invention claims priority to U.S. Provisional Application Ser. No. 60/743,490, filed Mar. 15, 2006, which is incorporated herein by reference.

BACKGROUND

Certain compounds have been found to be useful as immune response modifiers (IRMs), rendering them useful in the treatment of a variety of disorders. However, there continues to be interest in and a need for compounds that have the ability to modulate the immune response, by induction of cytokine biosynthesis or other means.

SUMMARY OF THE INVENTION

It has now been found that certain 2-hydroxy- and 2-alkoxy-1H-imidazo[4,5-c]naphthyridin-4-amines modulate cytokine biosynthesis. In one aspect, the present invention provides compounds, which are of the following Formula I:

I

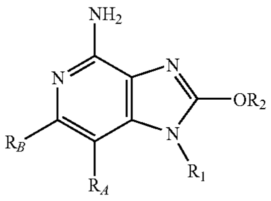

and more specifically compounds of the following Formulas II, III, IV, V, VI, VII, VIII, IX, IX, X, and XI:

II

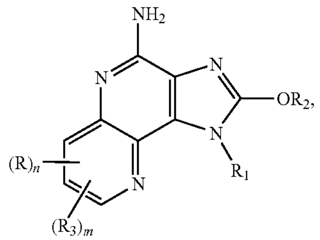

III

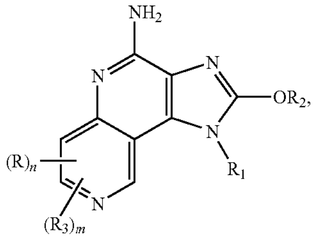

-continued

IV

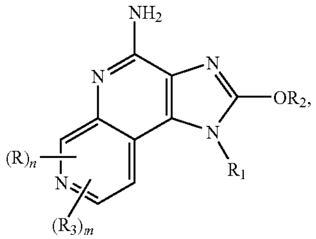

V

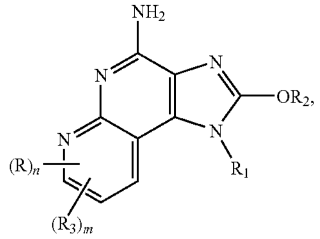

VI

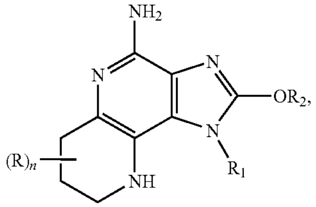

VII

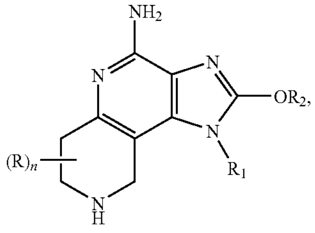

VIII

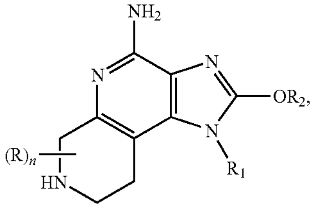

IX

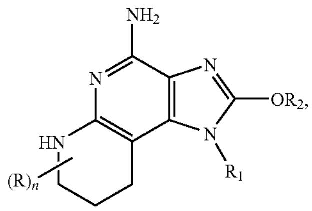

X

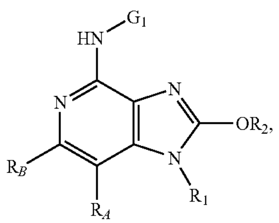

-continued

XI

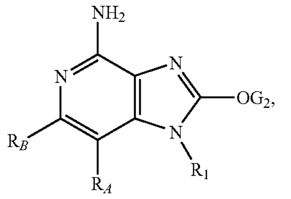

wherein $R_A$, $R_B$, R, $R_1$, $R_2$, $R_3$, $G_1$, $G_2$, m, and n are as defined below; and pharmaceutically acceptable salts thereof.

The compounds or salts of Formulas I, II, III, IV, V, VI, VII, VIII. IX, X, and XI are useful as IRMs due to their ability to modulate cytokine biosynthesis (e.g., induce the biosynthesis or production of one or more cytokines) and otherwise modulate the immune response when administered to animals. The ability to modulate cytokine biosynthesis makes the compounds useful in the treatment of a variety of conditions such as viral diseases and neoplastic diseases that are responsive to such changes in the immune response.

In another aspect, the present invention also provides pharmaceutical compositions containing the compounds of Formulas I, II, III, IV, V, VI, VII, VIII, IX, X, and/or XI.

In another aspect of particular importance, the present invention provides methods of inducing cytokine biosynthesis in animal cells, treating a viral disease in an animal, and/or treating a neoplastic disease in an animal by administering to the animal one or more compounds of the Formulas I, II, III, IV, V, VI, VII, VIII, IX, X, and/or XI, and/or pharmaceutically acceptable salts thereof.

In another aspect, the invention provides methods of synthesizing the compounds of Formulas I, II, III, IV, V, VI, VII, VIII, IX, X, and XI and intermediate compounds useful in the synthesis of these compounds.

As used herein, "a", "an", "the", "at least one", and "one or more" are used interchangeably.

The terms "comprising" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. Guidance is also provided herein through lists of examples, which can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formulas I through XI:

I

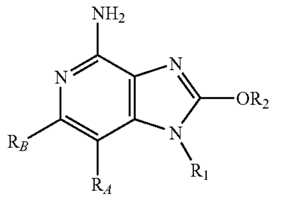

-continued

II

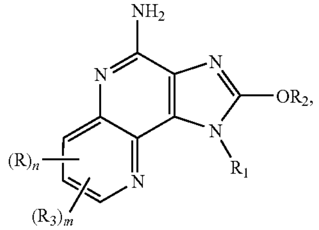

III

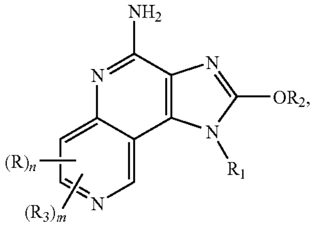

IV

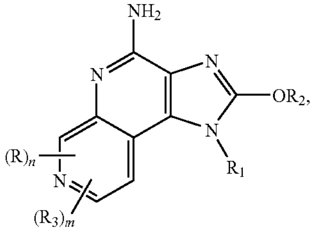

V

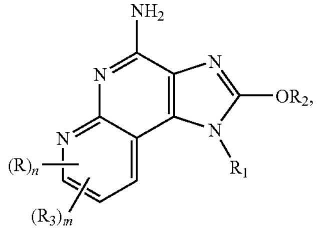

VI

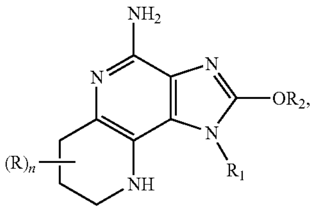

VII

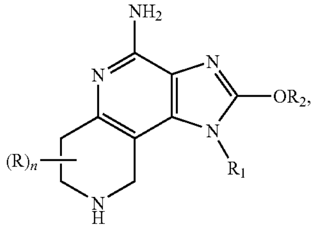

VIII

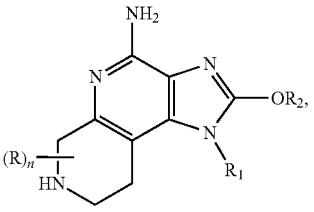

-continued

IX

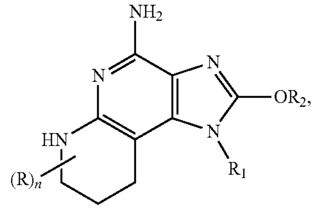

X

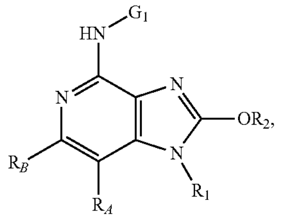

XI

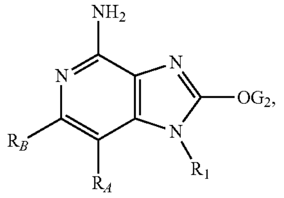

and the intermediate compound of Formula XIV

XIV

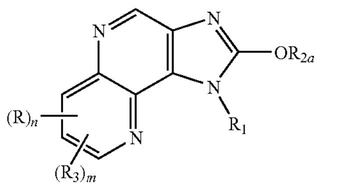

wherein $R_A$, $R_B$, R, $R_1$, $R_2$, $R_{2a}$, $R_3$, $G_1$, $G_2$, m, and n are as defined below; and pharmaceutically acceptable salts thereof.

In one embodiment, the present invention provides a compound of the following Formula I:

I

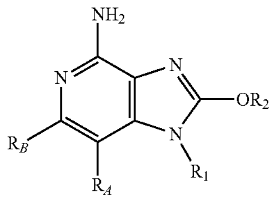

wherein:

$R_2$ is selected from the group consisting of hydrogen, $C_{1-4}$ alkyl, hydroxy$C_{2-4}$ alkylenyl, and $C_{1-4}$ alkoxy$C_{2-4}$ alkylenyl;

$R_1$ is selected from the group consisting of:

hydrogen,

—$CH(R_{11})$—Ar,

—$CH(R_{11})$—Ar'-$R_4$,

—$CH(R_{11})$—Ar'-Y—$R_4$,

—$CH(R_{11})$—Ar'-$CH(R_{11})$—Y—$R_4$,

—$CH(R_{11})$—Ar'-$R_5$,

—$CH(R_{11})$—Ar'-$CH(R_{11})$—$R_5$,

—$X_1$-Het, and

—$X_1$—$N(R_8)$-Q-$R_4$;

$R_A$ and $R_B$ taken together form a fused pyridine ring that is unsubstituted or substituted by one $R_3$ group, or substituted by one $R_3$ group and one R group, or substituted by one or more R groups;

or $R_A$ and $R_B$ taken together form a fused tetrahydropyridine ring that is unsubstituted or substituted by one or more R groups;

Ar is selected from the group consisting of aryl and heteroaryl each of which is unsubstituted or substituted by one or more substituents independently selected from the group consisting of alkyl, alkenyl, alkoxy, methylenedioxy, haloalkyl, haloalkoxy, halogen, nitro, hydroxy, hydroxyalkyl, cyano, amino, alkylamino, and dialkylamino;

Ar' is selected from the group consisting of arylene and heteroarylene each of which is unsubstituted or substituted by one or more substituents independently selected from the group consisting of alkyl, alkenyl, alkoxy, haloalkyl, haloalkoxy, halogen, nitro, hydroxy, hydroxyalkyl, cyano, amino, alkylamino, and dialkylamino;

Het is heterocyclyl which is unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;

$X_1$ is $C_{1-6}$ alkylene that is optionally interrupted by one or more —O— groups;

$R_{11}$ is selected from the group consisting of hydrogen and $C_{1-3}$ alkylene;

R is selected from the group consisting of:

halogen, hydroxy, alkyl, alkenyl, haloalkyl, alkoxy, alkylthio, and

—$N(R_9)_2$;

$R_3$ is selected from the group consisting of:

—Z—$R_4$,

—Z—X—$R_4$,

—Z—X—Y—$R_4$,

—Z—X—Y—X—Y—$R_4$, and

—Z—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:

—O—,

—$S(O)_{0-2}$—,

—$S(O)_2$—$N(R_8)$—,

—$C(R_6)$—,

—$C(R_6)$—O—,

—O—$C(R_6)$—,

—O—C(O)—O—,

—$N(R_8)$-Q-,

—$C(R_6)$—$N(R_8)$—,

—O—$C(R_6)$—$N(R_8)$—,

—$C(R_6)$—$N(OR_9)$—,

O—$N(R_8)$-Q-,

—O—N=$C(R_4)$—,

—C(═N—O—$R_8$)—,

—CH(—N(—O—$R_5$)-Q-$R_4$)—,

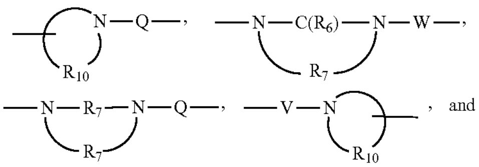

and

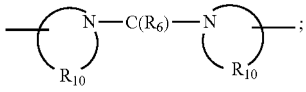

;

Z is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;

$R_5$ is selected from the group consisting of:

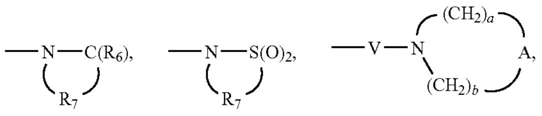

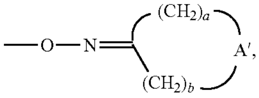

and

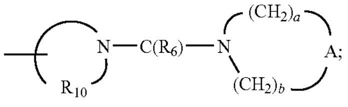

;

$R_6$ is selected from the group consisting of ═O and ═S;

$R_7$ is $C_{2-7}$ alkylene;

$R_8$ is selected from the group consisting of hydrogen, $C_{1-10}$ alkyl, $C_{2-10}$ alkenyl, hydroxy-$C_{1-10}$ alkylenyl, $C_{1-10}$ alkoxy-$C_{1-10}$ alkylenyl, aryl-$C_{1-10}$ alkylenyl, and heteroaryl-$C_{1-10}$ alkylenyl;

$R_9$ is selected from the group consisting of hydrogen and alkyl;

$R_{10}$ is $C_{3-8}$ alkylene;

A is selected from the group consisting of —$CH_2$—, —O—, —C(O)—, —$S(O)_{0-2}$—, and —N(-Q-$R_4$)—;

A' is selected from the group consisting of —O—, —$S(O)_{0-2}$—, —N(-Q-$R_4$)—, and —$CH_2$—;

Q is selected from the group consisting of a bond, —C($R_6$)—, —C($R_6$)—C($R_6$)—, —$S(O)_2$—, —C($R_6$)—N($R_8$)—W—, —$S(O)_2$—N($R_8$)—, —C($R_6$)—O—, —C($R_6$)—S—, and —C($R_6$)—N($OR_9$)—;

V is selected from the group consisting of —C($R_6$)—, —O—C($R_6$)—, —N($R_8$)—C($R_6$)—, and —$S(O)_2$—;

W is selected from the group consisting of a bond, —C(O)—, and —$S(O)_2$—; and a and b are independently integers from 1 to 6 with the proviso that a+b is ≦7; or a pharmaceutically acceptable salt thereof.

In another embodiment, the present invention provides a compound selected from the group consisting of the following Formulas II, III, IV, and V:

II

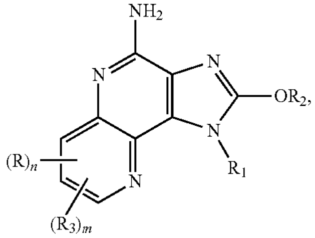

III

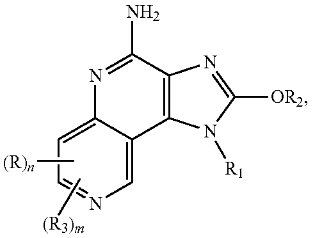

IV

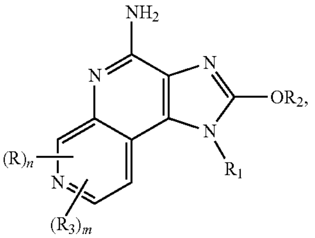

V

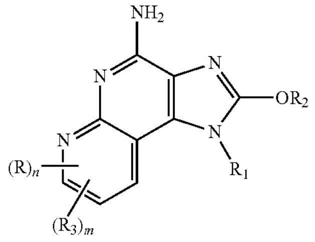

wherein:

$R_2$ is selected from the group consisting of hydrogen, $C_{1-4}$ alkyl, hydroxy$C_{2-4}$ alkylenyl, and $C_{1-4}$ alkoxy$C_{2-4}$ alkylenyl;

R is selected from the group consisting of:

halogen, hydroxy, alkyl, alkenyl, haloalkyl, alkoxy, alkylthio, and

—N($R_9$)$_2$;

n is an integer from 0 to 3;

$R_1$ is selected from the group consisting of:

hydrogen, $—CH(R_{11})—Ar$, $—CH(R_{11})—Ar'-R_4$, $—CH(R_{11})—Ar'-Y—R_4$, $—CH(R_{11})—Ar'-CH(R_{11})—Y—R_4$, $—CH(R_{11})—Ar'-R_5$, $—CH(R_{11})—Ar'-CH(R_{11})—R_5$, $—X_1$-Het, and $—X_1—N(R_9)$-Q-$R_4$;

Ar is selected from the group consisting of aryl and heteroaryl each of which is unsubstituted or substituted by one or more substituents independently selected from the group consisting of alkyl, alkenyl, alkoxy, methylenedioxy, haloalkyl, haloalkoxy, halogen, nitro, hydroxy, hydroxyalkyl, cyano, amino, alkylamino, and dialkylamino;

Ar' is selected from the group consisting of arylene and heteroarylene each of which is unsubstituted or substituted by one or more substituents independently selected from the group consisting of alkyl, alkenyl, alkoxy, haloalkyl, haloalkoxy, halogen, nitro, hydroxy, hydroxyalkyl, cyano, amino, alkylamino, and dialkylamino;

Het is heterocyclyl which is unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;

$X_1$ is $C_{1-6}$ alkylene that is optionally interrupted by one or more —O— groups;

$R_{11}$ is selected from the group consisting of hydrogen and $C_{1-3}$ alkylene;

$R_3$ is selected from the group consisting of:

$—Z—R_4$, $—Z—X—R_4$, $—Z—X—Y—R_4$, $—Z—X—Y—X—Y—R_4$, and $—Z—X—R_5$;

m is 0 or 1; with the proviso that when m is 1, then n is 0 or 1;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:

—O—, $—S(O)_{0-2}—$, $—S(O)_2—N(R_8)—$, $—C(R_6)—$, $—C(R_6)—O—$, $—O—C(R_6)—$,

—O—C(O)—O—, $—N(R_8)$-Q-, $—C(R_6)—N(R_8)—$, $—O—C(R_6)—N(R_8)—$, $C(R_6)—N(OR_9)—$, $—O—N(R_8)$-Q-, $—O—N{=}C(R_4)—$, $—C(=N—O—R_8)—$, $—CH(—N(—O—R_8)$-Q-$R_4)—$,

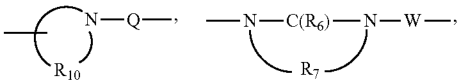

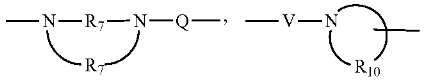

, and

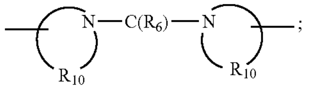

;

Z is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;

$R_5$ is selected from the group consisting of:

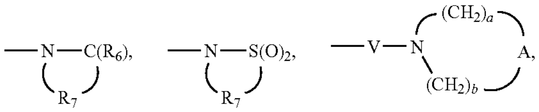

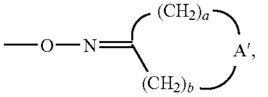

and

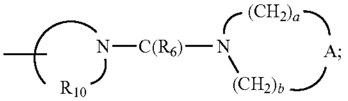

;

$R_6$ is selected from the group consisting of =O and =S;

$R_7$ is $C_{2-7}$ alkylene;

$R_8$ is selected from the group consisting of hydrogen, $C_{1-10}$ alkyl, $C_{2-10}$ alkenyl, hydroxy-$C_{1-10}$ alkylenyl, $C_{1-10}$ alkoxy-$C_{1-10}$ alkylenyl, aryl-$C_{1-10}$ alkylenyl, and heteroaryl-$C_{1-10}$ alkylenyl;

$R_9$ is selected from the group consisting of hydrogen and alkyl;

$R_{10}$ is $C_{3-8}$ alkylene;

A is selected from the group consisting of $—CH_2—$, —O—, —C(O)—, $—S(O)_{0-2}—$, and $—N(\text{-Q-}R_4)—$;

A' is selected from the group consisting of —O—, $—S(O)_{0-2}—$, $—N(\text{-Q-}R_4)—$, and $—CH_2—$;

Q is selected from the group consisting of a bond, $—C(R_6)—$, $—C(R_6)—C(R_6)—$, $—S(O)_2—$, $—C(R_6)—N(R_8)—W—$, $—S(O)_2—N(R_8)—$, $—C(R_6)—O—$, $—C(R_6)—S—$, and $—C(R_6)—N(OR_9)—$;

V is selected from the group consisting of $—C(R_6)—$, $—O—C(R_6)—$, $—N(R_8)—C(R_6)—$, and $—S(O)_2—$;

W is selected from the group consisting of a bond, —C(O)—, and $—S(O)_2—$; and a and b are independently integers from 1 to 6 with the proviso that a+b is ≦7; or a pharmaceutically acceptable salt thereof.

In another embodiment, the present invention provides a compound selected from the group consisting of the following Formulas VI, VII, VIII, and IX:

VI

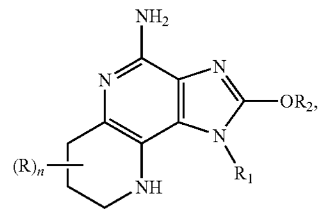

VII

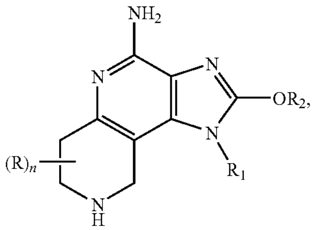

VIII

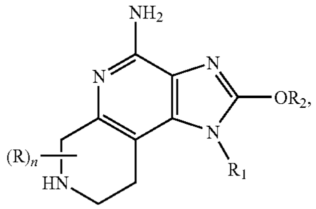

IX

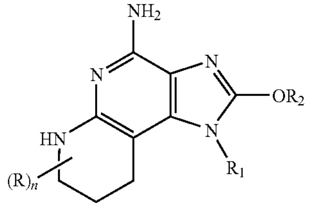

wherein:

$R_2$ is selected from the group consisting of hydrogen, $C_{1-4}$ alkyl, hydroxy$C_{2-4}$ alkylenyl, and $C_{1-4}$ alkoxy$C_{2-4}$ alkylenyl;

R is selected from the group consisting of:

halogen, hydroxy, alkyl, alkenyl, haloalkyl, alkoxy, alkylthio, and $—N(R_9)_2$;

n is an integer from 0 to 3;

$R_1$ is selected from the group consisting of:

hydrogen, $—CH(R_{11})—Ar$, $—CH(R_{11})—Ar'-R_4$, $—CH(R_{11})—Ar'-Y—R_4$, $—CH(R_{11})—Ar'-CH(R_{11})—Y—R_4$, $—CH(R_{11})—Ar'-R_5$, $—CH(R_{11})—Ar'-CH(R_{11})—R_5$, $—X_1$-Het, and $—X_1—N(R_8)-Q-R_4$;

Ar is selected from the group consisting of aryl and heteroaryl each of which is unsubstituted or substituted by one or more substituents independently selected from the group consisting of alkyl, alkenyl, alkoxy, methylenedioxy, haloalkyl, haloalkoxy, halogen, nitro, hydroxy, hydroxyalkyl, cyano, amino, alkylamino, and dialkylamino;

Ar' is selected from the group consisting of arylene and heteroarylene each of which is unsubstituted or substituted by one or more substituents independently selected from the group consisting of alkyl, alkenyl, alkoxy, haloalkyl, haloalkoxy, halogen, nitro, hydroxy, hydroxyalkyl, cyano, amino, alkylamino, and dialkylamino;

Het is heterocyclyl which is unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;

$X_1$ is $C_{1-6}$ alkylene that is optionally interrupted by one or more —O— groups;

$R_{11}$ is selected from the group consisting of hydrogen and $C_{1-3}$ alkylene;

Y is selected from the group consisting of:

—O—, $—S(O)_{0-2}—$, $—S(O)_2—N(R_8)—$, $—C(R_6)—$, $—C(R_6)—O—$, $—O—C(R_6)—$,

—O—C(O)—O—, $—N(R_8)-Q-$, $—C(R_6)—N(R_8)—$, $—O—C(R_6)—N(R_8)—$, $—C(R_6)—N(OR_9)—$, $—O—N(R_8)-Q-$, $—O—N{=}C(R_4)—$, $—C({=}N—O—R_8)—$, $—CH(—N(—O—R_8)-Q-R_4)—$,

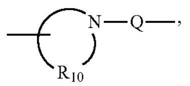

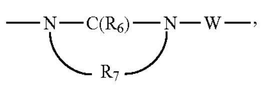

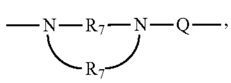

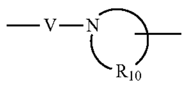

, and

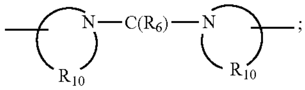

;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy;

heterocyclyl; amino; alkylamino; dialkylamino; (dialkylamino)alkyleneoxy; and, in the case of alkyl, alkenyl, alkynyl, and heterocyclyl, oxo;

$R_5$ is selected from the group consisting of:

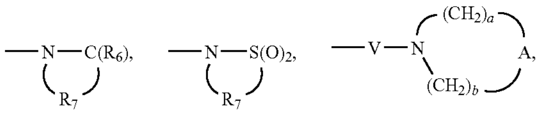

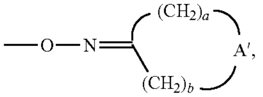

and

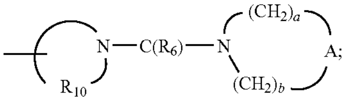

$R_6$ is selected from the group consisting of $=O$ and $=S$;

$R_7$ is $C_{2-7}$ alkylene;

$R_8$ is selected from the group consisting of hydrogen, $C_{1-10}$ alkyl, $C_{2-10}$ alkenyl, hydroxy-$C_{1-10}$ alkylenyl, $C_{1-10}$ alkoxy-$C_{1-10}$ alkylenyl, aryl-$C_{1-10}$ alkylenyl, and heteroaryl-$C_{1-10}$ alkylenyl;

$R_9$ is selected from the group consisting of hydrogen and alkyl;

$R_{10}$ is $C_{3-8}$ alkylene;

A is selected from the group consisting of $-CH_2-$, $-O-$, $-C(O)-$, $-S(O)_{0-2}-$, and $-N(-Q-R_4)-$;

A' is selected from the group consisting of $-O-$, $-S(O)_{0-2}-$, $-N(-Q-R_4)-$, and $-CH_2-$;

Q is selected from the group consisting of a bond, $-C(R_6)-$, $-C(R_6)-C(R_6)-$, $-S(O)_2-$, $-C(R_6)-N(R_8)-W-$, $-S(O)_2-N(R_8)-$, $-C(R_6)-O-$, $-C(R_6)-S-$, and $-C(R_6)-N(OR_9)-$;

V is selected from the group consisting of $-C(R_6)-$, $-O-C(R_6)-$, $-N(R_8)-C(R_6)-$, and $-S(O)_2-$;

W is selected from the group consisting of a bond, $-C(O)-$, and $-S(O)_2-$; and a and b are independently integers from 1 to 6 with the proviso that a+b is $\leqq 7$; or a pharmaceutically acceptable salt thereof.

In another embodiment, the present invention provides a compound of the following Formula X, which is a prodrug:

X

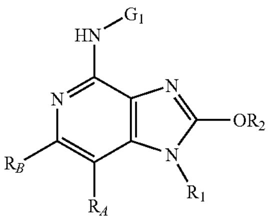

wherein:

$G_1$ is selected from the group consisting of:

$-C(O)-R'$,

α-aminoacyl,

α-aminoacyl-α-aminoacyl, $-C(O)-O-R'$, $-C(O)-N(R'')R'$, $-C(=NY')-R'$, $-CH(OH)-C(O)-OY'$, $-CH(OC_{1-4}\ alkyl)Y_0$, $-CH_2Y_1$, and $-CH(CH_3)Y_1$;

R' and R'' are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, $-O-C(O)-CH_3$, $-C(O)-O-CH_3$, $-C(O)-NH_2$, $-O-CH_2-C(O)-NH_2$, $-NH_2$, and $-S(O)_2-NH_2$, with the proviso that R'' can also be hydrogen;

α-aminoacyl is an α-aminoacyl group derived from an amino acid selected from the group consisting of racemic, D-, and L-amino acids;

Y' is selected from the group consisting of hydrogen, $C_{1-6}$ alkyl, and benzyl;

$Y_0$ is selected from the group consisting of $C_{1-6}$ alkyl, carboxy-$C_{1-6}$ alkylenyl, amino-$C_{1-4}$ alkylenyl, mono-N—$C_{1-6}$ alkylamino-$C_{1-4}$alkylenyl, and di-N,N—$C_{1-6}$ alkylamino-$C_{1-4}$alkylenyl;

$Y_1$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$ alkylpiperazin-1-yl;

$R_2$ is selected from the group consisting of hydrogen, $C_{1-4}$ alkyl, hydroxy$C_{2-4}$ alkylenyl, and $C_{1-4}$ alkoxy$C_{2-4}$ alkylenyl;

$R_A$ and $R_B$ taken together form a fused pyridine ring that is unsubstituted or substituted by one $R_3$ group, or substituted by one $R_3$ group and one R group, or substituted by one or more R groups;

or $R_A$ and $R_B$ taken together form a fused tetrahydropyridine ring that is unsubstituted or substituted by one or more R groups;

R is selected from the group consisting of:

halogen, hydroxy, alkyl, alkenyl, haloalkyl, alkoxy, alkylthio, and $-N(R_9)_2$;

$R_1$ is selected from the group consisting of:

hydrogen, $-CH(R_{11})-Ar$, $-CH(R_{11})-Ar'-R_4$, $-CH(R_{11})-Ar'-Y-R_4$, $-CH(R_{11})-Ar'-CH(R_{11})-Y-R_4$, $-CH(R_{11})-Ar'-R_5$, $-CH(R_{11})-Ar'-CH(R_{11})-R_5$, $-X_1$-Het, and $-X_1-N(R_8)$-Q-$R_4$;

Ar is selected from the group consisting of aryl and heteroaryl each of which is unsubstituted or substituted by one or more substituents independently selected from the group consisting of alkyl, alkenyl, alkoxy, methylenedioxy, haloalkyl, haloalkoxy, halogen, nitro, hydroxy, hydroxyalkyl, cyano, amino, alkylamino, and dialkylamino;

Ar' is selected from the group consisting of arylene and heteroarylene each of which is unsubstituted or substituted by one or more substituents independently selected from the group consisting of alkyl, alkenyl, alkoxy, haloalkyl, haloalkoxy, halogen, nitro, hydroxy, hydroxyalkyl, cyano, amino, alkylamino, and dialkylamino;

Het is heterocyclyl which is unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;

$X_1$ is $C_{1-6}$ alkylene that is optionally interrupted by one or more —O— groups;

$R_{11}$ is selected from the group consisting of hydrogen and $C_{1-3}$ alkylene;

$R_3$ is selected from the group consisting of:

—Z—$R_4$,

—Z—X—$R_4$,

—Z—X—Y—$R_4$,

—Z—X—Y—X—Y—$R_4$, and

—Z—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:

—O—,

—$S(O)_{0-2}$—,

—$S(O)_2$—N($R_8$)—,

—C($R_6$)—,

—C($R_6$)—O—,

—O—C($R_6$)—,

—O—C(O)—O—,

—N($R_8$)-Q-,

—C($R_6$)—N($R_8$)—,

—O—C($R_6$)—N($R_8$)—,

—C($R_6$)—N($OR_9$)—,

—O—N($R_8$)-Q-,

—O—N═C($R_4$)—,

—C(═N—O—$R_8$)—,

—CH(—N(—O—$R_8$)-Q-$R_4$)—,

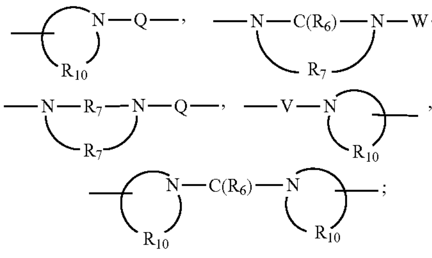

and

Z is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;

$R_5$ is selected from the group consisting of:

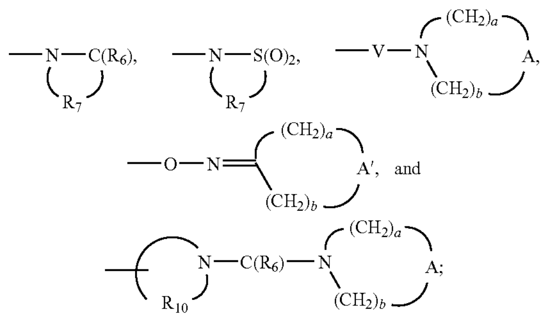

and $R_6$ is selected from the group consisting of ═O and ═S;

$R_7$ is $C_{2-7}$ alkylene;

$R_8$ is selected from the group consisting of hydrogen, $C_{1-10}$ alkyl, $C_{2-10}$ alkenyl, hydroxy-$C_{1-10}$ alkylenyl, $C_{1-10}$ alkoxy-$C_{1-10}$ alkylenyl, aryl-$C_{1-10}$ alkylenyl, and heteroaryl-$C_{1-10}$ alkylenyl;

$R_9$ is selected from the group consisting of hydrogen and alkyl;

$R_{10}$ is $C_{3-8}$ alkylene;

A is selected from the group consisting of —$CH_2$—, —O—, —C(O)—, —$S(O)_{0-2}$—, and —N(-Q-$R_4$)—;

A' is selected from the group consisting of —O—, —$S(O)_{0-2}$—, —N(-Q-$R_4$)—, and —$CH_2$—;

Q is selected from the group consisting of a bond, —C($R_6$)—, —C($R_6$)—C($R_6$)—, —$S(O)_2$—, —C($R_6$)—N($R_8$)—W—, —$S(O)_2$—N($R_8$)—, —C($R_6$)—O—, —C($R_6$)—S—, and —C($R_6$)—N($OR_9$)—;

V is selected from the group consisting of —C($R_6$)—, —O—C($R_6$)—, —N($R_8$)—C($R_6$)—, and —$S(O)_2$—;

W is selected from the group consisting of a bond, —C(O)—, and —$S(O)_2$—; and a and b are independently integers from 1 to 6 with the proviso that a+b is ≦7; or a pharmaceutically acceptable salt thereof.

In another embodiment, the present invention provides a compound of the following Formula XI, which is a prodrug:

XI

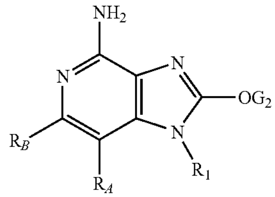

wherein:

$G_2$ is selected from the group consisting of:

—$X_2$—C(O)—R',

α-aminoacyl,

α-aminoacyl-α-aminoacyl,

—$X_2$—C(O)—O—R',

—C(O)—N(R")R', and

—$S(O)_2$—R';

$X_2$ is selected from the group consisting of a bond; —$CH_2$—O—; —$CH(CH_3)$—O—; —$C(CH_3)_2$—O—; and, in the case of —$X_2$—C(O)—O—R', —$CH_2$—NH—;

R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —$S(O)_2$—$NH_2$, with the proviso that R" can also be hydrogen;

α-aminoacyl is an α-aminoacyl group derived from an amino acid selected from the group consisting of racemic, D-, and L-amino acids;

$R_A$ and $R_B$ taken together form a fused pyridine ring that is unsubstituted or substituted by one $R_3$ group, or substituted by one $R_3$ group and one R group, or substituted by one or more R groups;

or $R_A$ and $R_B$ taken together form a fused tetrahydropyridine ring that is unsubstituted or substituted by one or more R groups;

R is selected from the group consisting of:

halogen, hydroxy, alkyl, alkenyl, haloalkyl, alkoxy, alkylthio, and

—$N(R_9)_2$;

$R_1$ is selected from the group consisting of:

hydrogen,

—$CH(R_{11})$—Ar,

—$CH(R_{11})$—Ar'-$R_4$,

—$CH(R_{11})$—Ar'-Y—$R_4$,

—$CH(R_{11})$—Ar'-$CH(R_{11})$—Y—$R_4$,

—$CH(R_{11})$—Ar'-$R_5$,

—$CH(R_{11})$—Ar'-$CH(R_{11})$—$R_5$, —$X_1$-Het, and

—$X_1$—$N(R_8)$-Q-$R_4$;

Ar is selected from the group consisting of aryl and heteroaryl each of which is unsubstituted or substituted by one or more substituents independently selected from the group consisting of alkyl, alkenyl, alkoxy, methylenedioxy, haloalkyl, haloalkoxy, halogen, nitro, hydroxy, hydroxyalkyl, cyano, amino, alkylamino, and dialkylamino;

Ar' is selected from the group consisting of arylene and heteroarylene each of which is unsubstituted or substituted by one or more substituents independently selected from the group consisting of alkyl, alkenyl, alkoxy, haloalkyl, haloalkoxy, halogen, nitro, hydroxy, hydroxyalkyl, cyano, amino, alkylamino, and dialkylamino;

Het is heterocyclyl which is unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;

$X_1$ is $C_{1-6}$ alkylene that is optionally interrupted by one or more —O— groups;

$R_{11}$ is selected from the group consisting of hydrogen and $C_{1-3}$ alkylene;

$R_3$ is selected from the group consisting of:

—Z—$R_4$,

—Z—X—$R_4$,

—Z—X—Y—$R_4$,

—Z—X—Y—X—Y—$R_4$, and

—Z—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:

—O—,

—$S(O)_{0-2}$—,

—$S(O)_2$—$N(R_8)$—,

—$C(R_6)$—,

—$C(R_6)$—O—,

—O—$C(R_6)$—,

—O—C(O)—O—,

—$N(R_8)$-Q-,

—$C(R_6)$—$N(R_8)$—,

—O—$C(R_6)$—$N(R_8)$—,

—$C(R_6)$—$N(OR_9)$—,

—O—$N(R_8)$-Q-,

—O—N=$C(R_4)$—,

—C(=N—O—$R_5$)—,

—CH(—N(—O—$R_8$)-Q-$R_4$)—,

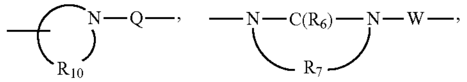

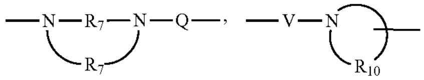

, and

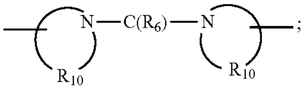

;

Z is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;

$R_5$ is selected from the group consisting of:

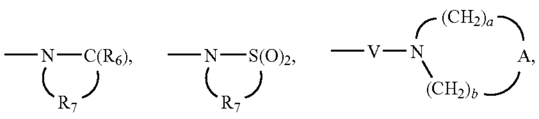

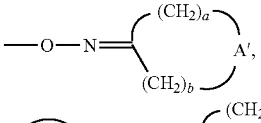

and

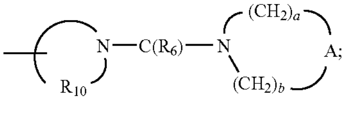

;

$R_6$ is selected from the group consisting of =O and =S;

$R_7$ is $C_{2-7}$ alkylene;

$R_8$ is selected from the group consisting of hydrogen, $C_{1-10}$ alkyl, $C_{2-10}$ alkenyl, hydroxy-$C_{1-10}$ alkylenyl, $C_{1-10}$ alkoxy-$C_{1-10}$ alkylenyl, aryl-$C_{1-10}$ alkylenyl, and heteroaryl-$C_{1-10}$ alkylenyl;

$R_9$ is selected from the group consisting of hydrogen and alkyl;

$R_{10}$ is $C_{3-8}$ alkylene;

A is selected from the group consisting of —$CH_2$—, —O—, —C(O)—, —$S(O)_{0-2}$—, and —N(-Q-$R_4$)—;

A' is selected from the group consisting of —O—, —$S(O)_{0-2}$—, —N(-Q-$R_4$)—, and —$CH_2$—;

Q is selected from the group consisting of a bond, —C($R_6$)—, —C($R_6$)—C($R_6$)—, —$S(O)_2$—, —C($R_6$)—N($R_8$)—W—, —$S(O)_2$—N($R_8$)—, —C($R_6$)—O—, —C($R_6$)—S—, and —C($R_6$)—N($OR_9$)—;

V is selected from the group consisting of —C($R_6$)—, —O—C($R_6$)—, —N($R_8$)—C($R_6$)—, and —$S(O)_2$—;

W is selected from the group consisting of a bond, —C(O)—, and —$S(O)_2$—; and a and b are independently integers from 1 to 6 with the proviso that a+b is ≦7; or a pharmaceutically acceptable salt thereof.

In another aspect, the present invention provides intermediate compound of the following Formula XIV:

XIV

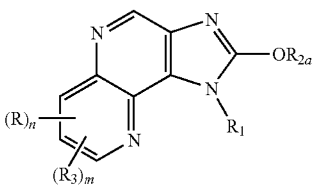

wherein:

$R_{2a}$ is selected from the group consisting of $C_{1-4}$ alkyl, hydroxy$C_{2-4}$ alkylenyl, $C_{1-4}$ alkoxy$C_{2-4}$ alkylenyl, and benzyl that is unsubstituted or substituted by one or two substituents selected from the group consisting of methyl, methoxy, chloro, and nitro;

R is selected from the group consisting of:

halogen, hydroxy, alkyl, alkenyl, haloalkyl, alkoxy, alkylthio, and

—N($R_9$)$_2$;

n is an integer from 0 to 3;

$R_1$ is selected from the group consisting of:

hydrogen,

—CH($R_{11}$)—Ar,

—CH($R_{11}$)—Ar'-$R_4$,

—CH($R_{11}$)—Ar'-Y—$R_4$,

—CH($R_{11}$)—Ar'-CH($R_{11}$)—Y—$R_4$,

—CH($R_{11}$)—Ar'-$R_5$,

—CH($R_{11}$)—Ar'-CH($R_{11}$)—$R_5$,

—$X_1$-Het, and

—$X_1$—N($R_8$)-Q-$R_4$;

Ar is selected from the group consisting of aryl and heteroaryl each of which is unsubstituted or substituted by one or more substituents independently selected from the group consisting of alkyl, alkenyl, alkoxy, methylenedioxy, haloalkyl, haloalkoxy, halogen, nitro, hydroxy, hydroxyalkyl, cyano, amino, alkylamino, and dialkylamino;

Ar' is selected from the group consisting of arylene and heteroarylene each of which is unsubstituted or substituted by one or more substituents independently selected from the group consisting of alkyl, alkenyl, alkoxy, haloalkyl, haloalkoxy, halogen, nitro, hydroxy, hydroxyalkyl, cyano, amino, alkylamino, and dialkylamino;

Het is heterocyclyl which is unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;

$X_1$ is $C_{1-6}$ alkylene that is optionally interrupted by one or more —O— groups;

$R_{11}$ is selected from the group consisting of hydrogen and $C_{1-3}$ alkylene;

$R_3$ is selected from the group consisting of:

—Z—$R_4$,

—Z—X—$R_4$,

—Z—X—Y—$R_4$,

—Z—X—Y—X—Y—$R_4$, and

—Z—X—$R_5$;

m is 0 or 1; with the proviso that when m is 1, then n is 0 or 1;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:

—O—,

—$S(O)_{0-2}$—,

—$S(O)_2$—N($R_8$)—,

—C($R_6$)—,

—C($R_6$)—O—,

—O—C($R_6$)—,

—O—C(O)—O—,

—N($R_8$)-Q-,

—C($R_6$)—N($R_8$)—,

—O—C($R_6$)—N($R_8$)—,

—C($R_6$)—N($OR_9$)—,

—O—N($R_8$)-Q-,

—O—N=C($R_4$)—,

—C(=N—O—$R_8$)—,

—CH(—N(—O—$R_5$)-Q-$R_4$)—,

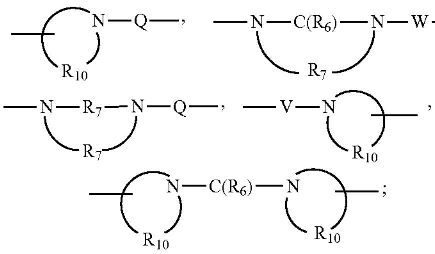

, and ;

Z is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;

$R_5$ is selected from the group consisting of:

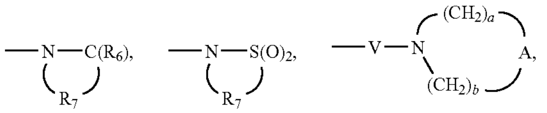

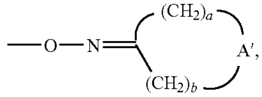

and

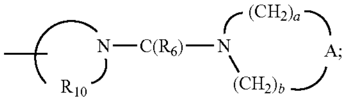

$R_6$ is selected from the group consisting of =O and =S;

$R_7$ is $C_{2-7}$ alkylene;

$R_8$ is selected from the group consisting of hydrogen, $C_{1-10}$ alkyl, $C_{2-10}$ alkenyl, hydroxy-$C_{1-10}$ alkylenyl, $C_{1-10}$ alkoxy-$C_{1-10}$ alkylenyl, aryl-$C_{1-10}$ alkylenyl, and heteroaryl-$C_{1-10}$ alkylenyl;

$R_9$ is selected from the group consisting of hydrogen and alkyl;

$R_{10}$ is $C_{3-8}$ alkylene;

A is selected from the group consisting of —$CH_2$—, —O—, —C(O)—, —$S(O)_{0-2}$—, and N(-Q-$R_4$)—;

A' is selected from the group consisting of —O—, —$S(O)_{0-2}$—, —N(-Q-$R_4$)—, and —$CH_2$—;

Q is selected from the group consisting of a bond, —C($R_6$)—, —C($R_6$)—C($R_6$)—, —$S(O)_2$—, —C($R_6$)—N($R_8$)—W—, —$S(O)_2$—N($R_8$)—, —C($R_6$)—O—, —C($R_6$)—S—, and —C($R_6$)—N($OR_9$)—;

V is selected from the group consisting of —C($R_6$)—, —O—C($R_6$)—, —N($R_8$)—C($R_6$)—, and —$S(O)_2$—;

W is selected from the group consisting of a bond, —C(O)—, and —$S(O)_2$—; and a and b are independently integers from 1 to 6 with the proviso that a+b is ≦7; or a pharmaceutically acceptable salt thereof.

For some embodiments, a compound selected from the group consisting of the Formulas II, III, IV, and V is of the Formula II:

II

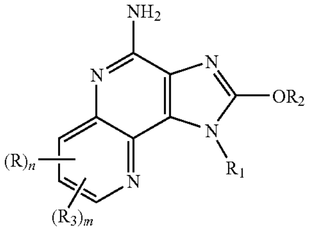

or a pharmaceutically acceptable salt thereof.

For some embodiments, a compound selected from the group consisting of the Formulas VI, VII, VIII, and IX is of the Formula VI:

VI

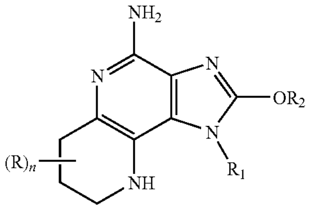

or a pharmaceutically acceptable salt thereof.

For certain embodiments of the compounds of Formulas I through IX, the —$NH_2$ group can be replaced by an —NH-$G_1$ group, as shown in the compound of Formula X, to form prodrugs. For certain of these embodiments, the resulting compound is of the Formula XII:

XII

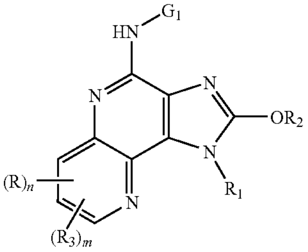

wherein:

n is an integer from 0 to 3;

m is 0 or 1; with the proviso that when m is 1, then n is 0 or 1;

R, $R_1$, $R_2$, and $R_3$ are as defined above for a compound of Formula II; and $G_1$ is as defined above for a compound of Formula X; or a pharmaceutically acceptable salt thereof.

For certain embodiments of the compounds of Formulas I through IX, the —$R_2$ group can be replaced by a -$G_2$ group, as shown in the compound of Formula XI, to form prodrugs. For certain of these embodiments, the resulting compound is of the Formula XIII:

XIII

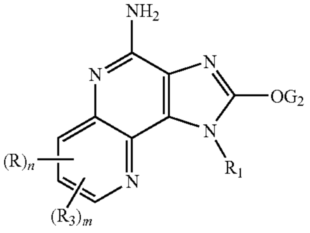

wherein:

n is an integer from 0 to 3;

m is 0 or 1; with the proviso that when m is 1, then n is 0 or 1;

R, $R_1$, $R_2$, and $R_3$ are as defined above for a compound of Formula II; and $G_2$ is as defined above for a compound of Formula XI; or a pharmaceutically acceptable salt thereof.

For any of the compounds presented herein, each one of the following variables (e.g., $R_1$, $R_2$, $G_1$, $G_2$, $R_4$, $R_{11}$, X, $X_1$, Y, $Y_1$, A, Q, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments, e.g., of Formula X and XII, $G_1$ is selected from the group consisting of —C(O)—R', α-aminoacyl, α-aminoacyl-α-aminoacyl, —C(O)—O—R', —C(O)—N(R")R', —C(=NY')—R', —CH(OH)—C(O)—OY', —CH(OC$_{1-4}$ alkyl)$Y_0$, —$CH_2Y_1$, and —CH($CH_3$)$Y_1$. For certain of these embodiments, R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —S(O)$_2$—$NH_2$, with the proviso that R" can also be hydrogen;

α-aminoacyl is an α-aminoacyl group derived from an amino acid selected from the group consisting of racemic, D-, and L-amino acids;

Y' is selected from the group consisting of hydrogen, $C_{1-6}$ alkyl, and benzyl;

$Y_0$ is selected from the group consisting of $C_{1-6}$ alkyl, carboxy-$C_{1-6}$ alkylenyl, amino-$C_{1-4}$ alkylenyl, mono-N—$C_{1-6}$ alkylamino-$C_{1-4}$ alkylenyl, and di-N,N—$C_{1-6}$ alkylamino-$C_{1-4}$ alkylenyl; and $Y_1$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$ alkylpiperazin-1-yl.

For certain embodiments, including any one of the above embodiments of Formula X and XII, $G_1$ is selected from the group consisting of —C(O)—R', α-aminoacyl, and —C(O)—O—R'.

For certain embodiments, including any one of the above embodiments of Formula X and XII, $G_1$ is selected from the group consisting of —C(O)—R', α-amino-$C_{2-11}$ acyl, and —C(O)—O—R', α-Amino-$C_{2-11}$ acyl includes α-amino acids containing a total of at least 2 carbon atoms and a total of up to 11 carbon atoms, and may also include one or more heteroatoms selected from the group consisting of O, S, and N.

For certain embodiments, e.g., of Formula XI and XIII, $G_2$ is selected from the group consisting of —$X_2$—C(O)—R', α-aminoacyl, α-aminoacyl-α-aminoacyl, —$X_2$—C(O)—O—R', C(O)—N(R")R', and —S(O)$_2$—R'. For certain of these embodiments, $X_2$ is selected from the group consisting of a bond; —$CH_2$—O—; —CH($CH_3$)—O—; —C($CH_3$)$_2$—O—; and, in the case of —$X_2$—C(O)—O—R', —$CH_2$—NH—;

R' and R" are independently selected from the group consisting of $C_{10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —S(O)$_2$—$NH_2$, with the proviso that R" can also be hydrogen; and α-aminoacyl is an α-aminoacyl group derived from an amino acid selected from the group consisting of racemic, D-, and L-amino acids.

For certain embodiments, including any one of the above embodiments which include an α-aminoacyl group, α-aminoacyl is an α-aminoacyl group derived from a naturally occurring amino acid selected from the group consisting of racemic, D-, and L-amino acids.

For certain embodiments, including any one of the above embodiments which include an α-aminoacyl group, α-aminoacyl is an α-aminoacyl group derived from an amino acid found in proteins, wherein the amino acid is selected from the group consisting of racemic, D-, and L-amino acids.

For certain embodiments, including any one of the above embodiments of Formula XI and XIII, $G_2$ is selected from the group consisting of α-amino-$C_{2-5}$ alkanoyl, $C_{2-6}$ alkanoyl, $C_{1-6}$ alkoxycarbonyl, and $C_{1-6}$ alkylcarbamoyl.

For certain embodiments, the $R_2$ group of Formula X is replaced by $G_2$, wherein $G_2$ is defined as in any one of the above embodiments containing $G_2$.

For certain embodiments, e.g., of Formula I, X, and XI, $R_A$ and $R_B$ taken together form a fused pyridine ring that is unsubstituted or substituted by one $R_3$ group, or substituted by one $R_3$ group and one R group, or substituted by one or more R groups; or $R_A$ and $R_B$ taken together form a fused tetrahydropyridine ring that is unsubstituted or substituted by one or more R groups.

For certain embodiments, including any one of the above embodiments of Formula I, X, and XI, $R_A$ and $R_B$ taken together form a fused pyridine ring that is unsubstituted or substituted by one $R_3$ group, or substituted by one $R_3$ group and one R group, or substituted by one or more R groups. In certain of these embodiments, the pyridine ring is

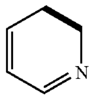

wherein the highlighted bond indicates the position where the ring is fused. In certain embodiments, $R_A$ and $R_B$ taken together form a fused pyridine ring that is unsubstituted.

For certain embodiments, including any one of the above embodiments of Formula I, X, and XI, $R_A$ and $R_B$ taken together form a fused tetrahydropyridine ring that is unsubstituted or substituted by one or more R groups. In certain of these embodiments, the ring is

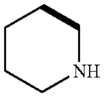

wherein the highlighted bond indicates the position where the ring is fused. In certain embodiments, $R_A$ and $R_B$ taken together form a fused tetrahydropyridine ring that is unsubstituted.

For certain embodiments, including any one of the above embodiments of Formula I, II, III, IV, V, VI, VII, VIII, IX, X, XI, XII, XIII, and XIV, $R_1$ is selected from the group consisting of hydrogen, —CH($R_{11}$)—Ar, —CH($R_{11}$)—Ar'—$R_4$, —CH($R_{11}$)—Ar'-Y—$R_4$, —CH($R_{11}$)—Ar'-CH($R_1$)—Y—

$R_4$, —CH($R_{11}$)—Ar'—$R_5$, —CH($R_{11}$)—Ar'-CH($R_{11}$)—$R_5$, —$X_1$-Het, and —$X_1$—N($R_8$)-Q-$R_4$.

For certain embodiments, including any one of the above embodiments of Formula I, II, III, IV, V, VI, VII, VIII, IX, X, XI, XII, XIII, and XIV, $R_1$ is —CH($R_{11}$)—Ar. For certain of these embodiments, $R_1$ is selected from the group consisting of benzyl, 1-phenylethyl, and pyridinylmethyl, each of which is unsubstituted or substituted by one or more substituents independently selected from the group consisting of alkyl, alkoxy, haloalkyl, haloalkoxy, and halogen. For certain of these embodiments, $R_1$ is selected from the group consisting of benzyl, 4-methoxybenzyl, 1-phenylethyl, and pyridin-3-ylmethyl. For certain of these embodiments, $R_1$ is selected from the group consisting of benzyl and 1-phenylethyl.

For certain embodiments, including any one of the above embodiments of Formula I through XIV, $R_1$ is —CH($R_{11}$)—Ar'-CH($R_{11}$)—Y—$R_4$, except where $R_1$ is —CH($R_{11}$)—Ar. For certain of these embodiments, each $R_{11}$ is hydrogen; Ar' is phenylene; Y in —CH($R_{11}$)—Ar'-CH($R_{11}$)—Y—$R_4$ is —NHQ- wherein Q is selected from the group consisting of —C(O)—, —S(O)$_2$—, —C($R_6$)—N($R_8$)—, —S(O)$_2$—N($R_8$)—, —C(O)—O—, and —C(O)—S—; and $R_4$ in —CH($R_{11}$)—Ar'-CH($R_{11}$)—Y—$R_4$ is selected from the group consisting of alkyl, aryl, heteroaryl, heterocyclyl, and arylalkylenyl wherein alkyl, aryl, and heteroaryl are each unsubstituted or substituted by one or more substituents independently selected from the group consisting of alkyl, alkoxy, and halogen.

For certain embodiments, including any one of the above embodiments of Formula I through XIV, $R_1$ is —CH($R_{11}$)—Ar'-CH($R_{11}$)—$R_5$, except where $R_1$ is —CH($R_{11}$)—Ar or —CH($R_{11}$)—Ar'-CH($R_{11}$)—Y—$R_4$. For certain of these embodiments, each $R_{11}$ is hydrogen; Ar' is phenylene; and $R_5$ in —CH($R_{11}$)—Ar'-CH($R_{11}$)—$R_5$ is

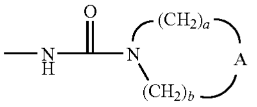

wherein A is selected from the group consisting of —$CH_2$—, —O—, and —N(alkyl)-, and a and b are each independently 1, 2, or 3.

For certain embodiments, including any one of the above embodiments of Formula I through XIV, $R_1$ is —$X_1$—N($R_8$)-Q-$R_4$, except where $R_1$ is —CH($R_{11}$)—Ar, —CH($R_{11}$)—Ar'-CH($R_{11}$)—Y—$R_4$, or —CH($R_{11}$)—Ar'-CH($R_{11}$)—$R_5$. For certain of these embodiments, XI is $C_{1-4}$ alkylene; $R_8$ in —$X_1$—N($R_8$)-Q-$R_4$ is hydrogen; Q in —$X_1$—N($R_8$)-Q-$R_4$ is selected from the group consisting of —C(O)—, —S(O)$_2$—, —C($R_6$)—N($R_8$)—, and —S(O)$_2$—N($R_8$)—; and $R_4$ in —$X_1$—N($R_8$)-Q-$R_4$ is selected from the group consisting of alkyl, aryl, heteroaryl, heterocyclyl, and arylalkylenyl wherein alkyl, aryl, and heteroaryl are each unsubstituted or substituted by one or more substituents independently selected from the group consisting of alkyl, alkoxy, and halogen. Alternatively, for certain of these embodiments, XI is $C_{1-4}$ alkylene; $R_8$ in —$X_1$—N($R_8$)-Q-$R_4$ is $C_{1-10}$ alkyl or hydroxy-$C_{1-10}$ alkylenyl; Q in —$X_1$—N($R_8$)-Q-$R_4$ is a bond; and $R_4$ in —$X_1$—N($R_8$)-Q-$R_4$ is selected from the group consisting of alkyl, aryl, arylalkylenyl, and heteroarylalkylenyl wherein alkyl is optionally substituted by one or more substituents independently selected from the group consisting of alkoxy and hydroxy.

For certain embodiments, including any one of the above embodiments of Formula I through XIV, $R_1$ is —$X_1$-Het, except where $R_1$ is —CH($R_{11}$)—Ar, —CH($R_{11}$)—Ar'-CH($R_{11}$)—Y—$R_4$, —CH($R_{11}$)—Ar'-CH($R_{11}$)—$R_5$, or —$X_1$—N($R_8$)-Q-$R_4$. For certain of these embodiments Het is selected from the group consisting of piperidinyl, piperazinyl, morpholinyl, thiomorpholinyl, azepanyl, and dihydroisoquinolin-(1H)-yl each of which is optionally substituted by one or more substituents independently selected from the group consisting of alkyl and hydroxy.

For certain embodiments, including any one of the above embodiments of Formula I, II, III, IV, V, VI, VII, VIII, IX, X, XI, XII, XIII, and XIV wherein $R_1$ can be —$X_1$-Het, $R_1$ is tetrahydropyranylmethyl. For certain of these embodiments, $R_1$ is tetrahydro-2H-pyran-4-ylmethyl.

For certain embodiments, including any one of the above embodiments of Formula I, II, III, IV, V, VI, VII, VIII, IX, X, and XII, $R_2$ is selected from the group consisting of hydrogen, $C_{1-4}$ alkyl, hydroxy$C_{2-4}$ alkylenyl, and $C_{1-4}$ alkoxy$C_{2-4}$ alkylenyl.

For certain embodiments, including any one of the above embodiments of Formula I, II, III, IV, V, VI, VII, VIII, IX, X, and XII, $R_2$ is hydrogen.

For certain embodiments, including any one of the above embodiments of Formula XIV, $R_{2a}$ is selected from the group consisting of $C_{1-4}$ alkyl, hydroxy$C_{2-4}$ alkylenyl, $C_{1-4}$ alkoxy$C_{2-4}$ alkylenyl, and benzyl that is unsubstituted or substituted by one or two substituents selected from the group consisting of methyl, methoxy, chloro, and nitro.

For certain embodiments, including any one of the above embodiments of Formula I, II, III, IV, V, VI, VII, VIII, IX, X, XI, XII, XIII, and XIV, $R_3$ is selected from the group consisting of —Z—$R_4$, —Z—X—$R_4$, —Z—X—Y—$R_4$, —Z—X—Y—X—Y—$R_4$, and —Z—X—$R_5$.

For certain embodiments, including any one of the above embodiments of Formula I, II, III, IV, V, VI, VII, VIII, IX, X, XI, XII, XIII, and XIV, $R_3$ is pyridin-3-yl, 3-hydroxyphenyl, 4-hydroxymethylphenyl, or benzyloxy. For certain of these embodiments, $R_3$ is pyridin-3-yl or benzyloxy.

For certain embodiments, including any one of the above embodiments of Formula II, III, IV, V, VI, VII, VIII, IX, XII, XIII, and XIV, $R_3$ is at the 7-position.

For certain embodiments, including any one of the above embodiments of Formula I, II, III, IV, V, VI, VII, VIII, IX, X, XI, XII, XIII, and XIV, R is selected from the group consisting of halogen, hydroxy, alkyl, alkenyl, haloalkyl, alkoxy, alkylthio, and —N($R_9$)$_2$.

For certain embodiments, including any one of the above embodiments of Formula I, II, III, IV, V, VI, VII, VIII, IX, X, XI, XII, XIII, and XIV, R is hydroxy.

For certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo.

For certain embodiments, $R_4$ is selected from the group consisting of alkyl, aryl, heteroaryl, heterocyclyl, and arylalkylenyl wherein alkyl, aryl, and heteroaryl are each unsubstituted or substituted by one or more substituents independently selected from the group consisting of alkyl, alkoxy, and halogen.

For certain embodiments, $R_4$ is selected from the group consisting of alkyl, aryl, arylalkylenyl, and heteroarylalkylenyl wherein alkyl is optionally substituted by one or more substituents independently selected from the group consisting of alkoxy and hydroxy.

For certain embodiments, $R_5$ is selected from the group consisting of:

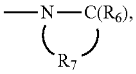,
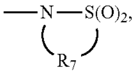,
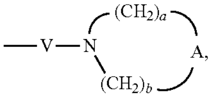,
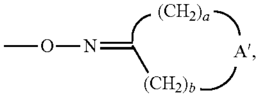, and
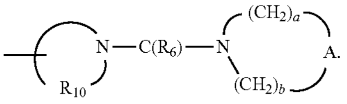.

For certain embodiments, $R_5$ is

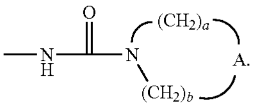.

For certain embodiments, $R_6$ is selected from the group consisting of =O and =S.

For certain embodiments, $R_6$ is =O. For certain embodiments, $R_6$ is =S.

For certain embodiments, $R_7$ is $C_{2-7}$ alkylene. For certain embodiments, $R_7$ is $C_{2-4}$ alkylene. For certain embodiments, $R_7$ is ethylene.

For certain embodiments, $R_8$ is selected from the group consisting of hydrogen, $C_{1-10}$ alkyl, $C_{2-10}$ alkenyl, hydroxy-$C_{1-10}$ alkylenyl, $C_{1-10}$ alkoxy-$C_{1-10}$ alkylenyl, aryl-$C_{1-10}$ alkylenyl, and heteroaryl-$C_{1-10}$ alkylenyl.

For certain embodiments, $R_8$ is hydrogen, $C_{1-10}$ alkyl, or hydroxy-$C_{1-10}$ alkylenyl.

For certain embodiments, $R_8$ is $C_{1-10}$ alkyl or hydroxy-$C_{1-10}$ alkylenyl.

For certain embodiments, $R_8$ is hydrogen.

For certain embodiments, $R_9$ is selected from the group consisting of hydrogen and alkyl.

For certain embodiments, $R_{10}$ is $C_{3-8}$ alkylene. For certain embodiments, $R_{10}$ is pentylene.

For certain embodiments, $R_{11}$ is selected from the group consisting of hydrogen and $C_{1-3}$ alkylene.

For certain embodiments, $R_{11}$ is methyl. For certain embodiments, $R_{11}$ is hydrogen.

For certain embodiments, R' is selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, $-O-C(O)-CH_3$, $-C(O)-O-CH_3$, $-C(O)-NH_2$, $-O-CH_2-C(O)-NH_2$, $-NH_2$, and $-S(O)_2-NH_2$.

For certain embodiments, R" is selected from the group consisting of hydrogen, $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, $-O-C(O)-CH_3$, $-C(O)-O-CH_3$, $-C(O)-NH_2$, $-O-CH_2-C(O)-NH_2$, $-NH_2$, and $-S(O)_2-NH_2$.

For certain embodiments, A is selected from the group consisting of $-CH_2-$, $-O-$, $C(O)-$, $-S(O)_{0-2}-$, and $-N(-Q-R_4)-$.

For certain embodiments, A is selected from the group consisting of $-CH_2-$, $-O-$, and $-N(alkyl)-$. For certain embodiments, A is $-O-$.

For certain embodiments, A' is selected from the group consisting of $-O-$, $-S(O)_{0-2}-$, $-N(-Q-R_4)-$, and $-CH_2-$.

For certain embodiments, Ar is selected from the group consisting of aryl and heteroaryl each of which is unsubstituted or substituted by one or more substituents independently selected from the group consisting of alkyl, alkenyl, alkoxy, methylenedioxy, haloalkyl, haloalkoxy, halogen, nitro, hydroxy, hydroxyalkyl, cyano, amino, alkylamino, and dialkylamino.

For certain embodiments, Ar is phenyl. For certain embodiments, Ar is pyridinyl.

For certain embodiments, Ar' is selected from the group consisting of arylene and heteroarylene each of which is unsubstituted or substituted by one or more substituents independently selected from the group consisting of alkyl, alkenyl, alkoxy, haloalkyl, haloalkoxy, halogen, nitro, hydroxy, hydroxyalkyl, cyano, amino, alkylamino, and dialkylamino. For certain embodiments, Ar' is phenylene.

For certain embodiments, Het is heterocyclyl which is unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo.

For certain embodiments, Het is heterocyclyl which is unsubstituted or substituted by one or more substituents independently selected from the group consisting of alkyl, alkoxy, haloalkyl, haloalkoxy, halogen, nitro, hydroxy, cyano, amino, alkylamino, dialkylamino, and oxo.

For certain embodiments, Het is selected from the group consisting of piperidinyl, piperazinyl, morpholinyl, thiomorpholinyl, azepanyl, and dihydroisoquinolin-(1H)-yl each of which is optionally substituted by one or more substituents independently selected from the group consisting of alkyl and hydroxy.

For certain embodiments, Het is tetrahydropyranyl.

For certain embodiments, Het is tetrahydro-2H-pyran-4-yl.

For certain embodiments, Q is selected from the group consisting of a bond, $C(R_6)-$, $-C(R_6)-C(R_6)-$, $-S(O)_2-$, $-C(R_6)-N(R_8)-W-$, $-S(O)_2-N(R_8)-$, $-C(R_6)-O-$, $-C(R_6)-S-$, and $-C(R_6)-N(OR_9)-$.

For certain embodiments, Q is selected from the group consisting of $-C(O)-$, $-S(O)_2-$, $-C(R_6)-N(R_8)-$, $-S(O)_2-N(R_8)-$, $-C(O)-O-$, and $-C(O)-S-$.

For certain embodiments, Q is $-C(O)-$, $-S(O)_2-$, $-C(R_6)-N(R_8)-$, and $-S(O)_2-N(R_8)-$.

For certain embodiments, Q is —$C(R_6)$—.

For certain embodiments, Q is a bond.

For certain embodiments, V is selected from the group consisting of —$C(R_6)$—, —O—$C(R_6)$—, —$N(R_8)$—C$(R_6)$—, and —$S(O)_2$—.

For certain embodiments, V is —$N(R_8)$—C(O)—. For certain embodiments, V is —N(H)—C(O)—.

For certain embodiments, W is selected from the group consisting of a bond, —C(O)—, and —$S(O)_2$—. For certain embodiments, W is a bond.

For certain embodiments, X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups.

For certain embodiments, X is $C_{1-4}$ alkylene. For certain embodiments, X is methylene.

For certain embodiments, XI is $C_{1-6}$ alkylene that is optionally interrupted by one or more —O— groups. For certain embodiments, XI is $C_{1-4}$ alkylene.

For certain embodiments, $X_2$ is selected from the group consisting of a bond; —$CH_2$—O—; —$CH(CH_3)$—O—; —$C(CH_3)_2$—O—; and, in the case of —$X_2$—C(O)—O—R', —$CH_2$—NH—.

For certain embodiments, Y is selected from the group consisting of —O—, —$S(O)_{0-2}$—, —$S(O)_2$—$N(R_8)$—, —$C(R_6)$—, —$C(R_6)$—O—, —O—$C(R_6)$—, —O—C(O)—O—, —$N(R_8)$-Q-, —$C(R_6)$—$N(R_8)$—, —O—$C(R_6)$—N$(R_8)$—, —$C(R_6)$—$N(OR_9)$—, —O—$N(R_8)$-Q-, —O—N=$C(R_4)$—, —C(=N—O—$R_8$)—, —CH(—N(—O—$R_8$)-Q-$R_4$)—,

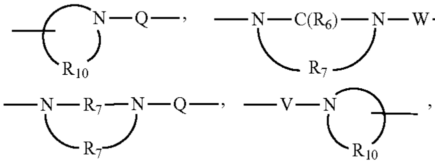, and

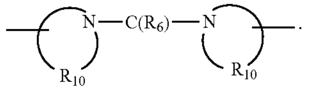.

For certain embodiments, Y is —$N(R_8)$-Q-.

For certain embodiments, Y is selected from the group consisting of —$N(R_8)$—C(O)—, —$N(R_8)$—$S(O)_2$—, —$N(R_8)$—$C(R_6)$—$N(R_8)$—, —$N(R_8)$—$S(O)_2$—$N(R_8)$—, —$N(R_8)$—$C(R_6)$—O—, and —$N(R_8)$—$C(R_6)$—S—.

For certain embodiments, Y is —NHQ-.

For certain embodiments, Y is selected from the group consisting of —N(H)—C(O)—, —N(H)—$S(O)_2$—, —N(H)—$C(R_6)$—$N(R_8)$—, —N(H)—$S(O)_2$—$N(R_8)$—, —N(H)—C(O)—O—, and —N(H)—C(O)—S—.

For certain embodiments, $Y_1$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$ alkylpiperazin-1-yl.

For certain embodiments, $Y_0$ is selected from the group consisting of $C_{1-6}$ alkyl, carboxy-$C_{1-6}$ alkylenyl, amino-$C_{1-4}$ alkylenyl, mono-N—$C_{1-6}$ alkylamino-$C_{1-4}$ alkylenyl, and di-N,N—$C_{1-6}$ alkylamino-$C_{1-4}$alkylenyl.

For certain embodiments, Y' is selected from the group consisting of hydrogen, $C_{1-6}$ alkyl, and benzyl.

For certain embodiments, Z is a bond or —O—.

For certain embodiments, Z is a bond. For certain embodiments, Z is —O—.

For certain embodiments, a and b are independently integers from 1 to 6 with the proviso that a+b is $\leqq 7$. For certain embodiments, a and b are each independently 1, 2, or 3. For certain embodiments, a and b are each 2.

For certain embodiments, m is 0 or 1; with the proviso that when m is 1, then n is 0 or 1.

For certain embodiments, m is 1, and n is 0 or 1.

For certain embodiments, m is 1, and n is 0.

For certain embodiments, n is an integer from 0 to 3.

For certain embodiments, n is 1.

For certain embodiments, including any one of the above embodiments of Formula II, III, IV, V, VI, VII, VIII, IX, XII, XIII, and XIV, n is 0, except where this definition of n is excluded.

For certain embodiments, including any one of the above embodiments of Formula II, III, IV, V, XII, XIII, and XIV, m is 0, except where this definition of m is excluded.

For certain embodiments, including any one of the above embodiments of Formula II, III, IV, V, XII, XIII, and XIV, m and n are both 0, except where this definition for m and n is excluded.

In one embodiment, the present invention provides the compound 4-amino-1-benzyl-1H-imidazo[4,5-c][1,5]naphthyridin-2-ol, or a pharmaceutically acceptable salt thereof. In one embodiment, the present invention provides the compound 4-amino-1-(1-phenylethyl)-1H-imidazo[4,5-c][1,5]naphthyridin-2-ol, or a pharmaceutically acceptable salt thereof. In one embodiment, the present invention provides the compound 4-amino-1-(4-methoxybenzyl)-1H-imidazo[4,5-c][1,5]naphthyridin-2-ol, or a pharmaceutically acceptable salt thereof. In one embodiment, the present invention provides the compound 4-amino-1-(pyridin-3-ylmethyl)-1H-imidazo[4,5-c][1,5]naphthyridin-2-ol, or a pharmaceutically acceptable salt thereof. In another embodiment, the present invention provides the compound 4-amino-1-(tetrahydro-2H-pyran-4-ylmethyl)-1H-imidazo[4,5-c][1,5]naphthyridin-2-ol, or a pharmaceutically acceptable salt thereof.

For certain embodiments, the present invention provides a pharmaceutical composition comprising a therapeutically effective amount of a compound or salt of any one of the above embodiments of Formulas I through XIII, and a pharmaceutically acceptable carrier.

For certain embodiments, the present invention provides a method of inducing cytokine biosynthesis in an animal comprising administering an effective amount of a compound or salt of any one of the above embodiments of Formulas I through XIII, or a pharmaceutical composition comprising an effective amount of a compound or salt of any one of the above embodiments of Formulas I through XIII to the animal. For certain of these embodiments, the cytokine is selected from the group consisting of IFN-α, TNF-α, IL-6, IL-10, and IL-12. For certain of these embodiments, the cytokine is IFN-α or TNF-α. For certain of these embodiments, the cytokine is IFN-α.

For certain embodiments, the present invention provides a method of treating a viral disease in an animal comprising administering a therapeutically effective amount of a compound or salt of any one of the above embodiments of Formulas I through XIII, or a pharmaceutical composition comprising a therapeutically effective amount of a compound or salt of any one of the above embodiments of Formulas I through XIII to the animal.

For certain embodiments, the present invention provides a method of treating a neoplastic disease in an animal comprising administering a therapeutically effective amount of a compound or salt of any one of the above embodiments of Formulas I through XIII, or a pharmaceutical composition comprising a therapeutically effective amount of a compound or salt of any one of the above embodiments of Formulas I through XIII to the animal.

As used herein, the terms “alkyl”, “alkenyl”, “alkynyl” and the prefix “alk-” are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclobutyl, cyclobutylmethyl, cyclopentyl, cyclopentylmethyl, cyclohexyl, cyclohexylmethyl, adamantyl, and substituted and unsubstituted bornyl, norbornyl, and norbornenyl.

Unless otherwise specified, “alkylene”, “-alkylene-”, “alkenylene”, “-alkenylene-”, “alkynylene”, and “-alkynylene-” are the divalent forms of the “alkyl”, “alkenyl”, and “alkynyl” groups defined above. The terms “alkylenyl”, “alkenylenyl”, and “alkynylenyl” are used when “alkylene”, “alkenylene”, and “alkynylene”, respectively, are substituted. For example, an arylalkylenyl group comprises an “alkylene” moiety to which an aryl group is attached.

The term “haloalkyl” is inclusive of alkyl groups that are substituted by one or more halogen atoms, including perfluorinated groups. This is also true of other groups that include the prefix “halo-”. Examples of suitable haloalkyl groups are chloromethyl, trifluoromethyl, and the like.

The term “aryl” as used herein includes carbocyclic aromatic rings or ring systems. Examples of aryl groups include phenyl, naphthyl, biphenyl, fluorenyl and indenyl.

Unless otherwise indicated, the term “heteroatom” refers to the atoms O, S, or N.

The term “heteroaryl” includes aromatic rings or ring systems that contain at least one ring heteroatom (e.g., O, S, N). In some embodiments, the term “heteroaryl” includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term “heterocyclyl” includes non-aromatic rings or ring systems that contain at least one ring heteroatom (e.g., O, S, N) and includes all of the fully saturated and partially unsaturated derivatives of the above mentioned heteroaryl groups. In some embodiments, the term “heterocyclyl” includes a ring or ring system that contains 2 to 12 carbon atoms, 1 to 3 rings, 1 to 4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term “heterocyclyl” includes bicyclic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When “heterocyclyl” contains a nitrogen atom, the point of attachment of the heterocyclyl group may be the nitrogen atom.

The terms “arylene”, “heteroarylene”, and “heterocyclylene” are the divalent forms of the “aryl”, “heteroaryl”, and “heterocyclyl” groups defined above. The terms, “arylenyl”, “heteroarylenyl”, and “heterocyclylenyl” are used when “arylene”, “heteroarylene,” and “heterocyclylene”, respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula

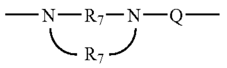

each $R_7$ group is independently selected. In another example, when more than one Y group is present, each Y group is independently selected. In a further example, when more than one —$N(R_8)$-Q-R group is present (e.g., more than one —Y—$R_4$ group is present, and both contain a —$N(R_8)$-Q- group) each $R_8$ group is independently selected, each Q group is independently selected, and each $R_4$ group is independently selected.

The invention is inclusive of the compounds described herein (including intermediates) in any of their pharmaceutically acceptable forms, including isomers (e.g., diastereomers and enantiomers), salts, solvates, polymorphs, prodrugs, and the like. In particular, if a compound is optically active, the invention specifically includes each of the compound’s enantiomers as well as racemic mixtures of the enantiomers. It should be understood that the term “compound” includes any or all of such forms, whether explicitly stated or not (although at times, “salts” are explicitly stated).

The term “prodrug” means a compound that can be transformed in vivo to yield an immune response modifying compound in any of the salt, solvated, polymorphic, or isomeric forms described above. The prodrug, itself, may be an immune response modifying compound in any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, “Pro-drugs as Novel Delivery Systems,” Vol. 14 of the A. C. S. Symposium Series, and in Bioreversible Carriers in Drug Design, ed. Edward B. Roche, American Pharmaceutical Association and Pergamon Press, 1987.

Compounds (including intermediates) of the present invention may exist in different tautomeric forms, and all such forms are embraced within the scope of the invention. The term “tautomer” or “tautomeric form” refers to structural isomers of different energies, which are interconvertible via a low energy barrier. For example, proton tautomers (prototropic tautomers) include interconversions via migration of a proton, such as keto-enol and imine-enamine isomerizations. When compounds of the present invention have a hydrogen atom for the $R_2$ group, proton migration between the oxygen atom at the 2-position and the 3-position may occur. For example, the following Formulas $I_a$ and $I_b$ are tautomeric forms of each other, and Formulas $X_a$ and $X_b$ are tautomeric forms of each other:

$I_a$

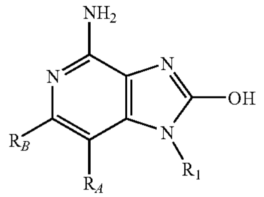

$I_b$

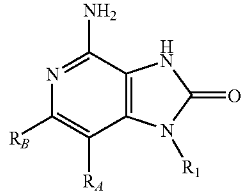

$X_a$

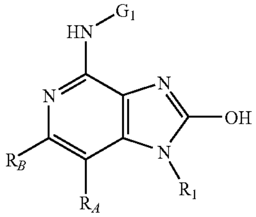

$X_b$

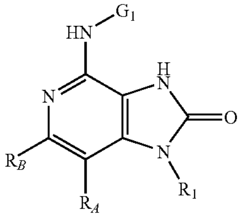

Preparation of the Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v. 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie,* 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

In the preparation of compounds of the invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, *Protective Groups in Organic Synthesis*, John Wiley & Sons, New York, USA, 1991.

Conventional methods and techniques of separation and purification can be used to isolate compounds of the invention, as well as various intermediates related thereto. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

For some embodiments, compounds of the invention can be prepared according to Reaction Scheme I, wherein R, $R_1$, and n are as defined above, and $R_{2b}$ is selected from the group consisting of $C_{1-4}$ alkyl, $C_{1-4}$ alkoxy$C_{2-4}$ alkylenyl, and benzyl that is unsubstituted or substituted by one or two substituents selected from the group consisting of methyl, methoxy, chloro, and nitro. In step (1) of Reaction Scheme I, a [1,5]naphthyridine-3,4-diamine of Formula XV is cyclized to provide a 1,3-dihydro-1H-imidazo[4,5-c][1,5]naphthyridine-2-thione of Formula XVI. The cyclization can be conveniently carried out by combining a [1,5]naphthyridine-3,4-diamine of Formula XV with 1,1'-thiocarbonyldiimidazole in a suitable solvent such as tetrahydrofuran (THF), tert-butyl methyl ether, dichloromethane, or N,N-dimethylformamide (DMF). Optionally, the reaction can be carried out in the presence of excess base such as pyridine. The reaction may be carried out at room temperature or, preferably, at an elevated temperature such as 90° C. to 120° C. or the reflux temperature of the solvent.

Several [1,5]naphthyridine-3,4-diamines of Formula XV are known or can be prepared by known methods; see for example, U.S. Pat. No. 6,194,425 (Gerster et al), and. These methods include the reaction of a 4-chloro-3-nitro[1,5]naphthyridine with a primary amine of formula $R_1$—$NH_2$ in the presence of a tertiary amine and subsequent reduction of the nitro group. Numerous amines of Formula $R_1$—$NH_2$ are commercially available; others can be prepared by known methods. For example, a variety of substituted and unsubstituted arylalkylenyl amines and isomeric (aminomethyl)pyridines are commercially available. The synthesis of tetrahydro-2H-pyran-4-ylmethylamine hydrochloride, which can be used to prepare compounds of Formula XV wherein $R_1$ is a tetrahydro-2H-pyran-4-ylmethyl group, has been reported; see, U.S. Patent Application Publication No. 2004/0147543 (Hays et al), Examples 477-480.

In step (2) of Reaction Scheme I, a 1,3-dihydro-1H-imidazo[4,5-c][1,5]naphthyridine-2-thione of Formula XVI is methylated to provide a 2-(methylthio)-1H-imidazo[4,5-c][1,5]naphthyridine of Formula XVII. The reaction can be conveniently carried out by combining a compound of Formula XVI with iodomethane in a suitable solvent or solvent mixture, such as ethanol/water, in the presence of a base, such as ammonium hydroxide or sodium methoxide. The reaction can be carried out at room temperature.

In step (3) of Reaction Scheme I, a 2-(methylthio)-1H-imidazo[4,5-c][1,5]naphthyridine of Formula XVII is oxidized to a 2-(methylsulfonyl)-1H-imidazo[4,5-c][1,5]naphthyridine of Formula XVIII using a conventional oxidizing agent. The oxidation can be conveniently carried out, for example, by combining acetic acid and potassium permanganate with a compound of Formula XVII at room temperature. The reaction may be carried out in a suitable solvent such as water.

In step (4) of Reaction Scheme I, the methylsulfonyl group of a 2-(methylsulfonyl)-1H-imidazo[4,5-c][1,5]naphthyridine of Formula XVIII is displaced with an alkoxide of formula —O—$R_{2b}$ to provide a compound of Formula XIVa. Some alkoxides of these formulas are commercially available, for example, as alkali metal salts. Other alkoxides of these formulas can be readily prepared by known methods. The reaction can be carried out by combining an alkoxide with a 2-(methylsulfonyl)-1H-imidazo[4,5-c][1,5]naphthyridine of Formula XVIII at room temperature in a suitable solvent such as ethanol or methanol.

Alternatively, a compound of Formula XIVa can be prepared from a diamine of Formula XV by first cyclizing with 1,1'-carbonyldiimidazole under the conditions described in step (1) and then alkylating or benzylating the resulting 1H-imidazo[4,5-c][1,5]naphthyridin-2-ol by reaction with an alkyl or benzyl halide in the presence of a base such as potassium carbonate in a suitable solvent such as acetone, methanol, or ethanol. The alkylation reaction can be carried out at room temperature or at an elevated temperature such as the reflux temperature of the solvent.

In step (5) of Reaction Scheme I, an alkoxy-substituted 1H-imidazo[4,5-c][1,5]naphthyridine of Formula XIVa is oxidized to an alkoxy-substituted 1H-imidazo[4,5-c][1,5]naphthyridine-5N-oxide of Formula XIX using a conventional oxidizing agent capable of forming N-oxides. The reaction is conveniently carried out at room temperature by combining 3-chloroperoxybenzoic acid with a solution of a compound of Formula XIVa in a solvent such as chloroform or dichloromethane.

In step (6) of Reaction Scheme I, an alkoxy-substituted 1H-imidazo[4,5-c][1,5]naphthyridine-5N-oxide of Formula XIX is aminated to provide an alkoxy-substituted 1H-imidazo[4,5-c][1,5]naphthyridin-4-amine of Formula XX. Step (6) can be carried out by the activation of an N-oxide of Formula XIX by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide to a solution of the N-oxide of Formula XIX in a suitable solvent such as dichloromethane or chloroform and then adding p-toluenesulfonyl chloride. The reaction can be carried out at room temperature.

Steps (5) and (6) of Reaction Scheme I may be carried out as a one-pot procedure by adding 3-chloroperoxybenzoic acid to a solution of a compound of Formula XIVa in a solvent such as dichloromethane or chloroform and then adding ammonium hydroxide and p-toluenesulfonyl chloride without isolating the N-oxide compound of Formula XIX.

Reaction Scheme I

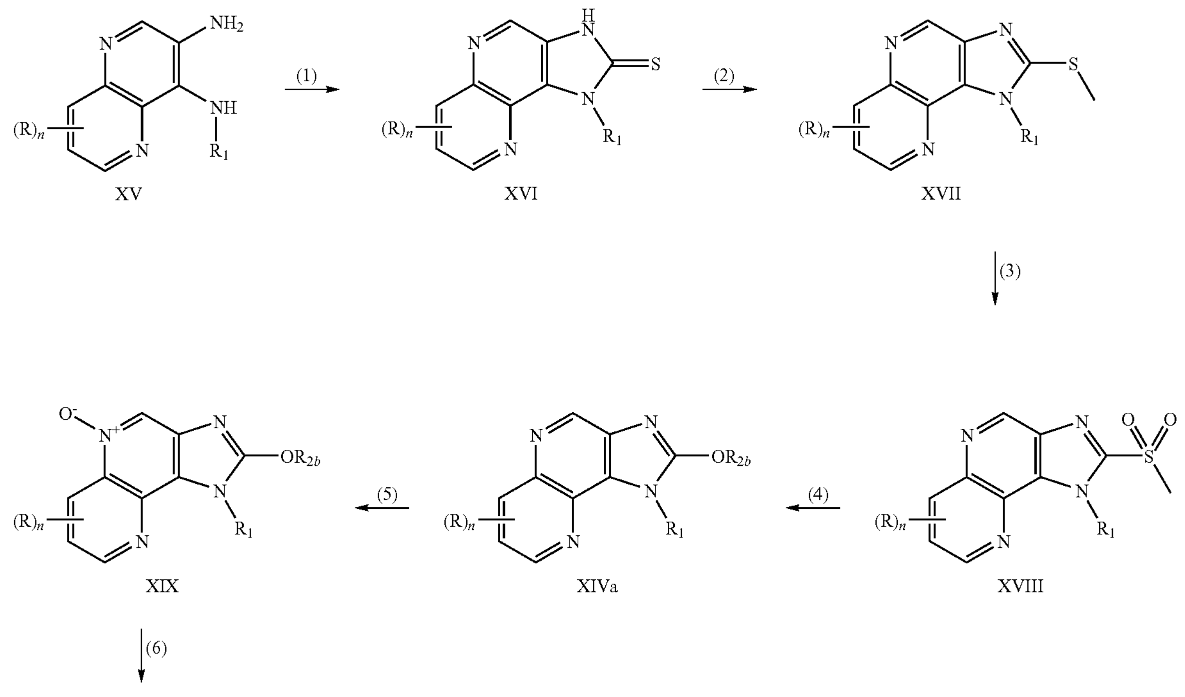

-continued

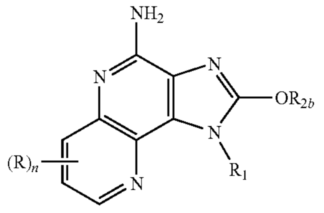

XX

For some embodiments, compounds of the invention can be prepared according to Reaction Scheme II, wherein R, $R_1$, $R_{2b}$, and n are as defined above. In step (1) of Reaction Scheme II, a 2-(methylthio)-1H-imidazo[4,5-c][1,5]naphthyridine of Formula XVII is oxidized to a 2-(methylsulfonyl)-1H-imidazo[4,5-c][1,5]naphthyridine-5N-oxide of Formula XXI using a conventional oxidizing agent capable of forming N-oxides and sulfones. The reaction is conveniently carried out at room temperature by combining at least three equivalents of 3-chloroperoxybenzoic acid with a solution of a compound of Formula XVII in a solvent such as chloroform or dichloromethane. The 5N-oxide of Formula XXI is then aminated according to the method of step (6) of Reaction Scheme I to provide a 2-(methylsulfonyl)-1H-imidazo[4,5-c][1,5]naphthyridin-4-amine of Formula XXII. Steps (1) and (2) of Reaction Scheme II may be carried out as a one-pot procedure as described for steps (5) and (6) of Reaction Scheme I.

In step (3) of Reaction Scheme II, the methylsulfonyl group of a 2-(methylsulfonyl)-1H-imidazo[4,5-c][1,5]naphthyridin-4-amine of Formula XXII is displaced with an alkoxide of Formula —O—$C_{1-4}$ alkyl, —O—$C_{2-4}$ alkylene-O—$C_{1-4}$ alkyl, or optionally substituted —O-benzyl to provide a compound of Formula XX. The reaction can be carried out according to the method described in step (4) of Reaction Scheme I.

Diamine XV or imidazonaphthyridine XX, prepared by the methods of either Reaction Scheme I or Reaction Scheme II, can undergo a number of transformations at the $R_1$ position to provide a variety of compounds of the invention. For example, tert-butyl amine can be used in the preparation of a compound or salt of Formula XV to provide a tert-butyl group at the $R_1$ position, which can be converted to a compound of Formula XV wherein $R_1$ is hydrogen by heating the tert-butyl-substituted compound with hydrochloric acid in a suitable solvent such as methanol at an elevated temperature such as 75° C. In another example, an amino alcohol can be used to provide a compound of Formula XV with a hydroxyalkyl group at the $R_1$ position. The hydroxy group can optionally be protected for subsequent steps in Reaction Scheme I or Reaction Scheme II and then deprotected and converted to a chloro group using conventional chlorination methods, such as treatment with thionyl chloride at room temperature or at an elevated temperature in a suitable solvent such as dichloromethane or 1,2-dichloroethane. A compound of Formula XV or XX with a chloroalkyl group at the $R_1$ position can be treated with a cyclic secondary amine to provide a compound in which $R_1$ is —$X_1$-Het. Many cyclic secondary amines are commercially available, such as unsubstituted or substituted pyrrolidines, piperidines, morpholines, and piperazines; others can be prepared using conventional methods. The reaction can be conveniently carried out by adding a cyclic secondary amine to a chloroalkyl substituted compound in a suitable solvent such as DMF. The reaction can be conveniently carried out in the presence of a base such as potassium carbonate at an elevated temperature such as 65° C. In another example, an amine of formula $NH_2$—$X_1$—NH-Boc or $NH_2$—CH($R_{11}$)—Ar'-CH($R_{11}$)—NH-Boc can be used in the preparation of a compound of Formula XV wherein $R_1$ is —$X_1$—NH-Boc or —CH($R_{11}$)—Ar'-CH($R_{11}$)—NH-Boc, in which Boc is tert-butoxycarbonyl and XI, $R_{11}$, and Ar' are as defined above. The Boc group can be removed by conventional methods after the steps of Reaction Scheme I or II are used to prepare a compound of Formula XX. The resulting amino group can be treated by conventional methods to provide a compound of Formula XX in which $R_1$ is —$X_1$—N($R_8$)-Q-$R_4$, —CH($R_{11}$)—Ar'-CH($R_{11}$)—N($R_8$)-Q-$R_4$, or —CH($R_{11}$)—Ar'-CH($R_{11}$)—$R_5$, wherein $R_5$ is

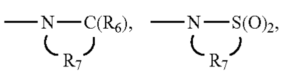

or

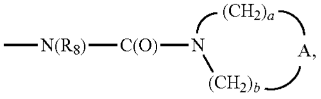

and $R_4$, $R_6$, $R_7$, $R_8$, Q, A, a, and b are as defined above. For example, the amino group can be treated with an acid chloride of Formula $R_4C(O)Cl$ or $C_1$—$R_7C(O)Cl$, a sulfonyl chloride of Formula $R_4S(O)_2Cl$ or $C_1$—$R_7S(O)_2Cl$, a sulfonic anhydride of Formula $(R_4S(O)_2)_2O$, an isocyanate of Formula $R_4N{=}C{=}O$, $R_4(CO)N{=}C{=}O$, $R_4N{=}C{=}S$, or $R_4S(O)_2N{=}C{=}O$, a carbamoyl chloride of Formula $R_4N(R_8)C(O)Cl$ or

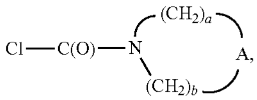

or a sulfamoyl chloride of Formula $R_4N(R_8)S(O)_2Cl$ to provide an amide, sulfonamide, urea, or sulfamide. The reaction can be conveniently carried out by combining the acid chloride, sulfonyl chloride, sulfonic anhydride, or isocyanate and a solution of an amino-substituted compound, and a base such as triethylamine or N,N-diisopropylethylamine in a suitable solvent such as dichloromethane or N,N-dimethylacetamide (DMA). The reaction can be carried out at room temperature. When a chloroalkanesulfonyl chloride of Formula $C_1$—$R_7S(O)_2Cl$ or a chloroalkanoyl chloride of Formula $C_1$—$R_7C(O)Cl$ is used in this reaction, the isolable intermediate chloroalkanesulfonamide or chloroalkanamide can then be treated with a base such as 1,8-diazabicyclo[5.4.0]undec-7-ene (DBU) or sodium hydride at room temperature in a suitable solvent such as DMF to effect a cyclization and provide a compound of Formula XX in which $R_1$ is —CH($R_{11}$)—Ar'-CH($R_{11}$)—$R_5$, wherein $R_5$ is

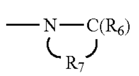
or
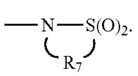

A compound of Formula XX wherein $R_{2b}$ is $C_{1-4}$ alkyl, prepared by the methods described in Reaction Scheme I or II, can be converted to a 2-hydroxy compound of Formula XXIII, a subgenus of Formulas I and II, in step (4) of Reaction Scheme II using conventional dealkylation methods. For example, demethylation can be carried out by treating a compound of Formula XX wherein $R_{2b}$ is $C_{1-4}$ alkyl with boron tribromide in a suitable solvent such as dichloromethane at room temperature or a sub-ambient temperature such as −78° C. In addition, a compound of Formula XX wherein $R_{2b}$ is $C_{1-4}$ alkoxy$C_{2-4}$ alkylenyl, prepared by the methods described in Reaction Scheme I or II, can be converted to a compound having a hydroxy$C_{2-4}$ alkylenyl group at the $R_2$ position using this dealkylation method. A compound of Formula XXIII can also be prepared from a compound of Formula XX wherein $R_{2b}$ is benzyl that is optionally substituted as defined above. The benzyl group or substituted benzyl group can be removed by heterogeneous hydrogenation or by treatment with trifluoroacetic acid using conditions known to one of skill in the art.

Alternatively, a sulfone of Formula XXII can be converted directly to a 4-amino-1H-imidazo[4,5-c][1,5]naphthyridin-2-ol of Formula XXIII by treating a solution of Formula XXII with an acid such as hydrochloric acid or trifluoroacetic acid and heating.

Reaction Scheme II

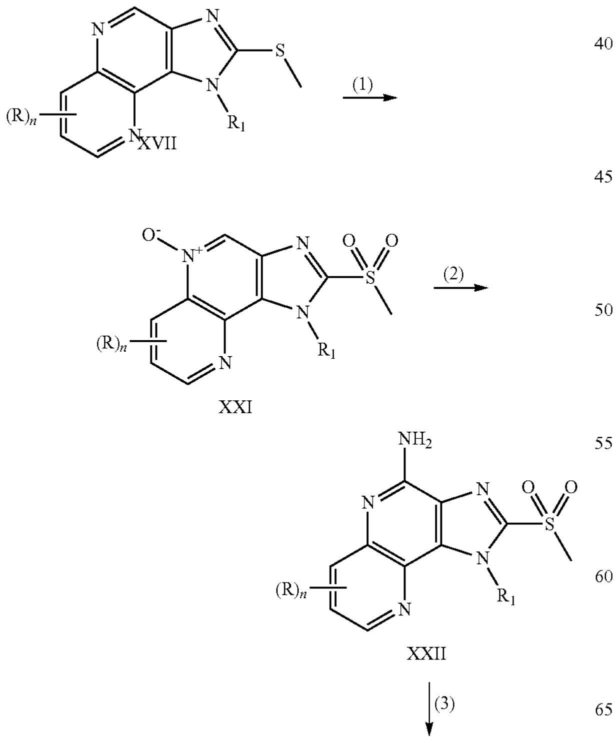

XVII

XXI

XXII

-continued

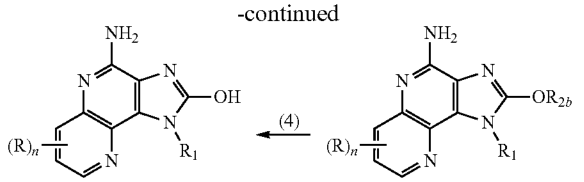

XXIII XX

Compounds of the invention can also be prepared according to Reaction Scheme III, wherein R, $R_1$, and $R_{2b}$ are as defined above; n is an integer from 0 to 3; m is 0 or 1 with the proviso that when m is 1, n is 0 or 1; D is —Br, —I, or —$OCH_3$; and Ph is phenyl. 2-Aminonicotinic acids of Formula XXIV are known and can be prepared by known methods. The compound where n and m are both 0 is commercially available. In step (1) of Reaction Scheme III, a 2-aminonicotinic acid of Formula XXIV is heated with acetic anhydride to provide a 2-methyl-4H-pyrido[2,3-d][1,3]oxazin-4-one of Formula XXV.

In step (2) of Reaction Scheme III a compound of Formula XXV is combined with sodium azide in a suitable solvent such as acetic acid to provide a tetrazolyl pyridine-2-carboxylic acid of Formula XXVI. The reaction conveniently may be run at ambient temperature.

In step (3) of Reaction Scheme III an acid of Formula XXVI is esterified by conventional methods to provide a compound of Formula XXVII. The reaction is conveniently carried out by combining the acid of Formula XXVI with ethyl iodide in the presence of a base such as potassium carbonate in a suitable solvent such as acetone.

In step (4) of Reaction Scheme III a compound of Formula XXVII is cyclized to provide a tetraazolo[1,5-a][1,8]naphthyridin-5-ol of Formula XXVIII. The reaction may be carried out by treating the compound of Formula XXVII with an alkoxide base such as potassium ethoxide in a suitable solvent such as DMF. The reaction can be run at ambient temperature.

In step (5) of Reaction Scheme III a compound of Formula XXVIII is nitrated using a suitable nitrating agent such as nitric acid to provide a 4-nitrotetraazolo[1,5-a][1,8]naphthyridin-5-ol of Formula XXIX. The reaction is conveniently carried out by adding nitric acid to the compound of Formula XXVIII in a suitable solvent such as propionic acid and heating the mixture at an elevated temperature.

In step (6) of Reaction Scheme III the hydroxy group of a compound of Formula XXIX is converted to a trifluoromethanesulfonate to provide a compound of Formula XXX. The reaction is preferably carried out by combining a compound of Formula XXIX with a base, preferably a tertiary amine such as triethylamine, in a suitable solvent such as dichloromethane and then slowly adding trifluoromethanesulfonic anhydride. The addition is preferably carried out at a reduced temperature such as, for example, at about 0° C. The product can be isolated by conventional methods or it can be carried on without isolation as described below in connection with step (7).

In step (7) of Reaction Scheme III a compound of Formula XXX is reacted with an amine of formula $R_1$—$NH_2$ to provide a 4-nitrotetraazolo[1,5-a][1,8]naphthyridin-5-amine of Formula XXXI. The reaction can be carried out by adding the amine to the reaction mixture resulting from step (6). The reaction can also be carried out by adding the amine to a solution of the compound of Formula XXX and a tertiary amine such as triethylamine in a suitable solvent such as dichloromethane. The reaction may be run at ambient temperature.

In step (8) of Reaction Scheme III a compound of Formula XXXI is reduced to provide a tetraazolo[1,5-a][1,8]naphthyridin-4,5-diamine of Formula XXXII. Preferably, the reduction is carried out using platinum on carbon as the heterogeneous hydrogenation catalyst. The reaction can conveniently be carried out on a Parr apparatus in a suitable solvent such as ethanol.

In step (9) of Reaction Scheme III a compound of Formula XXXII is cyclized to provide an alkoxy-substituted 1H-tetraazolo[1,5-a]imidazo[4,5-c][1,8]naphthyridine of Formula XXXIII. The cyclization can be conveniently carried out by combining a compound of Formula XXXII with an orthocarbonate, for example tetraethyl orthocarbonate, in a suitable solvent such as acetic acid. The reaction may be carried out at room temperature or at an elevated temperature such as 30° C. to 50° C. Alternatively, the transformation can be carried out according to steps (1) through (4) of Reaction Scheme I.

In step (10) of Reaction Scheme III a compound of Formula XXXIII is reacted with triphenylphosphine to provide an alkoxy-substituted $N^4$-triphenylphosphinyl-1H-imidazo[4,5-c][1,8]naphthyridin-4-amine of Formula XXXIV. The reaction can be carried out by heating a compound of Formula XXXIII with triphenylphosphine in a suitable solvent such as 1,2-dichlorobenzene.

In step (11) of Reaction Scheme III a compound of Formula XXXIV is hydrolyzed to provide an alkoxy-substituted 1H-imidazo[4,5-c][1,8]naphthyridin-4-amine of Formula XXXV. The hydrolysis can be carried out by conventional methods such as by heating in a lower alkanol in the presence of an acid.

In Reaction Scheme III, when m is 1, step (12) is used to convert a compound of Formula XXXV to an alkoxy-substituted 1H-imidazo[4,5-c][1,8]naphthyridin-4-amine of Formula XXXVI. When D is —Br or —I, a 2-alkoxy-1H-imidazo[4,5-c][1,8]naphthyridin-4-amine of Formula XXXV can undergo known palladium-catalyzed coupling reactions such as the Suzuki coupling and the Heck reaction. For example, a compound of Formula XXXV undergoes Suzuki coupling with a boronic acid of Formula $R_3$—$B(OH)_2$, an anhydride thereof, or a boronic acid ester of Formula $R_3$—B(O-alkyl)$_2$; wherein $R_3$ is —$R_{4b}$, —$X_a$—$R_4$, —$X_b$—Y—$R_4$, or —$X_b$—$R_5$; where $X_a$ is alkenylene; $X_b$ is arylene, heteroarylene, and alkenylene interrupted or terminated by arylene or heteroarylene; $R_{4b}$ is aryl or heteroaryl where the aryl or heteroaryl groups can be unsubstituted or substituted as defined in $R_4$ above; and $R_4$, $R_5$, and Y are as defined above; to provide a compound of Formula XXXVI. Numerous boronic acids of Formula $R_3$—$B(OH)_2$, anhydrides thereof, and boronic acid esters of Formula $R_3$—B(O-alkyl)$_2$ are commercially available; others can be readily prepared using known synthetic methods.

The Heck reaction can also be used in step (12) of Reaction Scheme III to provide compounds of Formula XXXVI, wherein $R_3$ is —$X_3$—$R_{4b}$ and —$X_3$—Y—$R_4$. The Heck reaction is carried out by coupling a compound of Formula XXXV with a compound of the Formula $H_2C$═C(H)—$R_{4b}$ or $H_2C$═C(H)—Y—$R_4$. Several of these vinyl-substituted compounds are commercially available; others can be prepared by known methods. The Suzuki coupling and Heck reaction can be carried out according to any of the methods described in U.S. Patent Application Publication No. 2004/0147543 (Hays et al.) and copending PCT Patent Application US2005/021436 (Niwas et al.).

Compounds of Formula XXXVI, wherein $R_3$ is —$X_c$—$R_4$, $X_c$ is alkynylene, and $R_4$ is as defined above, can also be prepared by palladium catalyzed coupling reactions such as the Stille coupling or Sonogashira coupling. These reactions are carried out by coupling a compound of Formula XXXV with a compound of the Formula (alkyl)$_3$Sn—C≡C—$R_4$, (alkyl)$_3$Si—C≡C—$R_4$, or H—C≡C—$R_4$.

Compounds of Formula XXXVI prepared as described above by palladium-mediated coupling reactions, wherein $R_3$ is —$X_3$—$R_4$, —$X_3$—Y—$R_4$, —$X_{b2}$—Y—$R_4$, —$X_{b2}$—$R_5$, or —$X_c$—$R_4$, where $X_{b2}$ is alkenylene interrupted or terminated by arylene or heteroarylene, and $X_a$, $X_c$, Y, $R_4$, and $R_5$ are as defined above, can undergo reduction of the alkenylene or alkynylene group present to provide compounds of Formula XXXVI wherein $R_3$ is —$X_d$—$R_4$, —$X_d$—Y—$R_4$, —$X_e$—Y—$R_4$, or —$X_e$—$R_5$, where $X_d$ is alkylene; $X_e$ is alkylene interrupted or terminated by arylene or heteroarylene; and $R_4$, $R_5$, and Y are as defined above. The reduction can be carried out by hydrogenation according to the methods described in U.S. Patent Application Publication No. 2004/0147543 (Hays et al.) and copending PCT Patent Application US2005/021436 (Niwas et al.).

Compounds of Formula XXXV wherein D is —$OCH_3$ can be converted in step (12) of Reaction Scheme III to compounds of Formula XXXVI wherein $R_3$ is —O—$R_{4b}$, —O—X—$R_4$, —O—X—Y—$R_4$, or —O—X—$R_5$; wherein $R_4$, $R_{4b}$, $R_5$, X, and Y are as defined above. When D is —$OCH_3$, the reaction shown in step (12) of Reaction Scheme III is carried out in two parts. In part (i), the methoxy group is demethylated to provide a hydroxy-substituted compound. The demethylation can be carried out as described above. For this reaction, it is preferred that $R_{2b}$ is a benzyl group or substituted benzyl group. In part (ii), a the hydroxy-substituted compound prepared in part (i) is converted to a compound of Formula XXXVI, wherein $R_3$ is —O—$R_{4b}$, —O—X—$R_4$, —O—X—Y—$R_4$, or —O—X—$R_5$, using a Williamson-type ether synthesis. The reaction is effected by treating a hydroxy-substituted 1H-imidazo[4,5-c][1,8]naphthyridin-4-amine with an aryl, alkyl, or arylalkylenyl halide of Formula Halide-$R_{4b}$, Halide-alkylene-$R_4$, Halide-alkylene-Y—$R_4$, or Halide-alkylene-$R_5$ in the presence of a base. Numerous alkyl, arylalkylenyl, and aryl halides of these formulas are commercially available, including substituted benzyl bromides and chlorides, substituted or unsubstituted alkyl or arylalkylenyl bromides and chlorides, and substituted fluorobenzenes. Other halides of these formulas can be prepared using conventional synthetic methods. The methods described in International Patent Application Publication Nos. WO2005/020999 (Lindstrom et al.) and WO2005/032484 (Lindstrom et al.) can be used.

In step (13) of Reaction Scheme III, an alkoxy-substituted 1H-imidazo[4,5-c][1,8]naphthyridin-4-amine of Formula XXXVI is converted to a 4-amino-1H-imidazo[4,5-c][1,8]naphthyridin-2-ol of Formula XXXVII, a subgenus of Formulas I and V, using one of the methods described in step (4) of Reaction Scheme II.

The methods of Reaction Scheme III can also be carried out using a substituted 3-aminoisonicotinic acid as a starting material instead of a 2-aminonicotinic acid of Formula XXIV to provide hydroxy- or alkoxy-substituted 1H-imidazo[4,5-c][1,7]naphthyridin-4-amines of the invention.

Reaction Scheme III
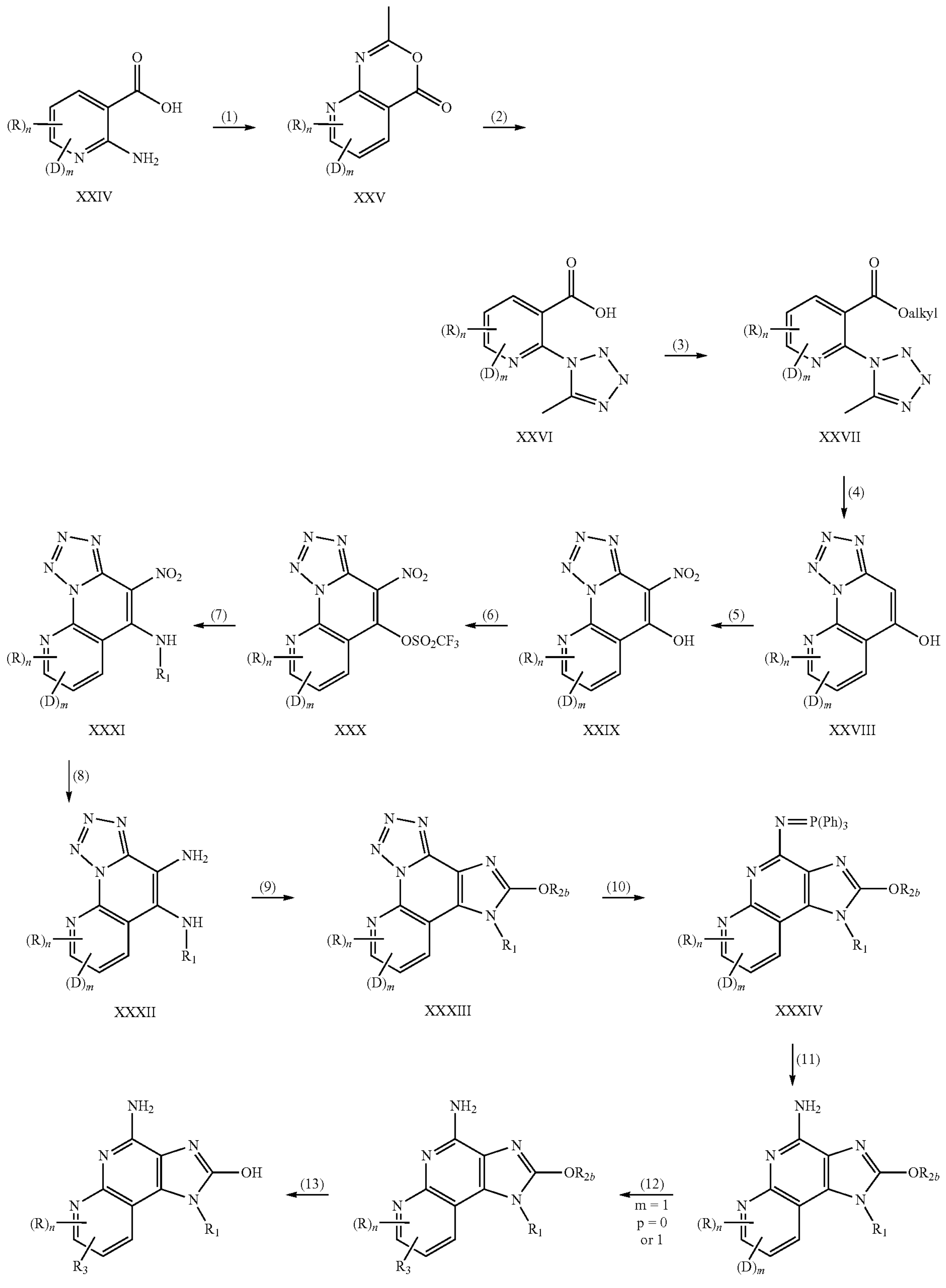
XXIV XXV XXVI XXVII XXVIII XXIX XXX XXXI XXXII XXXIII XXXIV XXXV XXXVI XXXVII The methods described in step (12) and (13) of Reaction Scheme III can also be used to prepare compounds of Formula XXXVIII and XXXIX from 2-alkoxy-1H-imidazo[4,5-c][1,5]naphthyridin-4-amines of Formula XXa as shown in Reaction Scheme IV, wherein D, R, $R_1$, and $R_{2b}$ are as defined above, and n is 0 or 1. Compounds of Formula XXa are available from the methods described in Reaction Scheme I or II starting with compounds of Formula XV in which one of the R groups is —Br, —I, or —$OCH_3$. These compounds are known or can be made from known methods; see, for example, copending PCT Patent Application US2005/021436 (Niwas et al.).

Reaction Scheme IV

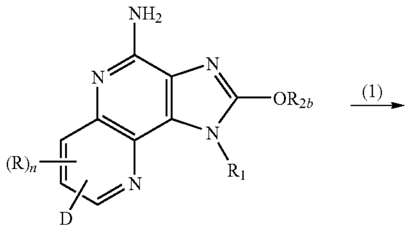

XXa

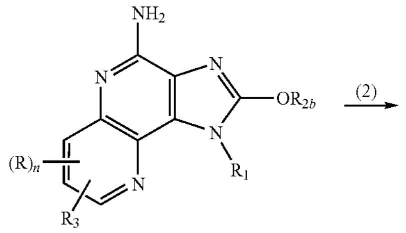

XXXVIII

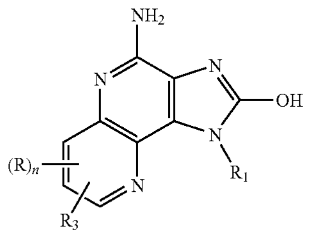

XXXIX

For some embodiments, compounds of the invention can be prepared according to Reaction Scheme V wherein R, $R_1$, $R_{2b}$, and D are as defined above; m and n are as defined in Reaction Scheme III; Hal is —Br or —I; and M is a group such as —$B(OH)_2$, —B(O-alkyl$)_2$, —Sn(alkyl$)_3$, and —Zn-Halide, which can undergo palladium-mediated cross coupling reactions. Compounds of Formula XL can be prepared by reacting aminomalonitrile, which is available commercially as the p-toluenesulfonic acid salt, with triphosgene and a primary amine of formula $R_1$—$NH_2$. The reaction can be conveniently carried out in a suitable solvent such as THF in the presence of triethylamine or N,N-diisopropylethylamine. See, for example, the method described by Hirota, K. et al., *Heterocycles,* 55, pp. 2279-2282 (2001).

In step (1) of Reaction Scheme V, a 2-hydroxy imidazole of Formula XL is alkylated or protected as a benzyl ether to provide an imidazole of Formula $XL_a$. The reaction can be carried out by treating a compound of Formula XL with an alkyl or benzyl halide in the presence of a base such as potassium carbonate in a suitable solvent such as acetone, methanol, or ethanol. The reaction can be carried out at room temperature or at an elevated temperature such as the reflux temperature of the solvent.

In step (2) of Reaction Scheme V, a solution of a compound of Formula $XL_a$ in diiodomethane or bromoform is treated with isoamyl nitrite or tert-butyl nitrite at an elevated temperature to yield a compound of Formula XLI.

In step (3) of Reaction Scheme V, an iodo or bromo-substituted compound of Formula XLI undergoes a transition-metal catalyzed cross coupling reaction with a reagent of Formula XLII to form a compound of Formula XLIII. Reagents of Formula XLII are known to undergo coupling reactions. One reagent of Formula XLII is commercially available (2,2-dimethyl-N-[3-(4,4,5,5-tetramethyl-1,3,2-dioxaborolan-2-yl)pyridin-4-yl]propanamide, CB Research and Development, Inc. in New Castle, Del.); others can be prepared using known synthetic methods. For example, tert-butylcarbonyl protected aminopyridines undergo directed ortho metalation in the presence of butyllithium reagents. The resulting organolithium intermediate reacts with electrophiles such as B(O-alkyl$)_3$ and ClSn(alkyl$)_3$ to provide compounds of Formula XLII, where M is —B(O-alkyl$)_2$ or —$B(OH)_2$ and —Sn(alkyl$)_3$, respectively.

In step (3), a Suzuki coupling reaction is conveniently carried out by heating a mixture of the compound of Formula XLI, palladium (II) acetate, triphenylphosphine, and a boron reagent of Formula XLII, where M is —$B(OH)_2$ or —B(O-alkyl$)_2$, in the presence of a base such as sodium carbonate. The reaction is carried out in a suitable solvent or solvent mixture such as n-propanol:water and can be heated at an elevated temperature such as 100° C.

In step (4) of Reaction Scheme V, a compound of Formula XLIII undergoes a base-promoted intramolecular cyclization followed by hydrolysis of the tert-butylcarbonyl group to provide a compound of Formula XLIV. The reaction is conveniently carried out by heating a compound of Formula XLIII with potassium tert-butoxide in a suitable solvent such as ethanol at an elevated temperature such as the reflux temperature of the solvent.

In step (5) of Reaction Scheme V, a 1H-imidazo[4,5-c][1,6]naphthyridin-4-amine of Formula XLIV is converted to a 4-amino-1H-imidazo[4,5-c][1,6]naphthyridin-2-ol of Formula XLV, a subgenus of Formula I and III, according to one of the methods of step (4) of Reaction Scheme II. Compounds of Formula XLIV wherein m is 1 may also be treated according to one of the methods of step (12) of Reaction Scheme III to provide 1H-imidazo[4,5-c][1,6]naphthyridin-4-amine compounds of the invention containing an $R_3$ group.

Reaction Scheme V

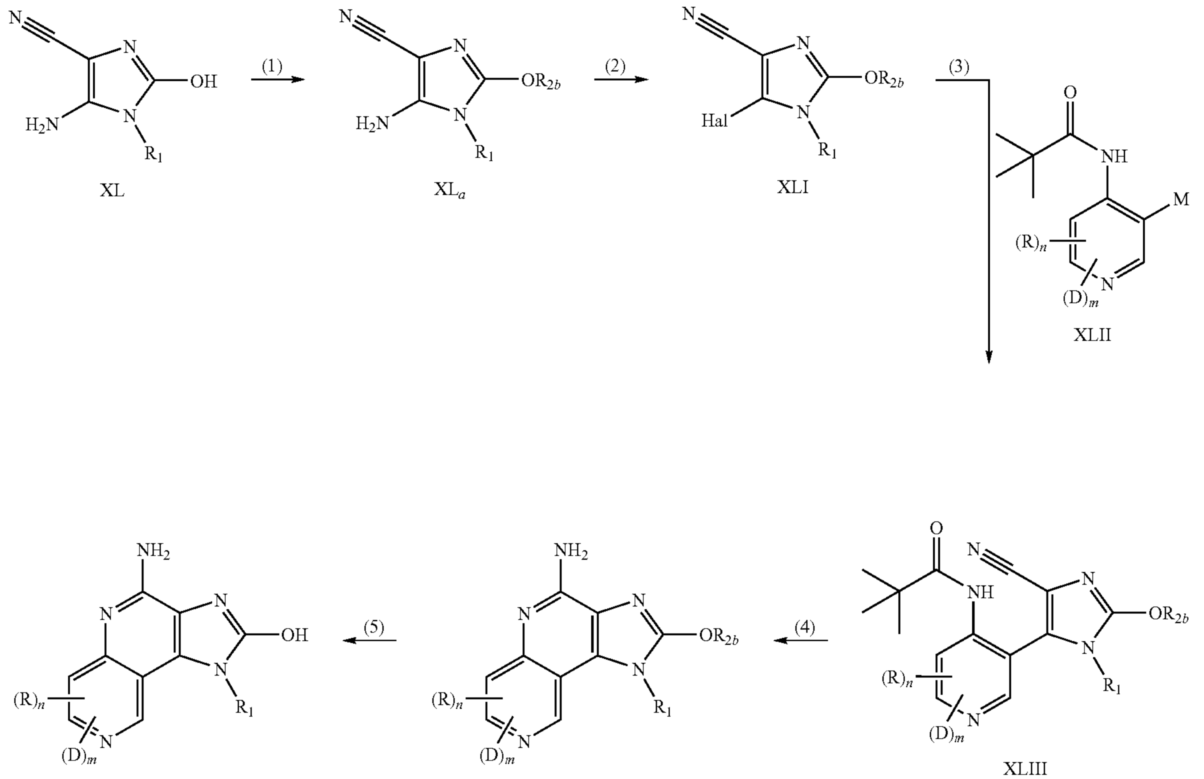

XL, XL$_a$, XLI, XLII, XLIII, XLIV, XLV

For some embodiments, compounds of the invention can be prepared according to Reaction Scheme VI, wherein $R_{A1}$ and $R_{B1}$ taken together form a fused pyridine ring that is unsubstituted or substituted by one or more $R_a$ groups; $R_{A2}$ and $R_{B2}$ taken together form a fused tetrahydropyridine ring that is unsubstituted or substituted by one or more $R_a$ groups; $R_a$ is alkyl, alkoxy, or —$N(R_9)_2$; $R_{2c}$ is $C_{1-4}$ alkyl, hydroxy$C_{2-4}$ alkylenyl, or $C_{1-4}$ alkoxy$C_{2-4}$ alkylenyl; and $R_{1a}$ is a subset of $R_1$ as defined above that does not include those substituents that one skilled in the art would recognize as being susceptible to reduction under the acidic hydrogenation conditions of the reaction. These susceptible groups include, for example, alkenyl, alkynyl, and aryl groups and groups bearing nitro substituents.

As shown in step (1) of Reaction Scheme VI, a 2-substituted-1H-imidazo[4,5-c]naphthyridin-4-amine of Formula XLVI can be reduced to a 6,7,8,9-tetrahydronaphthyridine of Formula XLVII, a subgenus of Formula I. Compounds of Formula XLVI can be prepared according to the methods described in Reaction Schemes I, II, III, or V. The reaction is conveniently carried out under heterogeneous hydrogenation conditions by adding platinum (IV) oxide to a solution of the compound of Formula XLVI in trifluoroacetic acid and placing the reaction under hydrogen pressure. The reaction can be carried out on a Parr apparatus at room temperature.

In step (2) of Reaction Scheme VI, a compound of Formula XLVII wherein $R_{2c}$ is $C_{1-4}$ alkyl can be dealkylated to provide a 4-amino-6,7,8,9-tetrahydro-1H-imidazo[4,5-c]naphthyridin-2-ol of Formula XLVIII using the dealkylation method described in step (4) of Reaction Scheme II.

Reaction Scheme VI

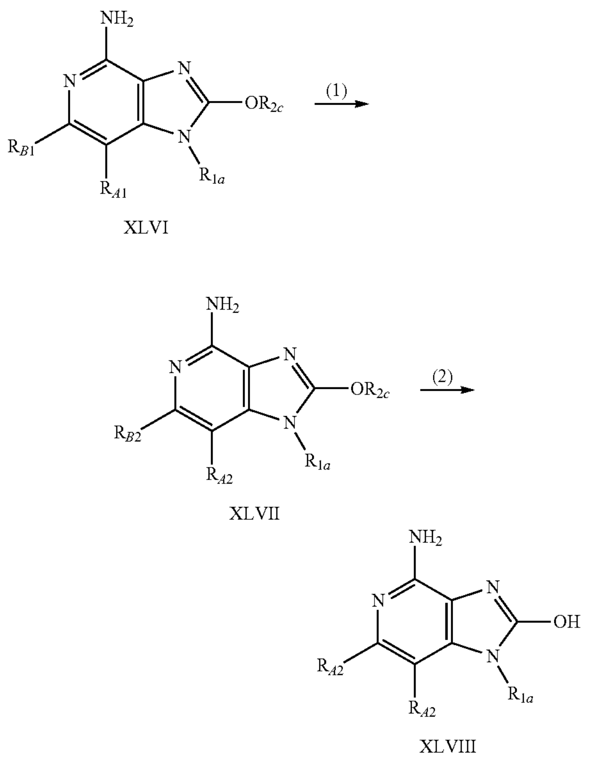

XLVI, XLVII, XLVIII

For certain embodiments, 6,7,8,9-tetrahydronaphthyridines of the invention can be prepared according to Reaction Scheme VII, wherein Boc, n, $R_a$, and $R_{2c}$ are as defined above; and $R_{1b}$ is selected from the group consisting of —CH($R_{11}$)—Ar, —CH($R_{11}$)—Ar'-$R_4$, —CH($R_{11}$)—Ar'-Y—$R_4$, —CH($R_{11}$)—Ar'-CH($R_{11}$)—Y—$R_4$, —CH($R_{11}$)—Ar'—$R_5$, and —CH($R_{11}$)—Ar'-CH($R_{11}$)—$R_5$. Compounds of Formula subgenus of Formula I and VI. In step (5), a compound of Formula LIII wherein $R_{2c}$ is $C_{1-4}$ alkyl can be dealkylated to provide a 4-amino-6,7,8,9-tetrahydro-1H-imidazo[4,5-c][1,5]naphthyridin-2-ol of Formula LIV, a subgenus of Formulas I and VI, using the dealkylation method described in step (4) of Reaction Scheme II.

Reaction Scheme VII

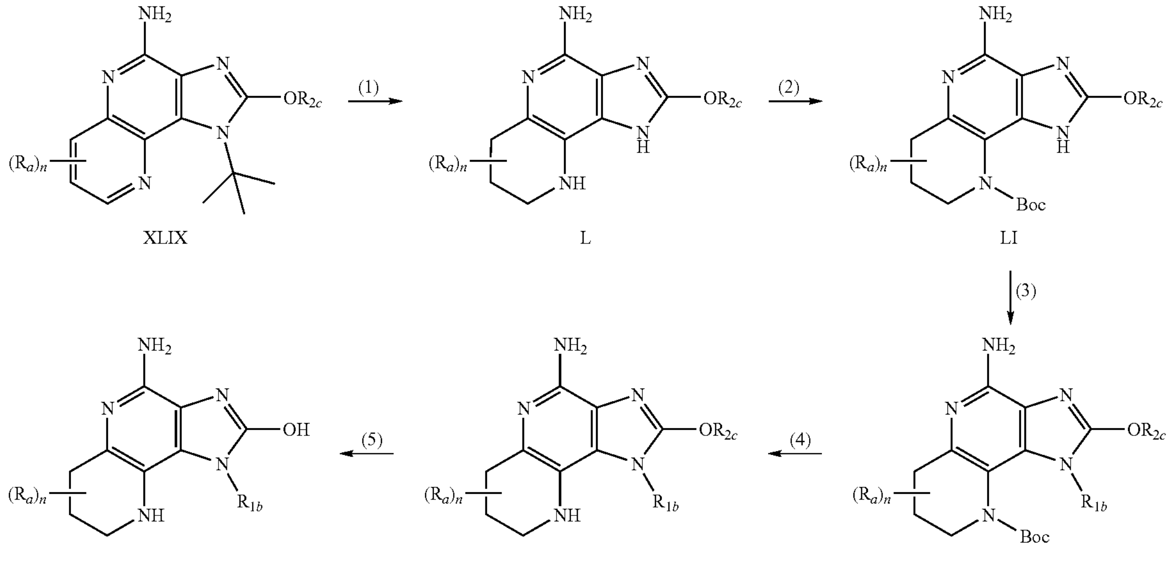

XLIX L LI LII LIII LIV

XLIX can be prepared according to the methods described in Reaction Scheme I or II beginning with a diamine of Formula XV wherein $R_1$ is a tert-butyl group. In step (1) of Reaction Scheme VII, a 2-substituted-1H-imidazo[4,5-c][1,5]naphthyridin-4-amine of Formula XLIX can be reduced according to the method shown in step (1) of Reaction Scheme VI to provide a tetrahydronaphthyridine of Formula L. The tert-butyl group may be cleaved under these conditions or may be removed in a subsequent step by heating the reduced product with hydrochloric acid in a suitable solvent such as methanol. The [1,8], [1,7,], and [1,6]2-substituted-1H-imidazo[4,5-c]naphthyridin-4-amine isomers of Formula XLIX, which can be prepared according to the methods of Reaction Scheme III or V, can also be used as starting materials in Reaction Scheme VII.

In step (2) of Reaction Scheme VII, the secondary aliphatic nitrogen in the compound of Formula L is protected with a Boc group using conventional protection methods. The resulting compound of Formula LI can then be alkylated in step (3) under basic conditions with benzyl bromide, a substituted benzyl bromide or chloride or a substituted or unsubstituted heteroarylalkylenyl bromide or chloride to provide a compound of Formula LII. The alkylation can be conveniently carried out by combining a compound of Formula LI with the alkylating agent in the presence of a base such as potassium carbonate in a suitable solvent such as DMF. The reaction can be carried out at room temperature. A mixture of alkylated isomers may result and may be separated using conventional methods to provide a compound of Formula LII.

In step (4) of Reaction Scheme VII, a protected tetrahydronaphthyridine of Formula LII is deprotected using conventional methods to provide a compound of Formula LIII, a For certain embodiments, compounds of the invention can be prepared according to Reaction Scheme VIII, wherein $R_1$, $R_{2a}$, $R_A$, $R_B$, and $G_1$ are as defined above. Compounds of Formula I can be prepared according to the methods of any of Reaction Schemes I through VII. Step (1) of Reaction Scheme VIII can be used to prepare a compound of Formula $X_c$. The amino group of a compound of Formula I can be converted by conventional methods to a functional group such as an amide, carbamate, urea, amidine, or another hydroylizable group. A compound of this type can be made by the replacement of a hydrogen atom in an amino group with a group such as —C(O)—R', α-aminoacyl, α-aminoacyl-α-aminoacyl, —C(O)—O—R', —C(O)—N(R")—R', —C(=NY')—R', CH(OH)—C(O)—OY', —CH(O$C_{1-4}$ alkyl)$Y_0$, —$CH_2Y_1$, or —CH($CH_3$)$Y_1$; wherein R' and R" are each independently $C_{1-10}$ alkyl, $C_{3-7}$ cycloalkyl, phenyl, benzyl, or 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl$C_{1-4}$ alkylenyl, heteroaryl$C_{1-4}$ alkylenyl, halo$C_{1-4}$ alkylenyl, halo$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —S$(O)_2$—$NH_2$; with the proviso that R" may also be hydrogen; each α-aminoacyl group is independently selected from racemic, D, or L-amino acids; Y' is hydrogen, $C_{1-6}$ alkyl, or benzyl; $Y_0$ is $C_{1-6}$ alkyl, carboxy$C_{1-6}$ alkylenyl, amino$C_{1-4}$ alkylenyl, mono-N—$C_{1-6}$ alkylamino$C_{1-4}$ alkylenyl, or di-N,N—$C_{1-6}$ alkylamino$C_{1-4}$ alkylenyl; and $Y_1$ is mono-N—$C_{1-6}$ alkylamino, di-N,N—$C_{1-6}$ alkylamino, morpholin-4-yl, piperidin-1-yl, pyrrolidin-1-yl, or 4-$C_{1-4}$ alkylpiperazin-1-yl. Particularly useful compounds of Formula $X_c$ are amides derived from carboxylic acids containing one to ten carbon atoms, amides derived from amino acids, and carbamates containing one to ten carbon atoms. The reaction can be carried out, for example, by combining a compound of Formula I with a chloroformate or acid chloride, such as ethyl chloroformate or acetyl chloride, in the presence of a base such as triethylamine in a suitable solvent such as dichloromethane at room temperature.

In step (2) of Reaction Scheme VIII, a compound of Formula $X_c$ can be converted to a 2-hydroxy naphthyridine compound of Formula $X_d$ using one of the methods described in step (4) of Reaction Scheme II.

Reaction Scheme VIII

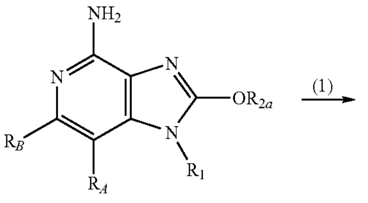

$I_c$

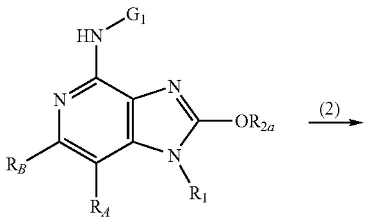

$X_c$

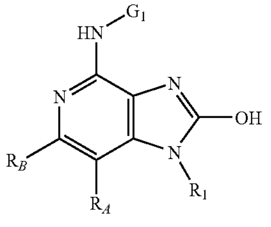

$X_d$

Reaction Scheme IX can be used to convert a compound of Formula $I_d$, which can be prepared using the methods of any of Reaction Schemes I through VII, to a compound of Formula XI. The hydrogen atom of the alcohol group of a compound of Formula $I_d$ can be replaced using conventional methods with a group such as $C_{1-6}$ alkanoyloxymethyl, 1-($C_{1-6}$ alkanoyloxy)ethyl, 1-methyl-1-($C_{1-6}$ alkanoyloxy) ethyl, $C_{1-6}$ alkoxycarbonyloxymethyl, N—($C_{1-6}$ alkoxycarbonyl)aminomethyl, succinoyl, $C_{1-6}$ alkanoyl, α-amino$C_{1-4}$ alkanoyl, arylacyl, —P(O)(OH)$_2$, —P(O)(O—$C_{1-6}$ alkyl)$_2$, $C_{1-6}$ alkoxycarbonyl, $C_{1-6}$ alkylcarbamoyl, and α-aminoacyl or α-aminoacyl-α-aminoacyl, where each α-aminoacyl group is independently selected from racemic, D, and L-amino acids. Particularly useful compounds of Formula XI are esters made from carboxylic acids containing one to six carbon atoms, unsubstituted or substituted benzoic acid esters, or esters made from naturally occurring amino acids. These esters can be prepared by heating a compound of Formula $I_d$ with a carboxylic acid optionally in the presence of a base. The esterification reaction can be carried out in a suitable solvent such as methanol or ethanol.

Reaction Scheme IX

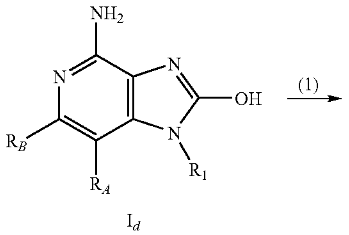

$I_d$

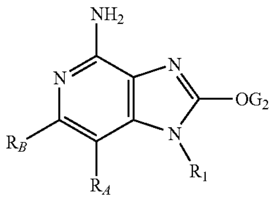

XI

Compounds of the invention can also be prepared using variations of the synthetic routes shown in Reaction Schemes I through IX that would be apparent to one of skill in the art. Compounds of the invention can also be prepared using the synthetic routes described in the EXAMPLES below.

Pharmaceutical Compositions and Biological Activity

Pharmaceutical compositions of the invention contain a therapeutically effective amount of a compound or salt described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. The exact amount of compound or salt used in a pharmaceutical composition of the invention will vary according to factors known to those of skill in the art, such as the physical and chemical nature of the compound or salt, the nature of the carrier, and the intended dosing regimen.

In some embodiments, the compositions of the invention will contain sufficient active ingredient or prodrug to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject.

In other embodiments, the compositions of the invention will contain sufficient active ingredient or prodrug to provide a dose of, for example, from about 0.01 mg/m$^2$ to about 5.0 mg/m$^2$, computed according to the Dubois method, in which the body surface area of a subject (m$^2$) is computed using the subject's body weight: m$^2$=(wt kg$^{0.425}$×height cm$^{0.725}$)×0.007184, although in some embodiments the methods may be performed by administering a compound or salt or composition in a dose outside this range. In some of these embodiments, the method includes administering sufficient compound to provide a dose of from about 0.1 mg/m$^2$ to about 2.0 mg/m$^2$ to the subject, for example, a dose of from about 0.4 mg/m$^2$ to about 1.2 mg/m$^2$.

A variety of dosage forms may be used, such as tablets, lozenges, capsules, parenteral formulations, syrups, creams, ointments, aerosol formulations, transdermal patches, transmucosal patches and the like. These dosage forms can be prepared with conventional pharmaceutically acceptable carriers and additives using conventional methods, which generally include the step of bringing the active ingredient into association with the carrier.

The compounds or salts of the invention can be administered as the single therapeutic agent in the treatment regimen, or the compounds or salts described herein may be administered in combination with one another or with other active agents, including additional immune response modifiers, antivirals, antibiotics, antibodies, proteins, peptides, oligonucleotides, etc.

Compounds or salts of the invention have been shown to induce the production of certain cytokines in experiments performed according to the tests set forth below. These results indicate that the compounds or salts are useful for modulating the immune response in a number of different ways, rendering them useful in the treatment of a variety of disorders.

Cytokines whose production may be induced by the administration of compounds or salts of the invention generally include interferon-α (IFN-α) and tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt of the invention to the animal. The animal to which the compound or salt is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts described herein can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts described herein can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt or composition and other component or components may be administered separately; together but independently such as in a solution; or together and associated with one another such as (a) covalently linked or (b) non-covalently associated, e.g., in a colloidal suspension.

Conditions for which compounds or salts or compositions identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella;*

(c) other infectious diseases, such as chlamydia, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to acute myeloid leukemia, acute lymphocytic leukemia, chronic myeloid leukemia, chronic lymphocytic leukemia, multiple myeloma, Hodgkin's lymphoma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia greata; and (g) diseases associated with wound repair such as, for example, inhibition of keloid formation and other types of scarring (e.g., enhancing wound healing, including chronic wounds).

Additionally, a compound or salt identified herein may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, *hemophilus influenza* b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts identified herein may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An animal may also be vaccinated by administering an effective amount of a compound or salt described herein, as a vaccine adjuvant. In one embodiment, there is provided a method of vaccinating an animal comprising administering an effective amount of a compound or salt described herein to the animal as a vaccine adjuvant.

An amount of a compound or salt effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) over a background level of such cytokines. The precise amount will vary according to factors known in the art but is expected to be a dose of about 100 ng/kg to about 50 mg/kg, preferably about 10 μg/kg to about 5 mg/kg. In other embodiments, the amount is expected to be a dose of, for example, from about 0.01 $mg/m^2$ to about 5.0 $mg/m^2$, (computed according to the Dubois method as described above) although in some embodiments the induction or inhibition of cytokine biosynthesis may be performed by administering a compound or salt in a dose outside this range. In some of these embodiments, the method includes administering sufficient compound or salt or composition to provide a dose of from about 0.1 $mg/m^2$ to about 2.0 $mg/m^2$ to the subject, for example, a dose of from about 0.4 $mg/m^2$ to about 1.2 $mg/m^2$.

The invention also provides a method of treating a viral infection in an animal and a method of treating a neoplastic disease in an animal comprising administering an effective amount of a compound or salt of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 μg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg. In other embodiments, the amount is expected to be a dose of, for example, from about 0.01 $mg/m^2$ to about 5.0 $mg/m^2$, (computed according to the Dubois method as described above) although in some embodiments either of these methods may be performed by administering a compound or salt in a dose outside this range. In some of these embodiments, the method includes administering sufficient compound or salt to provide a dose of from about 0.1 $mg/m^2$ to about 2.0 $mg/m^2$ to the subject, for example, a dose of from about 0.4 $mg/m^2$ to about 1.2 $mg/m^2$.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

Objects and advantages of this invention are further illustrated by the following examples, but the particular materials and amounts thereof recited in these examples, as well as other conditions and details, should not be construed to unduly limit this invention.

EXAMPLES

Example 1

1-Benzyl-2-ethoxy-1H-imidazo[4,5-c][1,5]naphthyridin-4-amine

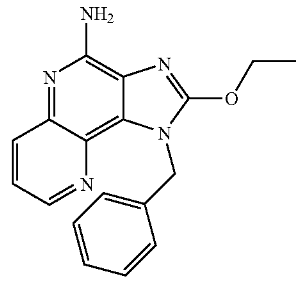

Part A

To a flask containing $N^4$-benzyl-[1,5]naphthyridine-3,4-diamine (24 g, 96 mmol, see U.S. Pat. No. 6,194,425 Example 67) was added pyridine (200 mL) followed by 1-1'-thiocarbonyldiimidazole (25.6 g, 144 mmol). The amber suspension was stirred, and to it was added THF (100 mL). A white solid precipitate was observed, and the reaction was heated to 115° C. After 10 minutes the reaction was cooled to room temperature, and most of the solvent was removed under reduced pressure. Water was added to the reaction mixture followed by dichloromethane and the suspension was transferred to a separatory funnel. The organic layer was separated and the aqueous was washed several times with dichloromethane. A white precipitate was present and was isolated by filtration (batch 1). The dichloromethane layers were combined, dried ($MgSO_4$), filtered, and the solvent evaporated to afford 1-benzyl-1,3-dihydro-1H-imidazo[4,5-c][1,5]naphthyridine-2-thione as a brown solid (batch 2). The combined weight of batch 1 and batch 2 was 24.55 g.

Part B

To 1-benzyl-1,3-dihydro-1H-imidazo[4,5-c][1,5]naphthyridine-2-thione (23 g, 78.7 mmol) was added a mixture of ethanol (150 mL) and water (150 mL) and the white suspension was stirred at room temperature. Ammonium hydroxide (30 mL) was added to the suspension followed by methyl iodide (22.3 g, 9.8 mmol). The suspension became thicker and a 1:1 mixture of ethanol and water was added to aid stirring. The suspension was stirred overnight after which water (300 mL) was added and stirring was continued for another 30 minutes. The white precipitate was filtered and washed with water and ether. The solid was dried in the vacuum oven over for 72 hours to afford crude 1-benzyl-2-methylsulfanyl-1H-imidazo[4,5-c][1,5]naphthyridine (about 25 g) as a white solid.

Part C

To 1-benzyl-2-methylsulfanyl-1H-imidazo[4,5-c][1,5]naphthyridine (1 g, 3.2 mmol) was added acetic acid (15 mL), and the white suspension was stirred for a few minutes. To this suspension was added potassium permanganate solution (0.87 g, 5.5 mmol, in water (15 mL)) in a dropwise manner, and the reaction was stirred at room temperature for 2 hours. To the reaction mixture was added sodium bisulfite (0.83 g) and the white suspension was stirred for several minutes. Water was added to this suspension and the reaction mixture was transferred to a separatory funnel. The product was extracted from the aqueous layer with several batches of dichloromethane. The dichloromethane layers were combined, dried ($MgSO_4$), filtered, and evaporated, and the resultant solid washed with ether to afford 1-benzyl-2-methanesulfonyl-1H-imidazo[4,5-c][1,5]naphthyridine as a white solid (0.9 g), mp 187-191° C.; MS (ESI) m/z 339 (M+H); Anal. Calcd for $C_{17}H_{14}N_4O_2S$: C, 60.34; H, 4.17; N, 16.56. Found C, 60.45; H, 3.97; N, 16.52.

Part D

To 1-benzyl-2-methanesulfonyl-1H-imidazo[4,5-c][1,5]naphthyridine (6.8 g, 20.1 mmol) was added ethanol (200 mL) and the suspension was stirred at room temperature. To this suspension was added sodium ethoxide (2.0 g) and the reaction was heated at reflux for 1 hour. After 1 hour additional sodium ethoxide was added, and the reaction was heated at reflux for 2 hours and then cooled to ambient. To this reaction was added water (500 mL), and the suspension was stirred for 30 minutes. The gray precipitate was isolated by filtration and washed with water and ether. The solid was dried under reduced pressure to afford 1-benzyl-2-ethoxy-1H-imidazo[4,5-c][1,5]naphthyridine (4.5 g) as a white solid.

Part E

To a stirred solution of 1H-imidazo[4,5-c][1,5]naphthyridine (4.5 g, 14.8 mmol) in dichloroethane (100 mL) was added 3-chloroperoxybenzoic acid (mCPBA) (77%, 4.9 g, 22.2 mmol), and the reaction was stirred at room temperature for 2 hours. To the reaction was then added ammonium hydroxide (100 mL) followed by p-toluenesulfonyl chloride (3.4 g, 17.7 mmol), and the reaction was stirred for 5 days at room temperature. To the reaction was added water and the reaction was transferred to a separatory funnel. The organic layer was separated and the aqueous layer was extracted with dichloromethane. The organic layers were combined, dried ($MgSO_4$), filtered, and evaporated to afford an orange solid. The product was purified by preparative HPLC (Analogix Separation System, and eluted with a gradient of 0-10% methanol in dichloromethane with 1% ammonium hydroxide) to provide a solid which was triturated with acetonitrile and filtered. The residue was washed with acetonitrile and then with ether and dried in a vacuum oven to afford 1-benzyl-2-ethoxy-1H-imidazo[4,5-c][1,5]naphthyridin-4-amine (2.0 g) as a white solid.

Example 2

4-Amino-1-benzyl-1H-imidazo[4,5-c][1,5]naphthyridin-2-ol

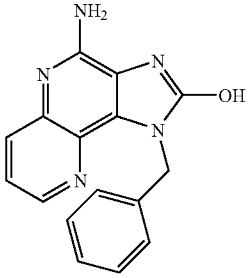

To a stirred suspension of 1-benzyl-2-ethoxy-1H-imidazo[4,5-c][1,5]naphthyridin-4-amine (1.3 g, 4 mmol) in dichloromethane (20 mL) was added boron tribromide (1M solution in dichloromethane, 10 mL, 10 mmol), and the reaction was stirred at room temperature. Additional aliquots of the boron tribromide solution (7.5 equivalents, 30 mmol total) were added to drive the reaction to completion. The reaction was concentrated under reduced pressure, and to it was added methanol (1 mL) followed by 6M HCl (100 mL). The reaction was heated at 50° C. for 2 hours, cooled in an ice bath, and adjusted to a basic pH by the addition of 6N NaOH. The product was extracted with dichloromethane and the organic layers were combined, dried ($MgSO_4$), filtered, and evaporated to afford crude product. The product was purified by preparative HPLC (Analogix Separation System, and eluted with a gradient of 0-10% methanol in dichloromethane with 1% ammonium hydroxide) to provide a solid which was triturated with hot acetonitrile, filtered, and washed with ether to afford 4-amino-1-benzyl-1H-imidazo[4,5-c][1,5]naphthyridin-2-ol (196 mg) as a yellow solid, mp>250° C.; HRMS (ESI) calcd for $C_{16}H_{13}N_5O[M+H]^+$: 292.1198. found 292.1198.

Example 3

2-Ethoxy-1-(tetrahydro-2H-pyran-4-ylmethyl)-1H-imidazo[4,5-c][1,5]naphthyridin-4-amine

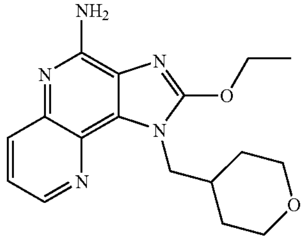

2-Ethoxy-1-(tetrahydro-2H-pyran-4-ylmethyl)-1H-imidazo[4,5-c][1,5]naphthyridin-4-amine was prepared according to the general methods described in Parts A through E of Example 1 using $N^4$-(tetrahydro-2H-pyran-4-ylmethyl)[1,5]naphthyridine-3,4-diamine in lieu of $N^4$-benzyl[1,5]naphthyridine-3,4-diamine in Part A. The product was provided as a very pale yellow solid, mp 197-200° C. Anal. Calcd for $C_{17}H_{21}N_5O_2$: C, 62.37; H, 6.47; N, 21.39. Found: C, 62.36; H, 6.31; N, 21.27.

Example 4

4-Amino-1-(tetrahydro-2H-pyran-4-ylmethyl)-1H-imidazo[4,5-c][1,5]naphthyridin-2-ol

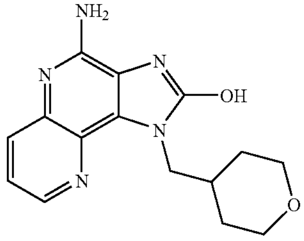

2-Ethoxy-1-(tetrahydro-2H-pyran-4-ylmethyl)-1H-imidazo[4,5-c][1,5]naphthyridin-4-amine was dealkylated using the method described in Example 2 to provide 4-amino-1-(tetrahydro-2H-pyran-4-ylmethyl)-1H-imidazo[4,5-c][1,5]naphthyridin-2-ol. The product was provided as a pale yellow solid, mp 250-260° C. Anal. Calcd for $C_{15}H_{17}N_5O_2$: C, 60.03; H, 5.71; N, 23.33. Found: C, 59.63; H, 5.60; N, 22.99.

Example 5

2-Ethoxy-1-[(1S)-1-phenylethyl]-1H-imidazo[4,5-c][1,5]naphthyridin-4-amine

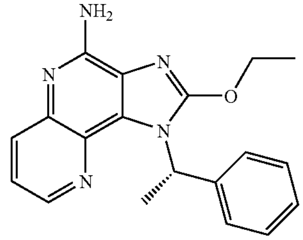

2-Ethoxy-1-[(1S)-1-phenylethyl]-1H-imidazo[4,5-c][1,5]naphthyridin-4-amine was prepared according to the general methods described in Parts A through E of Example 1 using $N^4$-[(1S)-1-phenylethyl][1,5]naphthyridine-3,4-diamine in lieu of $N^4$-benzyl[1,5]naphthyridine-3,4-diamine in Part A. The product was provided as white crystals, mp 187-190° C. Anal. Calcd for $C_{19}H_{19}N_5O$: C, 68.45; H, 5.74; N, 21.00. Found: C, 68.47; H, 5.69; N, 21.10.

Example 6

4-amino-1-[(1S)-1-phenylethyl]-1H-imidazo[4,5-c][1,5]naphthyridin-2-ol

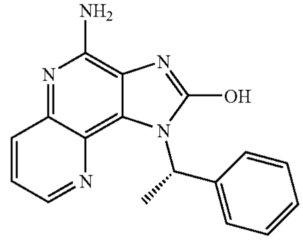

2-Ethoxy-1-[(1S)-1-phenylethyl]-1H-imidazo[4,5-c][1,5]naphthyridin-4-amine was dealkylated using the method described in Example 2 to provide 4-amino-1-[(1S)-1-phenylethyl]-1H-imidazo[4,5-c][1,5]naphthyridin-2-ol. The product was provided as pale yellow crystals, mp 241-243° C. Anal. Calcd for $C_{17}H_{15}N_5O$: C, 66.87; H, 4.95; N, 22.94. Found: C, 66.75; H, 4.76; N, 22.65.

Examples 7-49

Part A

Tert-butyl 2-(4-amino-2-ethoxy-1H-imidazo[4,5-c][1,5]naphthyridin-1-yl)ethylcarbamate was prepared according to the general methods described in Parts A through E of Example 1 using tert-butyl 2-[(3-amino[1,5]naphthyridin-4-yl)amino]ethylcarbamate in lieu of $N^4$-benzyl[1,5]naphthyridine-2,4-diamine in Part A.

Part B

A solution of tert-butyl 2-(4-amino-2-ethoxy-1H-imidazo[4,5-c][1,5]naphthyridin-1-yl)ethylcarbamate (6 g, 16 mmol) in methanol (25 mL) was combined with a solution of hydrogen chloride in dioxane (102 mL of 4N). The reaction mixture was allowed to stir over night at ambient temperature and was then concentrated under reduced pressure to provide crude product as an orange solid. The solid was loaded onto a silica gel column. The column was eluted with 47.5% methanol/2.5% ammonium hydroxide in dichloromethane. The fractions were combined and concentrated under reduced pressure to provide an orange solid. The solid was triturated with hot acetonitrile and methanol and then allowed to cool. The solid was isolated by filtration and then washed sequentially with acetonitrile and diethyl ether to provide 3.5 g of 4-amino-1-(2-aminoethyl)-1H-imidazo[4,5-c][1,5]naphthyridin-2-ol.

Part C

A solution containing 4-amino-1-(2-aminoethyl)-1H-imidazo[4,5-c][1,5]naphthyridin-2-ol (1 eq) and N,N-dimethylacetamide (2 eq) in methanol (1 mL) was added to a test tube containing a reagent (2 eq) from the table below. The reaction mixture was vortexed over night at ambient temperature. The reaction mixture was quenched with water (100 μL) and the volatiles were removed by vacuum centrifugation. The compounds were purified by preparative high performance liquid chromatography (prep HPLC) using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. The table below shows the reagent used for each example, the structure of the resulting compound, and the observed accurate mass for the isolated trifluoroacetate salt.

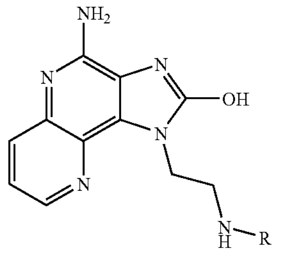

| Example | Reagent | R | Measured Mass (M + H) |
|---|---|---|---|
| 7 | None | 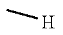 | 245.1168 |
| 8 | Methyl chloroformate | 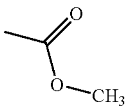 | 303.1224 |

-continued

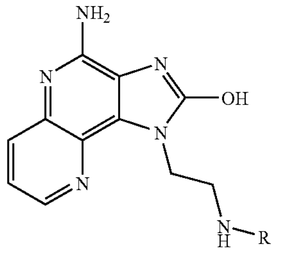

| Example | Reagent | R | Measured Mass (M + H) |
|---|---|---|---|
| 9 | Cyclopropane-carbonyl chloride | 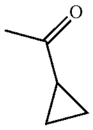 | 313.1436 |
| 10 | Isobutyryl chloride | 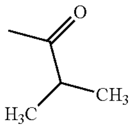 | 315.1593 |
| 11 | Cyclobutane-carbonyl chloride | 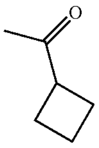 | 327.1587 |
| 12 | Pivaloyl chloride | 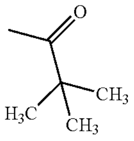 | 329.1737 |
| 13 | 3-Furoyl chloride | 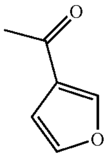 | 339.1237 |
| 14 | Isoxazole-5-carbonyl chloride | 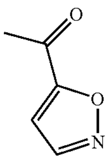 | 340.1180 |
| 15 | Cyclopentane-carbonyl chloride | 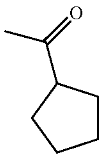 | 341.1740 |
| 16 | Benzoyl chloride | 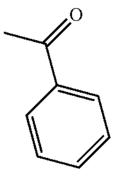 | 349.1436 |

-continued

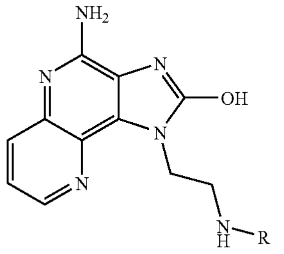

| Example | Reagent | R | Measured Mass (M + H) |
|---|---|---|---|
| 17 | 1-Methylpyrrole-2-carbonyl chloride | 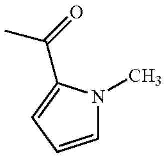 | 352.1547 |
| 18 | m-Toluoyl chloride | 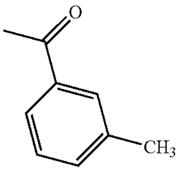 | 363.1554 |
| 19 | o-Toluoyl chloride | 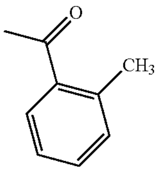 | 363.1560 |
| 20 | Phenylacetyl chloride | 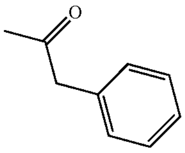 | 363.1597 |
| 21 | 2-Fluorobenzoyl chloride | 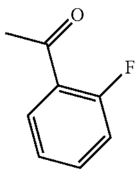 | 367.1342 |
| 22 | Isonicotinoyl chloride hydrochloride | 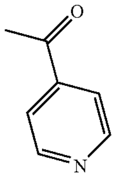 | 350.1393 |
| 23 | Nicotinoyl chloride hydrochloride | 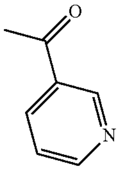 | 350.1396 |

-continued

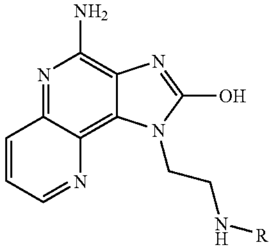

| Example | Reagent | R | Measured Mass (M + H) |
|---|---|---|---|
| 24 | Picolinoyl chloride hydrochloride | 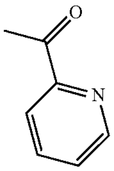 | 350.1387 |
| 25 | 3-Dimethylamino-benzoyl choride | 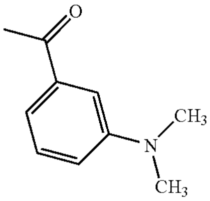 | 392.1870 |
| 26 | Methanesulfonyl chloride | 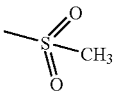 | 323.0957 |
| 27 | 1-Propanesulfonyl chloride | 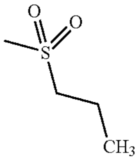 | 351.1267 |
| 28 | Dimethylsulfamoyl chloride | 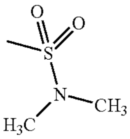 | 352.1219 |
| 29 | 1-Butanesulfonyl chloride | 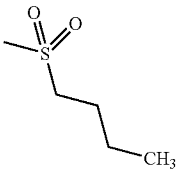 | 365.1408 |
| 30 | 1-Methylimidazole-4-sulfonyl chloride | 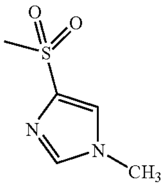 | 389.1144 |

-continued

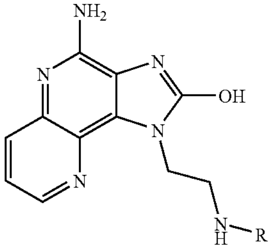

| Example | Reagent | R | Measured Mass (M + H) |
|---|---|---|---|
| 31 | 4-Fluorobenzene-sulfonyl chloride | 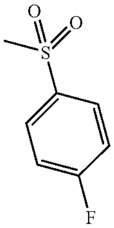 | 403.0996 |
| 32 | 3,5-Dimethyl-isoxazole-4-sulfonyl chloride | 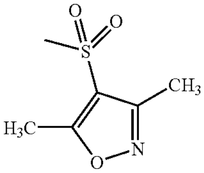 | 404.1122 |
| 33 | 8-Quinolinesulfonyl choride | 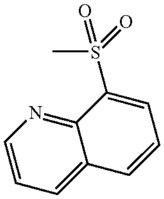 | 436.1186 |
| 34 | 5-Chloro-1,3-dimethylpyrazole-4-sulfonyl chloride | 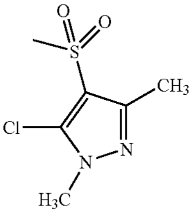 | 437.0938 |
| 35 | N-Acetylsulfanilyl choride | 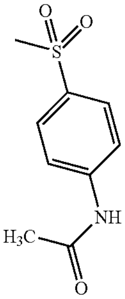 | 442.1311 |

-continued

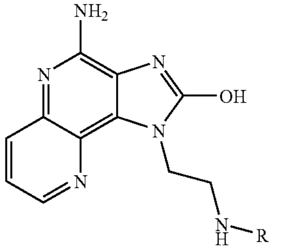

| Example | Reagent | R | Measured Mass (M + H) |
|---|---|---|---|
| 36 | 3-(Trifluoromethyl)-benzenesulfonyl chloride | 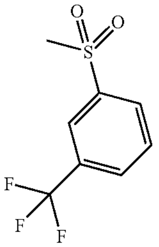 | 453.0977 |
| 37 | Ethyl isocyanate | 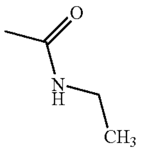 | 316.1529 |
| 38 | Isopropyl isocyanate | 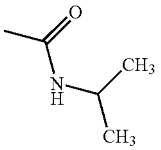 | 330.1696 |
| 39 | N-Propyl isocyanate | 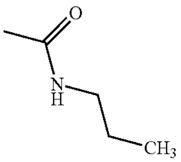 | 330.1710 |
| 40 | N-Butyl isocyanate | 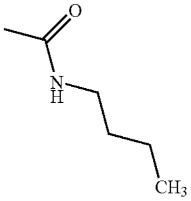 | 344.1836 |
| 41 | tert-Butyl isocyanate | 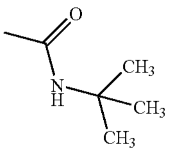 | 344.1862 |
| 42 | Cyclopentyl isocyanate | 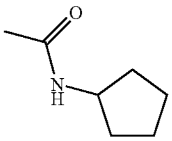 | 356.1850 |

-continued

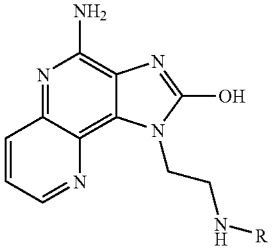

| Example | Reagent | R | Measured Mass (M + H) |
|---|---|---|---|
| 43 | Furfuryl isocyanate | 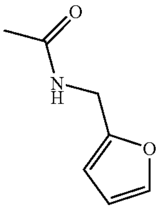 | 368.1501 |
| 44 | Cyclohexanemethyl isocyanate | 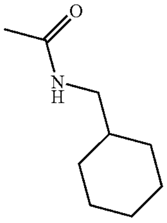 | 384.2166 |
| 45 | 3-Chlorophenyl isocyanate | 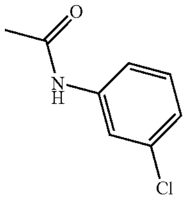 | 398.1115 |
| 46 | (S)-(−)-2-Isocyanato-3-methylbutyric acid methyl ester | 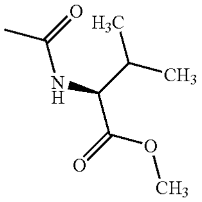 | 402.1893 |
| 47 | N,N-Dimethyl-carbamoyl chloride | 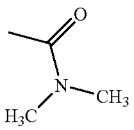 | 316.1530 |
| 48 | 1-Piperidine-carbonyl choride | 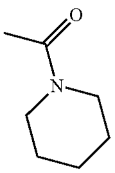 | 356.1834 |

-continued

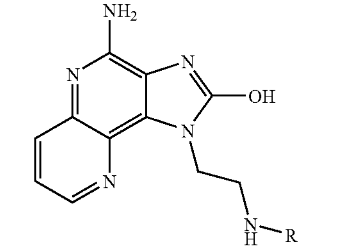

| Example | Reagent | R | Measured Mass (M + H) |
|---|---|---|---|
| 49 | 4-Morpholinyl-carbonyl chloride | 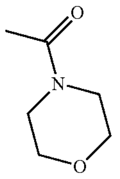 | 358.1642 |

Exemplary Compounds

Certain exemplary compounds, including some of those described above in the Examples, have the following Formula ($II_c$) and an $R_{1c}$ and an $R_{3c}$ substituent shown in the following table, wherein each line of the table is matched with the Formula ($I_c$) to represent a specific embodiment of the invention.

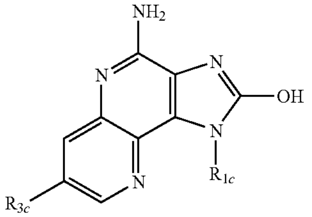

$II_c$

| $R_{1c}$ | $R_{3c}$ |
|---|---|
| benzyl | hydrogen |
| 1-phenylethyl | hydrogen |
| tetrahydro-2H-pyran-4-ylmethyl | hydrogen |
| benzyl | pyridin-3-yl |
| 1-phenylethyl | pyridin-3-yl |
| tetrahydro-2H-pyran-4-ylmethyl | pyridin-3-yl |
| benzyl | hydroxy |
| 1-phenylethyl | hydroxy |
| tetrahydro-2H-pyran-4-ylmethyl | hydroxy |
| benzyl | benzyloxy |
| 1-phenylethyl | benzyloxy |
| tetrahydro-2H-pyran-4-ylmethyl | benzyloxy |

Compounds of the invention have been found to modulate cytokine biosynthesis by inducing the production of interferon α, or interferon α and tumor necrosis factor α in human cells when tested using one of the methods described below.

CYTOKINE INDUCTION IN HUMAN CELLS

An in vitro human blood cell system is used to assess cytokine induction. Activity is based on the measurement of interferon (α) and tumor necrosis factor (α) (IFN-α and TNF-α, respectively) secreted into culture media as described by Testerman et al. in "Cytokine Induction by the Immunomodulators Imiquimod and S-27609", *Journal of Leukocyte Biology,* 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4\times10^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 μM. Controls include cell samples with media only, cell samples with DMSO only (no compound), and cell samples with reference compound.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (usually 30-0.014 μM). The final concentration of PBMC suspension is $2\times10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30 to −70° C. until analysis. The samples are analyzed for IFN-α by ELISA and for TNF-α by IGEN/BioVeris Assay.

Interferon (α) and Tumor Necrosis Factor (a) Analysis

IFN-α concentration is determined with a human multi-subtype calorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (μmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

CYTOKINE INDUCTION IN HUMAN CELLS

High Throughput Screen

The CYTOKINE INDUCTION IN HUMAN CELLS test method described above was modified as follows for high throughput screening.

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4\times10^6$ cells/mL in RPMI complete (2-fold the final cell density). The PBMC suspension is added to 96-well flat bottom sterile tissue culture plates.

Compound Preparation

The compounds are solubilized in dimethyl sulfoxide (DMSO). The compounds are generally tested at concentrations ranging from 30-0.014 μM. Controls include cell samples with media only, cell samples with DMSO only (no compound), and cell samples with a reference compound 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) on each plate. The solution of test compound is added at 7.5 mM to the first well of a dosing plate and serial 3 fold dilutions are made for the 7 subsequent concentrations in DMSO. RPMI Complete media is then added to the test compound dilutions in order to reach a final compound concentration of 2-fold higher (60-0.028 μM) than the final tested concentration range.

Incubation

Compound solution is then added to the wells containing the PBMC suspension bringing the test compound concentrations to the desired range (usually 30-0.014 μM) and the DMSO concentration to 0.4%. The final concentration of PBMC suspension is $2\times10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200 g) at 4° C. 4-plex Human Panel MSD MULTI-SPOT 96-well plates are pre-coated with the appropriate capture antibodies by MesoScale Discovery, Inc. (MSD, Gaithersburg, Md.). The cell-free culture supernatants are removed and transferred to the MSD plates. Fresh samples are typically tested, although they may be maintained at −30 to −70° C. until analysis.

Interferon-α and Tumor Necrosis Factor-α Analysis

MSD MULTI-SPOT plates contain within each well capture antibodies for human TNF-α and human IFN-α that have been pre-coated on specific spots. Each well contains four spots: one human TNF-α capture antibody (MSD) spot, one human IFN-α capture antibody (PBL Biomedical Laboratories, Piscataway, N.J.) spot, and two inactive bovine serum albumin spots. The human TNF-α capture and detection antibody pair is from MesoScale Discovery. The human IFN-α multi-subtype antibody (PBL Biomedical Laboratories) captures all IFN-α subtypes except IFN-α F (IFNA21). Standards consist of recombinant human TNF-α (R&D Systems, Minneapolis, Minn.) and IFN-α (PBL Biomedical Laboratories). Samples and separate standards are added at the time of analysis to each MSD plate. Two human IFN-α detection antibodies (Cat. Nos. 21112 & 21100, PBL) are used in a two to one ratio (weight:weight) to each other to determine the IFN-α concentrations. The cytokine-specific detection antibodies are labeled with the SULFO-TAG reagent (MSD). After adding the SULFO-TAG labeled detection antibodies to the wells, each well's electrochemoluminescent levels are read using MSD's SECTOR HTS READER. Results are expressed in pg/mL upon calculation with known cytokine standards.

Assay Data and Analysis

In total, the data output of the assay consists of concentration values of TNF-α or IFN-α (y-axis) as a function of compound concentration (x-axis).

A plate-wise scaling is performed within a given experiment aimed at reducing plate-to-plate variability associated within the same experiment. First, the greater of the median DMSO (DMSO control wells) or the experimental background (usually 20 pg/mL for IFN-α and 40 pg/mL for TNF-α) is subtracted from each reading. Negative values that may result from background subtraction are set to zero. Each plate within a given experiment has a reference compound that serves as a control. This control is used to calculate a median expected area under the curve across all plates in the assay. A plate-wise scaling factor is calculated for each plate as a ratio of the area of the reference compound on the particular plate to the median expected area for the entire experiment. The data from each plate are then multiplied by the plate-wise scaling factor for all plates. Only data from plates bearing a scaling factor of between 0.5 and 2.0 (for both cytokines IFN-α, TNF-α) are reported. Data from plates with scaling factors outside the above mentioned interval are retested until they bear scaling factors inside the above mentioned interval. The above method produces a scaling of the y-values without altering the shape of the curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91). The median expected area is the median area across all plates that are part of a given experiment.

A second scaling may also be performed to reduce inter-experiment variability (across multiple experiments). All background-subtracted values are multiplied by a single adjustment ratio to decrease experiment-to-experiment variability. The adjustment ratio is the area of the reference compound in the new experiment divided by the expected area of the reference compound based on an average of previous experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from an average of previous experiments.

The minimum effective concentration is calculated based on the background-subtracted, reference-adjusted results for a given experiment and compound. The minimum effective concentration (μmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the Formula I:

I

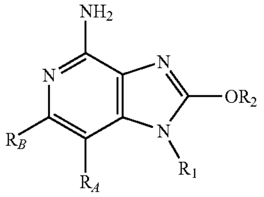

wherein:

$R_2$ is selected from the group consisting of hydrogen, $C_{1-4}$ alkyl, hydroxy$C_{2-4}$ alkylenyl, and $C_{1-4}$ alkoxy$C_{2-4}$ alkylenyl;

$R_1$ is selected from the group consisting of benzyl, 1-phenylethyl, and pyridinylmethyl, each of which is unsubstituted or substituted by one or more substituents independently selected from the group consisting of alkyl, alkoxy, haloalkyl, haloalkoxy, and halogen; and tetrahydropyranylmethyl;

$R_A$ and $R_B$ taken together form a fused pyridine ring that is unsubstituted or substituted by one $R_3$ group, or substituted by one $R_3$ group and one R group, or substituted by one or more R groups;

or $R_A$ and $R_B$ taken together form a fused tetrahydropyridine ring that is unsubstituted or substituted by one or more R groups;

R is selected from the group consisting of:

halogen,
hydroxy,
alkyl,
alkenyl,
haloalkyl,
alkoxy,
alkylthio, and $—N(R_9)_2$;

$R_3$ is selected from the group consisting of:

$—Z—R_4$,
$—Z—X—R_4$,
$—Z—X—Y—R_4$,
$—Z—X—Y—X—Y—R_4$, and
$—Z—X—R_5$;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:

—O—,
$—S(O)_{0-2}—$,
$—S(O)_2—N(R_8)—$,
$—C(R_6)—$,
$—C(R_6)—O—$,
$—O—C(R_6)—$,
—O—C(O)—O—,
$—N(R_8)-Q-$,
$—C(R_6)—N(R_8)—$,
$—O—C(R_6)—N(R_8)—$,
$—C(R_6)—N(OR_9)—$,
$—O—N(R_8)-Q-$,
$—O—N{=}C(R_4)—$,
$—C({=}N—O—R_8)—$,
$—CH(—N(—O—R_8)-Q-R_4)—$,

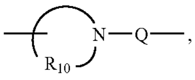,
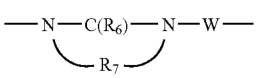,
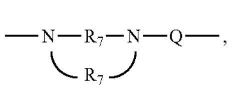,
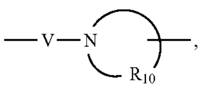, and
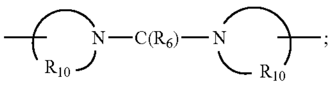;

Z is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;

$R_5$ is selected from the group consisting of:

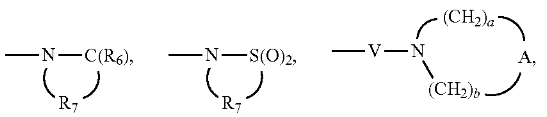

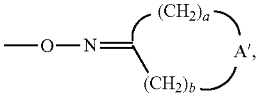

and

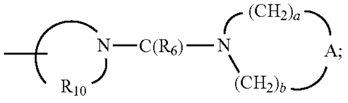

$R_6$ is selected from the group consisting of =O and =S;

$R_7$ is $C_{2-7}$ alkylene;

$R_8$ is selected from the group consisting of hydrogen, $C_{1-10}$ alkyl, $C_{2-10}$ alkenyl, hydroxy-$C_{1-10}$ alkylenyl, $C_{1-10}$ alkoxy-$C_{1-10}$ alkylenyl, aryl-$C_{1-10}$ alkylenyl, and heteroaryl-$C_{1-10}$ alkylenyl;

$R_9$ is selected from the group consisting of hydrogen and alkyl;

$R_{10}$ is $C_{3-8}$ alkylene;

A is selected from the group consisting of $-CH_2-$, $-O-$, $-C(O)-$, $-S(O)_{0-2}-$, and $-N(-Q-R_4)-$;

A' is selected from the group consisting of $-O-$, $-S(O)_{0-2}-$, $-N(-Q-R_4)-$, and $-CH_2-$;

Q is selected from the group consisting of a bond, $-C(R_6)-$, $-C(R_6)-C(R_6)-$, $-S(O)_2-$, $-C(R_6)-N(R_8)-W-$, $-S(O)_2-N(R_8)-$, $-C(R_6)-O-$, $-C(R_6)-S-$, and $-C(R_6)-N(OR_9)-$;

V is selected from the group consisting of $-C(R_6)-$, $-O-C(R_6)-$, $-N(R_8)-C(R_6)-$, and $-S(O)_2-$;

W is selected from the group consisting of a bond, $-C(O)-$, and $-S(O)_2-$; and a and b are independently integers from 1 to 6 with the proviso that a+b is $\leqq 7$;

or a pharmaceutically acceptable salt thereof.

2. A compound selected from the group consisting of the Formulas II, III, IV, and V:

II

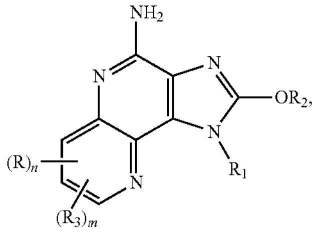

III

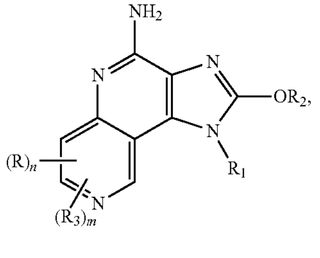

-continued

IV

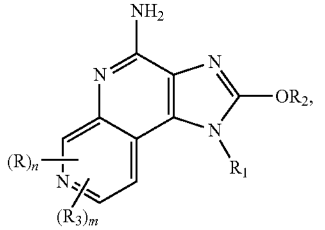

V

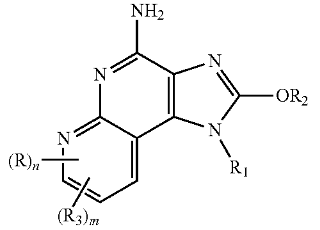

wherein:

$R_2$ is selected from the group consisting of hydrogen, $C_{1-4}$ alkyl, hydroxy$C_{2-4}$ alkylenyl, and $C_{1-4}$ alkoxy$C_{2-4}$ alkylenyl;

R is selected from the group consisting of:

halogen, hydroxy, alkyl, alkenyl, haloalkyl, alkoxy, alkylthio, and $-N(R_9)_2$;

n is an integer from 0 to 3;

$R_1$ is selected from the group consisting of benzyl, 1-phenylethyl, and pyridinylmethyl, each of which is unsubstituted or substituted by one or more substituents independently selected from the group consisting of alkyl, alkoxy, haloalkyl, haloalkoxy, and halogen; and tetrahydropyranylmethyl;

$R_3$ is selected from the group consisting of:

$-Z-R_4$, $-Z-X-R_4$, $-Z-X-Y-R_4$, $-Z-X-Y-X-Y-R_4$, and $-Z-X-R_5$;

m is 0 or 1; with the proviso that when m is 1, then n is 0 or 1;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more $-O-$ groups;

Y is selected from the group consisting of:

$-O-$, $-S(O)_{0-2}-$, $-S(O)_2-N(R_8)-$, $-C(R_6)-$, $-C(R_6)-O-$, $-O-C(R_6)-$, $-O-C(O)-O-$, $-N(R_8)-Q-$, $-C(R_6)-N(R_8)-$,

—O—C($R_6$)—N($R_8$)—,
—C($R_6$)—N($OR_9$)—,
—O—N($R_8$)-Q-,
—O—N═C($R_4$)—,
—C(═N—O—$R_8$)—,
—CH(—N(—O—$R_8$)-Q-$R_4$)—,

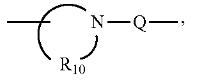, 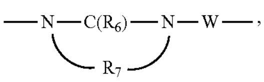,

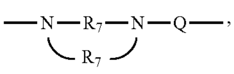, 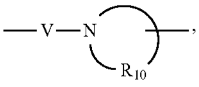, and

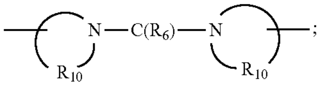;

Z is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;

$R_5$ is selected from the group consisting of:

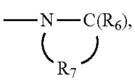, 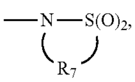, 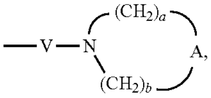,

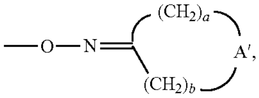, and

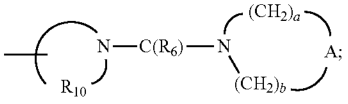;

$R_6$ is selected from the group consisting of ═O and ═S;

$R_7$ is $C_{2-7}$ alkylene;

$R_8$ is selected from the group consisting of hydrogen, $C_{1-10}$ alkyl, $C_{2-10}$ alkenyl, hydroxy-$C_{1-10}$ alkylenyl, $C_{1-10}$ alkoxy-$C_{1-10}$ alkylenyl, aryl-$C_{1-10}$ alkylenyl, and heteroaryl-$C_{1-10}$ alkylenyl;

$R_9$ is selected from the group consisting of hydrogen and alkyl;

$R_{10}$ is $C_{3-8}$ alkylene;

A is selected from the group consisting of —$CH_2$—, —O—, —C(O)—, —$S(O)_{0-2}$—, and —N(-Q-$R_4$)—;

A' is selected from the group consisting of —O—, —$S(O)_{0-2}$—, —N(-Q-$R_4$)—, and —$CH_2$—;

Q is selected from the group consisting of a bond, —C($R_6$)—, —C($R_6$)—C($R_6$)—, —$S(O)_2$—, —C($R_6$)—N($R_8$)—W—, —$S(O)_2$—N($R_8$)—, —C($R_6$)—O—, —C($R_6$)—S—, and —C($R_6$)—N($OR_9$)—;

V is selected from the group consisting of —C($R_6$)—, —O—C($R_6$)—, —N($R_8$)—C($R_6$)—, and —$S(O)_2$—;

W is selected from the group consisting of a bond, —C(O)—, and —$S(O)_2$—; and a and b are independently integers from 1 to 6 with the proviso that a+b is ≦7;

or a pharmaceutically acceptable salt thereof.

3. The compound or salt of claim 2 wherein the compound is of the Formula II:

II

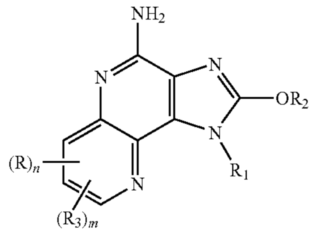

or a pharmaceutically acceptable salt thereof.

4. A compound selected from the group consisting of the Formulas VI, VII, VIII, and IX:

VI

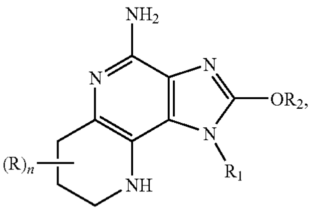

VII

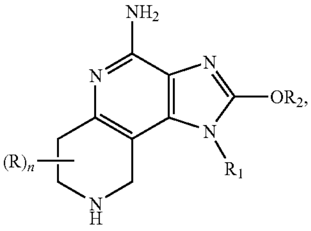

VIII

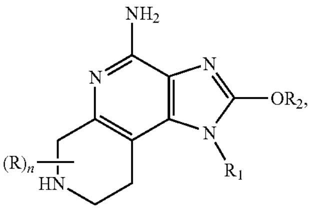

IX

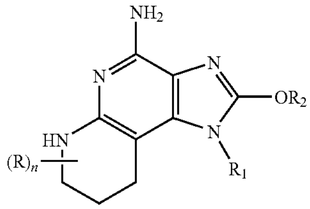

wherein:

$R_2$ is selected from the group consisting of hydrogen, $C_{1-4}$ alkyl, hydroxy$C_{2-4}$ alkylenyl, and $C_{1-4}$ alkoxy$C_{2-4}$ alkylenyl;

R is selected from the group consisting of:
halogen,
hydroxy,
alkyl,
alkenyl,
haloalkyl,
alkoxy,
alkylthio, and
$—N(R_9)_2$;

n is an integer from 0 to 3; and $R_1$ is selected from the group consisting of benzyl, 1-phenylethyl, and pyridinylmethyl, each of which is unsubstituted or substituted by one or more substituents independently selected from the group consisting of alkyl, alkoxy, haloalkyl, haloalkoxy, and halogen; and tetrahydropyranylmethyl;

or a pharmaceutically acceptable salt thereof.

5. The compound or salt of claim 4 wherein the compound is of the Formula VI:

VI

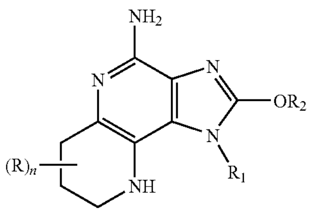

or a pharmaceutically acceptable salt thereof.

6. The compound or salt of claim 2 wherein m is 0.

7. The compound or salt of claim 2 wherein $R_3$ is at the 7-position.

8. The compound or salt of claim 1 wherein $R_3$ is pyridin-3-yl, 3-hydroxyphenyl, 4-hydroxymethylphenyl, or benzyloxy.

9. The compound or salt of claim 1 wherein R is hydroxy.

10. The compound or salt of claim 1 wherein $R_2$ is hydrogen.

11. The compound or salt of claim 1 wherein $R_1$ is selected from the group consisting of benzyl, 4-methoxybenzyl, 1-phenylethyl, and pyridin-3-ylmethyl.

12. The compound or salt of claim 11 wherein $R_1$ is selected from the group consisting of benzyl and 1-phenylethyl.

13. The compound or salt of claim 1 wherein $R_1$ is tetrahydro-2H-pyran-4-ylmethyl.

14. A pharmaceutical composition comprising a therapeutically effective amount of a compound or salt of claim 1 and a pharmaceutically acceptable carrier.

* * * * *